US009167840B2

(12) United States Patent
Yoon et al.

(10) Patent No.: US 9,167,840 B2
(45) Date of Patent: *Oct. 27, 2015

(54) PRODUCTION AND EXTRACTION OF PROCYANIDINS FROM PLANT CELL CULTURES

(75) Inventors: Sung-Yong Harrison Yoon, Lake Oswego, OR (US); Young Chul Park, Beaverton, OR (US); Amy McDonald, Oregon City, OR (US); Camille Pierre Dubois, Wilsonville, OR (US); Sonia Lall, Portland, OR (US)

(73) Assignee: DianaPlantScience, Inc., Portland, OR (US)

( * ) Notice: Subject to any disclaimer, the term of this patent is extended or adjusted under 35 U.S.C. 154(b) by 131 days.

This patent is subject to a terminal disclaimer.

(21) Appl. No.: 13/251,960

(22) Filed: Oct. 3, 2011

(65) Prior Publication Data

US 2012/0142105 A1 Jun. 7, 2012

Related U.S. Application Data

(63) Continuation-in-part of application No. PCT/US2009/042722, filed on May 4, 2009.

(60) Provisional application No. 61/389,629, filed on Oct. 4, 2010, provisional application No. 61/166,591, filed on Apr. 3, 2009.

(51) Int. Cl.
*A01H 5/12* (2006.01)
*A01H 5/08* (2006.01)
(Continued)

(52) U.S. Cl.
CPC .............. *A23L 1/3002* (2013.01); *A01H 4/001* (2013.01); *A01H 5/08* (2013.01); *A01H 5/12* (2013.01);
(Continued)

(58) Field of Classification Search
CPC ............ A61K 31/353; A61K 2300/00; A61K 36/185; A61K 45/06; A61K 9/20; A61K 35/78; C07D 311/62; C07D 311/74; C07D 311/78; C07D 401/12; C07D 405/12; A23V 2002/00; A23G 1/56; A23L 1/3002; C12N 5/00; A01H 5/10; A01H 4/00
See application file for complete search history.

(56) References Cited

U.S. PATENT DOCUMENTS 75,020 A 12/1867 Gould et al.
4,306,022 A 12/1981 Kinsella et al.
(Continued)

FOREIGN PATENT DOCUMENTS

JP 2006-516540 7/2006
WO 97/36497 10/1997
(Continued)

OTHER PUBLICATIONS

Blum, Deborah. The Curious (Toxic) Chemistry of Chocolate. Speakeasy Science. Feb. 14, 2012. Available at: blogs.plos.org/speakeasyscience.*

(Continued)

*Primary Examiner* — Anne Grunberg
(74) *Attorney, Agent, or Firm* — Workman Nydegger

(57) ABSTRACT

A method of preparing cocoa oligomeric procyanidins from cocoa cell cultures grown in the presence of monosaccharide can increase production of procyanidins as follows: culturing cells sufficient to result in production of cocoa oligomeric procyanidins at a first rate; and introducing a monosaccharide to the cells sufficient for inducing the cells to produce the cocoa oligomeric procyanidins at a second rate that his higher than the first rate. The method can further include extracting the cocoa oligomeric procyanidins from the cells, and such extracting can occur between 1 day to 21 days after introduction of the monosaccharide. Optionally, the monosaccharide can be introduced in an amount about 0.5% to about to about 20% by volume of the culture medium. The monosaccharide can be glucose, sucrose, fructose, or the like. The monosaccharide can be introduced during or after a last phase of an exponential growth state.

25 Claims, 17 Drawing Sheets

(51) Int. Cl.

| | |
|---|---|
| C12N 5/00 | (2006.01) |
| C12N 5/02 | (2006.01) |
| A23L 1/30 | (2006.01) |
| C07D 311/62 | (2006.01) |
| A61K 36/185 | (2006.01) |
| A01H 4/00 | (2006.01) |
| C12N 5/04 | (2006.01) |

(52) U.S. Cl.
CPC .............. *A23L 1/3006* (2013.01); *A61K 36/185* (2013.01); *C07D 311/62* (2013.01); *C12N 5/0025* (2013.01); *C12N 5/04* (2013.01)

(56) References Cited

U.S. PATENT DOCUMENTS

| | | |
|---|---|---|
| 4,545,147 A | 10/1985 | Janick et al. |
| 5,407,816 A | 4/1995 | Bringi et al. |
| 5,554,645 A | 9/1996 | Romanczyk, Jr. et al. |
| 5,853,728 A | 12/1998 | Tanabe et al. |
| 5,871,979 A | 2/1999 | Choi et al. |
| 6,194,020 B1 | 2/2001 | Myers et al. |
| 6,225,338 B1 | 5/2001 | Romanczyk, Jr. et al. |
| 6,248,572 B1 | 6/2001 | Choi et al. |
| 6,312,753 B1 | 11/2001 | Kealey et al. |
| 6,589,765 B1 | 7/2003 | Choi et al. |
| 6,627,232 B1 | 9/2003 | Hammerstone, Jr. et al. |
| 6,638,971 B2 | 10/2003 | Romanczyk, Jr. et al. |
| 6,998,417 B2 | 2/2006 | Romanczyk, Jr. et al. |
| 7,122,574 B2 | 10/2006 | Romanczyk, Jr. et al. |
| 7,264,951 B1 | 9/2007 | Bringi et al. |
| 7,314,634 B2 | 1/2008 | Hernandez et al. |
| 7,320,797 B2 | 1/2008 | Gupta |
| 8,568,798 B2 * | 10/2013 | Venkatramesh et al. ...... 424/725 |
| 2001/0047524 A1 | 11/2001 | Guiltinan et al. |
| 2003/0203962 A1 | 10/2003 | Howell et al. |
| 2004/0162338 A1 | 8/2004 | Schmitz |
| 2005/0089592 A1 | 4/2005 | Chevaux et al. |
| 2006/0021084 A1 | 1/2006 | Abraham et al. |
| 2006/0078872 A1 | 4/2006 | Taguchi et al. |
| 2007/0075020 A1 | 4/2007 | Kelm et al. |
| 2007/0148107 A1 | 6/2007 | Sies et al. |
| 2008/0003314 A1 | 1/2008 | Ochiai et al. |
| 2008/0060093 A1 | 3/2008 | Zieler et al. |
| 2008/0134356 A1 | 6/2008 | Rommens |
| 2008/0274234 A1 | 11/2008 | Miller |
| 2010/0189829 A1 | 7/2010 | Bernaert et al. |
| 2010/0236143 A1 | 9/2010 | Florin et al. |

FOREIGN PATENT DOCUMENTS

| | | |
|---|---|---|
| WO | 99/00487 | 1/1999 |
| WO | 2004/050614 A1 | 6/2004 |
| WO | 2006/117465 | 11/2006 |
| WO | 2010/114567 | 10/2010 |

OTHER PUBLICATIONS

Borrell, Brendan. "Make it a decaf The enduring quest for a coffee bean without the buzz." Nature. vol. 483, pp. 264-266 Mar. 15, 2012.*
Counet, Christine and Sonia Collin. "Effect of the Number of Flavanol Units on the Antioxidant Activity of Procyanidin Fractions Isolated from Chocolate." Journal of Agricultural and Food Chemistry. 2003 V. 51, pp. 6816-6822.*
Gu, Liwei et al. "Procyanidin and Catechin Contents and Antioxidant Capacity of Cocoa and Chocolate Products" J. Agric. Food Chem. 2006, 54, 4057-4061.*
Guiltinan, Mark et al. "Cacao Tissue Culture Protocol Book Version 1.4" The Pennsylvania State University. Jan. 7, 2003.*
Holt, Roberta et al. "Procyanidin dimer B2 [epicatechin-(4B-8)-epicatechin] in human plasma after the consumption of a flavanol-rich cocoa" American Journal of Clinical Nutrition 2002 76:798-804.*
Kelm, Mark A. et al. "High-Performance Liquid Chromatography Separation and Purification of Cacao (*Theobroma cacao* L.) Procyanidins According to Degree of Polymerization Using a Diol Stationary Phase." J. Agric. Food chem. 2006, 54, 1571-1576.*
Li, Zhijian et al. "Somatic Embryogenesis and Plant Regeneration from Floral Explants of Cacao (*Theobroma cacao* L.) Using Thidiazuron" In Vitro cell Dev. Biol.—Plant 34:293-299 Oct.-Dec. 1998.*
Ogita, Shinjiro et al. "Application of RNAi to confirm theobromine as the major intermediate for caffeine biosynthesis in coffee plants with potential for construction of decaffeinated varieties." Plant Molecular Biology 54: 931-941, 2004.*
Ogita, Shinjiro et al. "Producing decaffeinated coffee plants." Nature vol. 423 Jun. 19, 2003 p. 823.*
Sain, Stephen et al. "Genetic transformation of cocoa leaf cells using *Agrobacterium tumefaciens*." Plant Cell, Tissue and Organ Culture 37: 243-251, 1994.*
Selmi, Carlo et al. "The Anti-inflammatory Properties of Cocoa Flavanols." J. Cardovasc Pharmacol 2006; 47[Suppl 2]:S163-S171.*
Tsai, C. H. et al. Tissue Culture of Cocoa Bean (*Theobroma cacao* L.): Changes in Lipids during Maturation of Beans and Growth of Cells and Calli in Culture. LIPIDS, vol. 16, No. 8 (1981) pp. 577-582.*
Willett, Elizabeth. "Research on flavanols and procyanidins provides new insights into how these phytonutrients may positively impact human health." Press Release Mars Symbioscience 6—Mar. 2012 available at www.eurekalert.org.*
Jalal and Collin, New Phytologist Sep 79, vol. 83, Issue 2, p. 343-349.*
Kieran et al, Minireview Plant cell suspension cultures: some engineering considerations, Journal of Biotechnology 59 (1997) 39-52.*
Wen et al., Cocoa Bean Cell and Embryo Culture, JAOCS, vol. 61m bi, 11 (Nov. 1984) pp. 1720-1724.*
Swain and Hillis, The Phenolic Constituents of Prunus Domestica I.—The Quantitative Analysis of Phenolic Constituents, Journal Sci. Food Agric., 10, Jan. 1959, pp. 64-68.*
Marziah et al., Production of Polyphenols in Cultured Tissues of Cocoa, *Theobroma cacao*, C.B. You et al. (eds.) Biotechnology in Agriculture, 1993 Kluwer Academic Publishers, pp. 328-331.*
Li et al., Somatic Embryogenesis and Plant Regeneration from Floral Explants of Cacao (*Theobroma cacao* L.) using Thidiazuron., In Vitro Cell. Dev. Biol.—Plant 34:293-299, 1998.*
Kubek and Shuler, The Effect of Variations in Carbon and Nitrogen Concentrations on Phenolics Formation in Plant Cell Suspension Cultures, Journal of Natural Products, 1979, vol. 43, No. 1, pp. 87-96.*
Hall and Collin, Initiation and Growth of Tissue Cultures of *Theobroma cacao*, Ann. Bot. 39, 555-70, 1975.*
International Search Report issued Jun. 23, 2009, Application No. PCT/US09/42722, filed May 4, 2009.
Supplementary EP Search Report dated Aug. 23, 2012 issued in EP 09842834, filed May 4, 2009.
International Search Report and Written Opinion dated Feb. 14, 2012, Application No. PCT/US2011/054648, filed Oct. 3, 2011.
Office Action dated Dec. 25, 2012, issued in U.S. Appl. No. 13/262,456, filed Sep. 30, 2011.
Office Action dated Nov. 6, 2012, issued in U.S. Appl. No. 13/260,667, filed Sep. 27, 2011.
Kerry L. Hale, *Molybdenum Sequestration in Brassica Species. A Role for Anthocyanins*?, Plant Physilogy, vol. 126, Aug. 2001, pp. 1391-1402.
Kumi Yoshida, *Ferric Ions Involved in the Flower Color Development of the Himalayan Blue Poppy, Meconopsis grandis*, Phytochemistry, vol. 67, 2006, pp. 992-998.
M. Marziah et al., *Production of Polyphenols in Cultured Tissues of Cocoa, Theobroma cacao*, Current Plant Science and Biotechnology in Agriculture, vol. 15, 1993, pp. 328-331.
Werner Edgar Glabgen et al., *Regulation of Enzymes Involved in Anthocyanin Biosynthesis in Carrot Cell Cultures in Response to Treatment with Ultraviolet Light and Fungal Elicitors*, Planta, vol. 204, 1998, pp. 490-498.

(56) References Cited

OTHER PUBLICATIONS

Bernard F. et al., *Comparison of Physiological and Biochemical Responds Between two Varieties of Molybdenum Glycyrrhiza Glabra and Salicylic Acid*, Scientific Information Database (SID) Rostaniha, 2008, XP002681449, abstract.

Mihoko Mori et al., *Structure of Anthocyanin from the Blue Petals of Phacelia campanularia and its Blue Flower Color Development*, Phytochemistry, vol. 67, pp. 622-629.

Luisa F. Rojas et al., *Total Polyphenols Analysis of Mature Seeds and Tissue Cultures of Some Colombians Coloa Varieties*, Actualidades Biologicas, vol. 30, No. 89, Jul. 2008, pp. 117-123.

Jorge M. Richardo da Silva et al., *Oxygen Free Radical Scavenger Capacity in Aqueous Models of Different Procyanidins from Grape Seeds*, Journal Agric. Food Chem., vol. 39, 1991, pp. 1549-1552.

J.A. Bomser et al., *Inhibition of TPA-induced Tumor Promotion in CD-1 Mouse Epidermis by a Polyphenolic Fraction from Grape Seeds*, Cancer letters, vol. 135, 1991, pp. 151-157.

Jifu Zhao et al., *Anti-Tumor-Promoting Activity of a Polyphenolic Fraction Isolated From Grape Seeds in the Mouse Skin Two-Stage Initiation-Promotion Protocol and Identification of Procyanidin B5-3'-Gallate as the Most Effective Antioxidant Constituent*, Carcinogenesis, vol. 20, No. 9, 1999, pp. 1737-1745.

B.M. Tijburg et al., *Effects of Green Tea, Black Tea and Dietary Lipophilic Antioxidants on LDL Oxidizability and Atherosclerosis in Hypercholesterolaemic Rabbits*, Atherosclorosis, vol. 135, 1997, pp. 37-47.

Jun Yamakoshi et al., *Proanthocyanidin-Rich Extract from Grade Seeds Attenuates the Development of Aortic Atherosclerosis in Cholesterol-fed Rabbits*, Atherosclerosis, vol. 42, 1999, pp. 139-149.

D. Steinberg, *Antioxidants in the Prevention of Human Atherosclerosis. Summary of the Proceedings of a National Heart, Lung, and Blood Institute Workshop*, Circulation, vol. 85, 1992, pp. 2337-2344.

L. J. Porter et al., *CACAO Procyanidins: Major Flavanoids and Identification of Some Minor Metabolites*, Phytochemistry, vol. 30, No. 5, 1991, pp. 1657-1663.

Gary E. Adamson et al., *HPLC Method for the Quantification of Procyanidins in Cocoa and Chocolate Samples and Correlation to Total Antioxidant Capacity*, Journal Agric. Food Chem., vol. 47, 1999, pp. 4184-4188.

Michael J. Muhitch et al., *Isolation and Identification of the Phenols of Paul's Scarlet Rose Stems and Stem-Derived Suspension Cultures*, Plant Physiol., vol. 75, 1984, pp. 592-595.

Nariyuki Ishikura et al., *Procyanidins and Catechin From Callus and Cell Suspension Cultures of Cryptomeria Japonica*, Agric. Biol. Chem., vol. 47, No. 2, 1983, pp. 421-423.

H. A. Stafford et al., *The Procyanidins of Douglas Fir Seedlings, Callus and Cell Suspension Cultures Derived from Cotyledons*, Phytochemistry, vol. 19, 1980, pp. 131-135.

A. Decendit et al., *Condensed Tannin and Anthocyanin Production in Vitis Vinifera Cell Suspension Cultures*, Plant Cell Reports, vol. 15, 1996, pp. 762-765.

Pierre Waffo Teguo et al., *Trans-Resveratrol-0-β-Glucoside (Piceid) in Cell Suspension Cultures of Vitis Vinifera*, Phytochemustry, vol. 42, No. 6, 1996, pp. 1591-1593.

L. Alemanno et al., *Histology of Somatic Embryogenesis from Floral Tissues Cocoa*, Plant Cell, Tissue and Organ Culture, vol. 46, 1996, pp. 187-194.

L. Alemanno et al., *A Comparison Between Theobroma cacao L. Zygotic Embryogenesis and Somatic Embryogenesis from Floral Explants*, In Vitro Cell Dev. Biol. Plant, vol. 33, Jul.-Aug.-Sep. 1997, pp. 163-172.

Zhijian Li et al., *Somatic Embryogenesis and Plant Regeneration from Floral Explants of Cacao (Theobroma cacao L.) Using Thidiazuron*, In Vitro Cell Dev. Biol. Plant, vol. 34, Oct.-Dec. 1998, pp. 293-299.

Siela N. Maximova et al., *Efficiency, Genotypic Variability, and Cellular Origin of Primary and secondary Somatic Embryogenesis of Theobroma cacao L.*, In Vitro Cell Dev. Biol. Plant, vol. 38, May-Jun. 2002, pp. 252-259.

T.R.H. Hall & H.A. Collin, *Initiation and Growth of Tissue Cultures of Theobroma cacao*, Annals of Bot., vol. 39, 1975, pp. 555-570.

Mahbubul A. F. Jalal & Hamish A. Collin, *Polyphenols of Mature Plant, Seedling and Tissue Cultures of Theobroma cacao*, Phytochemistry, vol. 16, 1977, pp. 1377-1380.

M.A.F. Jalal & H.A. Collin, *Secondary Metabolism in Tissue Cultures of Theobroma cacao*, New Phytol., vol. 83, 1979, pp. 343-349.

C.H. Tsai et al., *Cocobean Tissue Culture: Lipid Composition and Fatty Acid Metabolism*, Journal of Food Science, vol. 47, 1982, pp. 768-773.

Ming-Che Wen et al., *Cocoa Bean Cell and Embryo Culture*, Journal Am. Oil Chemist's Soc., vol. 16, No. 11, Nov. 1984, pp. 1720-1724.

Karen A. Gurney et al., *Purine Alkaloid Production and Accumulation in Cocoa Callus and Suspension Cultures*, Journal of Experimental Botany, vol. 43, No. 251, Jun. 1992, pp. 769-775.

Sumana Neera et al., *Tannin Production in Sapium Sebiferum Callus Cultures*, Phytochemistry, vol. 31, No. 12, 1992, pp. 4143-4149.

J.E. Meyer et al., *Anthocyanin Production from Vaccinium Pahalae: Limitations of the Physical Microenvironment*, Journal of Biotechnology, vol. 93, 2002, pp. 45-57.

V. C. Quesnel, *Fractionation and Properties of the Polymeric Leucocyanidin of the Seeds of Theobroma cacao*, Phytochemistry, vol. 7, 1968, pp. 1583-1592.

Mattheus F.A. Goosen, *Large-scale Insect Cell Culture: Methods, Applications and Products*, Current Opinion in Biotechnology 1991, vol. 3, 1991, pp. 365-369.

N.T. Thanh et al., *Effect of Carbon Dioxide on Cell Growth and Saponin Production in Suspension Cultures of Panax Ginseng*, Biologia Plantarum, vol. 50, No. 4, 2006, pp. 752-754.

Jeffrey L.Tate et al., *Plant Cell Growth Under Different Levels of Oxygen and Carbon Dioxide*, Plant Cell Reports, vol. 10, 1991, pp. 22-25.

T. Swain et al., *The Phenolic Constituents of Prunus Domestica*, J. Sci. Food Agric. vol. 10, 1959, pp. 63-68.

Lawrence J. Porter et al., *The Conversion of Procyanidins and Prodelphinidins to Cyanidin and Delphinidin*, Phytochemistry, vol. 25, No. 1, 1986, pp. 223-230.

Beum Jun Kim et al., *Effect of Subculture and Elicitation of Instability of Taxol Production in Taxus sp. Suspension Cultures*, Biotechnol Prog., vol. 20, No. 6, 2004, pp. 1666-1673.

Lazarus et al., *High-Performance Liquid Chromatography/Mass Spectrometry Analysis of Proanthocyanidins in Foods and Beverages*, Journal of Agric. Food Chem., vol. 47, 1999, pp. 3693-3701.

Jala et al., *Polyphenols of Mature Plant, Seedling and Tissue Cultures of Theobroma cacao*. Current Plant Science and Biotechnology in Agriculture, 1993, vol. 15, pp. 328-331.

Giacometti, *Amazonia and Caribbean Agriculture*, Chapter 19, 1994, 13 pages.

Nariyuki Ishikura et al., *Procyanidins and Catechin from Callus and Cell Suspension Cultures of Cryptomeria Japonica*, Agric. Biol. Chem., vol. 47, No. 2, 1883, pp. 421-423.

Valeria Creaser Pence et al., *Initiation and Development of Asexual Embryos*, J. Am. Soc. Hort. Sci., vol. 104, 1979, pp. 145-148.

Antonio Figueira et al., *Development of Nucellar Somatic Embryos of Theobroma cacao*, Acta Hort., vol. 336, 1993, pp. 231-238.

M. R. Sondhal et al., *Cacao Somatic Embryogenesis*, Acta Hort., vol. 336, 1993, pp. 245-248.

Dicosmo & Misawa, *Plant Cell Culture Secondary Metabolism, Chapter 2: Large-Scale Production of Secondary Metabolites by Plant Cell Cultures*, Boca Raton, Florida, Crc Press LLC, 1996, pp. 11-44.

Mattheus F. A. Goosen, *Large-scale Insect Cell Culture: Methods, Applications and Products*, Current Opinion in Biotechnology, vol. 2, 1991, pp. 365-369.

Payne et al., *Plant Cell and Tissue Culture in Liquid Systems: Elicitors*, New York, John Wiley & Sons, Inc., 1995, pp. 333.

Guohua Cao et al., *Oxygen-Radical Absorbance Capacity Assay for Antioxidants*, Free Radical Biology Med., vol. 14, No. 3, 1993, pp. 303-311.

* cited by examiner

PRODUCTION AND EXTRACTION OF PROCYANIDINS FROM PLANT CELL CULTURES

CROSS-REFERENCE TO RELATED APPLICATIONS

This application claims the benefit of and priority to U.S. Provisional Application No. 61/389,629 filed 4 Oct. 2010. This application is also a continuation-in-part of international application PCT/US2009/042722, filed 4 May 2009, which claims the benefit of and priority to U.S. Provisional Application No. 61/166,591 filed 3 Apr. 2009. Each of the above listed applications are incorporated by reference in their entirety.

BACKGROUND

Polyphenols are widely distributed in plants, fruits, and vegetables and have received considerable attention because of their physiological functions in human and animal health, including antioxidant, antimutagenic and cancer prevention activities (Salvia et al., *J. Agric. Food Chem.* 39: 1549-1552, 1991; Bomser et al., *Cancer Lett.,* 135: 151-157, 1999; Zhao et al., *Carcinogenesis,* 20: 1737-1745, 1999). Epidemiological studies have suggested that flavonoids, among the polyphenols, may reduce the risk of heart disease (Hertog et al., *Lancet:* 342: 1007-1011, 1993). Additionally, dietary flavan-3-ols and/or proanthocyanidins have been shown to reduce the incidence of atherosclerosis and coronary heart disease in experimental animals (Tijburg et al., *Atherosclorosis,* 135: 37-47, 1997; Yamakoshi et al., *Atherosclerosis,* 142: 139-149, 1999). One of the mechanisms responsible for these effects involves their inhibition of oxidation of low density lipoprotein (LDL) (Steinberg, *Circulation,* 85: 2337-2344, 1992).

The seeds of the cacao plant (*Theobroma cacao* L., Sterculiaceae) are known to be rich in polyphenols (Porter et al., *Phytochemistry,* 30: 1657-1663, 1991). Some of the antioxidant components of cacao liquor prepared from fermented and roasted cacao beans, which is a major ingredient of cocoa and chocolate products, have been characterized as flavan-3-ols and procyanidin oligomers (Sanbongi et al., *J. Agric. Food Chem.,* 46: 454-457, 1998; Adamson et al., *J. Agric. Food Chem.,* 47: 4184-4188, 1999).

Other species of *Theobroma* and other genera such as *Herrania* are also known sources of cocoa procyanidins. Twenty different species of *Theobroma* have been described but usually only 12 are accepted. Of these, nine are native to Amazonia, hence the center of genetic distribution appears to be the western half of the region (Giacometti, 1994, In "Neglected Crops: 1492 from a different perspective (J. E. Hernando Bermejo and J. Leon, Eds.) Plant Production and Protection Series No. 26, FAO, Rome, Italy, p 205-209).

The genus *Theobroma* is typically neotropical and is distributed in the tropical rain forest in the Western Hemisphere between lat. 18° N and 15° S. The region with the most species is between Costa Rica and northeastern Colombia. Five sections and 20 species are recognized. *Theobroma grandiflorum* belongs to the section *Glossopetalum*, made up of 11 species; *Theobroma cacao* is the only species of the *Theobroma* section.

Four species of *Theobroma* have been described as producers of edible flesh: *Theobroma grandiflorum, Theobroma canumanense* Pires & Froes, *Theobroma subincanum* Martius, (Cupuí in Brazil and Cacau de monte in Colombia) and *Theobroma tricolor* Humb. & Bonpl., which is a small tree distributed from western Amazonia to southern Mexico. Chocolate is also made from the seeds of these species (Giacometti, 1994, In "Neglected Crops: 1492 from a different perspective (J. E. Hernando Bermejo and J. Leon, Eds.) Plant Production and Protection Series No. 26, FAO, Rome, Italy, p 205-209). It has been shown that beans of several species of *Theobroma* and *Herrania* produce similar procyanidins and that these compounds can be extracted from the beans (Romanczyk et al., WO 97/36497).

The polyphenols in cocoa beans are stored in the pigment cells of the cotyledons. Depending on the amount of anthocyanins in those pigmented cells, also called polyphenol-storage cells, they are white to deep purple. Three groups of polyphenols can be distinguished in these cells: catechins or flavan-3-ols (~37%), anthocyanins (~4%), and proanthocyanidins (~58%). The main catechin is (−)-epicatechin which constitutes up to 35% of total polyphenol content. Procyanidins (commonly referred to as proanthocyanidins) are mainly flavan-3,4-diols, that are 4→8 or 4→6 bound to condensed dimmers, trimers, or oligomers with epicatechin as the main extension sub-unit (Romanczyk et al., WO 97/36497).

The total amount of soluble polyphenols in the dried fat-free mass of fresh cocoa beans is 15 to 20% (equaling ~6% in air dried cocoa beans, containing 54% fat and 6% moisture), and in fermented beans ~5%. Thus, one of the major drawbacks of using cocoa beans as a source of polyphenols is that most of the polyphenols are lost during processing of the beans. Other steps such as roasting and defatting also lead to losses. Thus, cocoa powder has less than 10% of the total polyphenols found in fresh beans. Another problem for using cocoa beans is the limited growth range for the plant, *Theobroma cacao*. It grows only in warm, moist climates in areas about 20° latitude north and south of the equator. This makes it difficult to preserve the polyphenol content of the beans during storage and transportation to areas where they can be processed and polyphenols extracted.

Plant cell culture is an attractive alternative to overcome these problems. Plant cell cultures have recently been used for the isolation of flavonoids. In the case of procyanidins, several groups were able to isolate particular compounds from cultures. For example, 4→8 linked (−)-epicatechin-(+)-catechin and gallic acid have been isolated from a *Rosa* culture (Muhitch & Fletcher, *Plant Physiol.,* 75:592-595, 1984). Suspension cultures and calluses of *Cryptomeria japonica* were found to produce as much as 26% of dry weight as procyanidins (Teramoto & Ishikura, *Bot. Mag. Tokyo* 98: 171-179, 1985; Ishikura & Teramoto, *Agric. Biol. Chem.* 47: 421-423, 1983), and *Pseudotsuga mensiesii* suspension cultures produced as much as 40% of their dry weight as procyanidins (Stafford & Cheng, *Phytochemistry* 19: 131-135, 1980). Reports have also shown the production of procyanidins in cell suspension cultures of *Vitis vinifera* (Decendit & Merillon, *Plant Cell Rep.* 15: 762-765, 1996; Waffo-Teguo et al., *Phytochem.* 42:1591-1593, 1996).

Tissue culture research in *Theobroma cacao* has focused on somatic embryogenesis, which has been developed in several laboratories for the purpose of clonal propagation of the plant. The first report of *Theobroma cacao* somatic embryogenesis was by Esan in 1977 (*Proc. 5th Int. Cacao Res. Conf.* 1975. Ibadan: Cacao Res. Inst. Nigeria, 1977: 116-125, 1977), who described a method using immature zygotic embryo tissue explants. Similar methods were later reported by others (Pence et al., *J. Am. Soc. Hort. Sci.* 104: 145-148, 1979; Villalobos & Aguilar, *Abstr. VII Int. Congr. Plant Tissue and Cell Cult., Amsterdam, Int. Assoc. for Plant Tissue Culture,* pp 140, 1990). Later studies were focused on development of tissue culture methods from somatic tissues including leaves (Litz, In Dimick, P. S., Ed., *Cacao biotechnology symposium*. The Pennsylvania State University Press, University Park, Pa., pp 111-120, 1986), nucellus (Chatelet et al., *C.R. Acad. Sci., Paris* 315: 55-62, 1992; Figueira & Janick, *Acta Hort.* 336: 231-238, 1993; Sondhal et al., *Acta Hort.* 336: 245-248, 1993), and floral explants including petals and staminodes (Lopez-Baez et al., *C.R. Acad. Sci., Paris* 316: 579-584, 1993; Alemanno et al., *Plant Cell Tiss. Organ Cult.* 46: 187-194, 1996; Alemanno & Michaux-Ferriere, *In Vitro Cell Dev. Biol. Plant* 33: 163-172, 1997). These early methods, though successful, were not applicable to all genotypes and the frequency of regenerated plants was low. More efficient methods capable of propagating a wide range of genotypes were also developed (Li et al., *In Vitro Cell Dev. Biol. Plant* 34: 293-299, 1998; Maximova et al., *In Vitro Cell Dev. Biol. Plant* 38: 252-259, 2002). However, all the described methods, while using tissue culture methods to produce somatic embryos, did not teach methods to raise suspension cells.

There is limited amount of published work on developing cell cultures of *Theobroma cacao*. Most of this work was in the 1970's and 1980's (Hall & Collin, *Annals of Bot.* 39: 555, 1975; Jalal & Collin, *Phytochem.* 16: 1377-1380, 1977; Jalal & Collin, *New Phytol.* 83: 343-349, 1979; Tsai et al., *J. Food Sci.* 47: 768-773, 1982; Wen et al., *J. Am. Oil Chemist's Soc.* 16: 1720-1724, 1984). Of these, only a few have studied flavonoids in cell cultures of *Theobroma cacao*. For instance, Jalal and Collin (1979) reported that the flavonoid compositions of the callus and cell suspensions were similar and much less varied than that of the original intact cotyledon. Both tissue cultures contained (−)-epicatechin, leucocyanidins, caffeic and coumaric acids. The methylated purines, theobromine and caffeine, could not be detected in the tissue cultures. However, Gurney et al. (*J. Expt. Bot.* 43: 769-775, 1992) reported that callus and suspension cultures of *Theobroma cacao* produced caffeine, theobromine and theophylline at concentrations about 10% of those found in vivo.

None of the prior art has reported the formation of oligomeric procyanidins, which in recent years have been shown to have the greatest bioefficacy. Jalal and Collin (*New Phytol.* 83: 343-349, 1979) reported the detection of leucocyanidins in cell cultures of *Theobroma cacao*. However, based on the methods used to detect the compounds it was not possible to characterize the nature or size of the leucocyanidins. Further, tissue culture methods have not been described for other species of *Theobroma* or *Herrania*.

Plant cell culture is an attractive alternative to overcome these problems. Thus, it would be advantageous to have improved plant cell culture protocols as well as extraction protocols for obtaining polyphenols, and particularly procyanidins

SUMMARY

The present disclosure relates to isolated cocoa cell lines, extracts prepared from such isolated cell lines, and methods for developing cocoa cell lines that are adapted for growth in liquid culture. The disclosure also relates to methods for selecting cell lines that produce high levels of procyanidins in cell culture and methods for extracting procyanidins from such cell cultures to produce food ingredients, food additives, therapeutic compositions, or cosmetic compositions. In addition, such isolated cells lines that are selected to produce high levels of procyanidins may also be selected to be substantially devoid of caffeine and theobromine. Caffeine and theobromine, which are generally quite plentiful in cocoa preparations, are the compounds in cocoa that are primarily responsible for the bitter taste of cocoa. Such compounds are also primarily responsible for the toxicity of cocoa products to dogs and other animals. The disclosure further relates to novel growing condition and/or culture media (e.g., liquid media) for growing cell suspension cultures of cocoa cells and liquid media compositions for enhanced procyanidin production by such suspension cells.

In one embodiment, the isolated cocoa cell line yields greater than 100 mg/L packed cell volume ("PCV"), greater than 200 mg/L PCV of procyanidins, greater than 300 mg/L PCV, greater than 400 mg/L PCV, or greater than 500 mg/L PCV. In one embodiment, the isolated cocoa cell line yields greater than 100 mg, greater than 200 mg, or at least 250 mg of procyanidins per liter of cell culture. Under the provisions of the Budapest Treaty on the International Recognition of the Deposit of Microorganisms for the Purpose of Patent Procedure, Applicant has deposited an isolated cocoa cell line (5 tubes containing 250-300 mg of callus with 5 mL of medium) with NCIMB Ltd., Ferguson Building, Craibstone Estate, Bucksburn, Aberdeen AB21 9YA, United Kingdom, on Aug. 5, 2015 under the accession number NCIMB 42228. The isolated cocoa cell line comprises cocoa callus cells derived from a *Theobroma cacao* plant, the callus cells being selected to produce greater than 100 mg of procyanidins per liter of cell culture, greater than 200 mg of procyanidins per liter of packed cells, and less than 0.5 ug caffeine and less than 0.75 ug theobromine per mg of procyanidins when grown in a cell suspension culture comprising a carbon source, a nitrogen source, and one or more supplements selected from the group consisting of a macronutrient, a micronutrient, an auxin, a cytokinin, a vitamin, an amino acid, a hormone, inositol, and a myo-inositol.

The isolated cocoa cell line may be derived from essentially any part of the cocoa plant. For example, the isolated cocoa cell line may be derived from at least one of floral tissue or a non-floral vegetative tissue. Examples of floral tissue include, but are not limited to, petals, sepals, staminodes, and combinations thereof. Examples of non-floral vegetative tissue include, but are not limited to, nodes, internodes, young leaves, mature leaves, stems, roots, and combinations thereof.

In one embodiment, the isolated cocoa cell line yields greater than 100 mg/L packed cell volume ("PCV"), greater than 200 mg/L PCV of procyanidins, greater than 300 mg/L PCV, greater than 400 mg/L PCV, or greater than 500 mg/L PCV. In one embodiment, the isolated cocoa cell line yields greater than 100 mg, greater than 200 mg, or at least 250 mg of procyanidins per liter of cell culture.

In one embodiment, methods for preparing cocoa oligomeric procyanidins from cocoa cell culture are described.

In one embodiment, a method of preparing cocoa oligomeric procyanidins can include: (1) culturing cells for a time sufficient and under conditions sufficient to result in production of cocoa oligomeric procyanidins at a first rate, and (2) introducing a monosaccharide to the cells in an amount sufficient for inducing the cells to produce the cocoa oligomeric procyanidins at a second rate that his higher than the first rate. In one aspect, the monosaccharide can be glucose, sucrose, fructose, or the like. The monosaccharide can be introduced during or after a last phase of an exponential growth state. Optionally, the monosaccharide can be introduced in an amount about 0.5% to about to about 20% by weight or volume of the culture medium. The monosaccharide can be added for stable cell line maintenance, induction of overproduction and prevention of cell aggregation.

In another embodiment, a method of preparing cocoa oligomeric procyanidins can include: (1) culturing cells for a time sufficient and under conditions sufficient to result in production of cocoa oligomeric procyanidins at a first rate, and (2) culturing the cells in a hormone-free medium and under conditions sufficient for inducing the cells to produce the cocoa oligomeric procyanidins at a second rate that his higher than the first rate. In one embodiment, the method can include introducing a monosaccharide to the cells in the hormone-free medium in an amount sufficient for inducing the cells to produce the cocoa oligomeric procyanidins at a third rate that his higher than the second rate.

According to one embodiment of the methods described herein, the methods may further include extracting the cocoa oligomeric procyanidins from the cells. In one embodiment, the extract of the cells is substantially devoid of xanthine alkaloids. Example xanthine alkaloids include, but are not limited to, caffeine, theobromine, and theophylline.

Accordingly, in yet another embodiment, a method of preparing cocoa oligomeric procyanidins can include: (1) culturing cells for a time sufficient and under conditions sufficient to result in production of cocoa oligomeric procyanidins, and (2) extracting the cocoa oligomeric procyanidins from the cells with an extraction solution. In one embodiment, the extraction solution can be ethanol-based. In one aspect, the ethanol-based extraction solution can be aqueous. In another aspect, the ethanol-based extraction solution can be devoid of any organic solvent other than ethanol. In one embodiment, the extraction solution can be an acidic extraction solution. The pH of the acidic extraction solution is from about 3 to about 6. The acidic extraction solution can include acetic acid, citric acid, or ascorbic acid. In one embodiment, the method can be performed with an acidic extraction solution that includes an antioxidant. In some instances, an acid in the acidic extraction solution is also an antioxidant. In some instances, separate acid and antioxidant are used in the extraction solution.

The methods described herein can further include extracting the cocoa oligomeric procyanidins from the cells between 1 day to 21 days (e.g., about 1 day to about 10 days) after introduction of the monosaccharide. Optionally, the monosaccharide can be introduced in an amount about 0.5% to about to about 20% by weight or volume of the culture medium. In one aspect, the culture can be cultured in a hormone-free medium.

In one embodiment, the methods can be devoid of a defatting step. That is, extracts (procyanidins, polyphenols, etc.) can be prepared from the cultured cells without having to employ a defatting step.

In one embodiment, the methods can include one or more of the following: harvesting the cells; homogenizing cell biomass in a suitable solvent for extraction of polyphenol rich fraction; isolating a procyanidin rich fraction using solvent-solvent extraction and/or chromatography; or drying or concentrating the procyanidin fraction.

In one embodiment, the methods can include one or more of the following: growing callus *Theobroma* sp. cells on solid growth medium; selecting a rapidly growing cell line from a *Theobroma cacao* callus culture; and initiating a *Theobroma* sp. cell suspension culture by inoculating the rapidly growing cell line into liquid medium.

In one embodiment, the methods can include cultivation of the cocoa cell culture in a fermenter or bioreactor vessel in the presence of dissolved gases, including oxygen, whereby the cells are subjected to elevated levels of dissolved oxygen in the liquid cultivation medium. Oxygen, either alone or as a blend of air and purified gaseous oxygen may be supplied to the fermenter or bioreactor via a sparger during the growth phase and the elicitation stage (e.g., subsequent to the introduction of the monosaccharide or subsequent to the introduction of the cells to a hormone-free medium) to favor elevated growth and production. The concentration of dissolved oxygen delivered to the cells may depend on the primary or secondary metabolic demands of the cells. In one embodiment, the step of culturing the cocoa cells is carried out in the presence of dissolved oxygen concentration at 1% to 400% of air saturation (e.g., about 1% to about 200%) during the growth stage. In another embodiment, the step of culturing the cocoa cells is carried out in the presence of dissolved oxygen concentration at 1% to 400% of air saturation (e.g., about 1% to about 200%) during the elicitation stage.

The foregoing and other objects, features, and advantages will become more apparent from the following description, which proceeds with reference to the accompanying figures.

BRIEF DESCRIPTION OF THE DRAWINGS

FIG. 2A and FIG. 2B demonstrate procyanidin productivity (FIG. 2B) and production yield (FIG. 2A) of suspension cultures from non-floral and floral tissue. FIG. 2C shows the cell selection effect on procyanidin productivity improvement. FIG. 2D shows the cell selection effect on procyanidin production yield improvement. FIG. 2E shows carbohydrate analysis of *Theobroma cacao* cell culture in Medium XXVI (Table 1).

FIGS. 8A-8C together illustrate a butanol-HCl hydrolysis assay for measuring procyanidins. Acid hydrolysis of procyanidins leads to their breakdown to two monomeric forms, (−)-Epicatechin and cyanidin which is pink in color. Intensity of pink color in each sample represents amount of procyanidins obtained in different cell lines (FIG. 8A). The method was optimized to a 96-well plate format for rapid screening of samples (FIG. 8B). The cyanidin absorption is at 520 nm and the epicatechin absorption is at 280 nm (FIG. 8C); quantification is calculated from the cyanidin absorbance value.

FIGS. 9A-9C show HPLC LC-MS analysis of various authentic standard compounds. FIGS. 9D-9F show an HPLC LC-MS analysis of *Theobroma cacao* suspension cells showing signal for epicatechin and catechin but devoid of any caffeine or theobromine.

DETAILED DESCRIPTION

Figure 1:
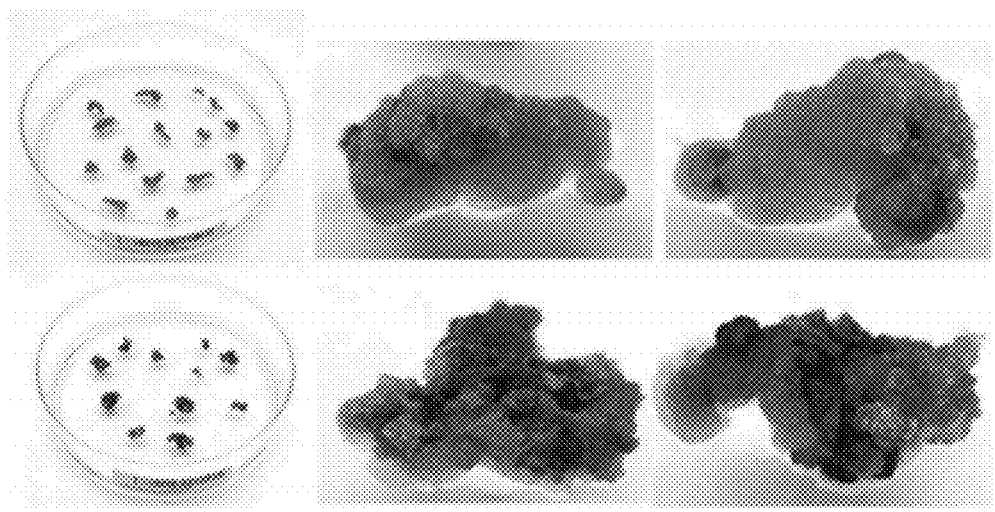
FIG. 1 includes photographs of rapidly growing cell lines.

The present disclosure relates to isolated cocoa cell lines, extracts prepared from such isolated cell lines, and methods for developing cocoa cell lines that are adapted for growth in liquid culture. The disclosure also relates to methods for selecting cell lines that produce high levels of procyanidins in cell culture and methods for extracting procyanidins from such cell cultures to produce food ingredients, food additives, therapeutic compositions, or cosmetic compositions. In addition, such isolated cells lines that are selected to produce high levels of procyanidins may also be selected to be substantially devoid of caffeine and theobromine. Caffeine and theobromine, which are generally quite plentiful in cocoa preparations, are the compounds in cocoa that are primarily responsible for the bitter taste of cocoa. Such compounds are also primarily responsible for the toxicity of cocoa products to dogs and other animals. The disclosure further relates to novel growing condition and/or culture media (e.g., liquid media) for growing cell suspension cultures of cocoa cells and liquid media compositions for enhanced procyanidin production by such suspension cells.

I. Abbreviations 2,4-D 2,4-dichlorophenoxyacetic acid
2iP 6-(γ,γ-dimethylallylamine) purine
B5 Gamborg's B5
BA Benzyl adenine
CP Chee and Poole
DKW Driver and Kuniyuki Walnut
FAB/MS Fast atom bombardment/mass spectrometry
HCl hydrochloric acid
HPLC High performance liquid chromatography
$H_2SO_4$ Sulfuric acid
IAA Indole acetic acid
IBA Indole butyric acid
LC Liquid chromatography
LSIMS Liquid secondary ion mass spectrometry
MS Mass spectroscopy
MS medium Murashige and Skoog medium
MS vitamins Murashige and Skoog vitamins
MS Salts Murashige and Skoog salts
NAA 1-Naphthalene acetic acid
NMR Nuclear magnetic resonance
NN Nitsch and Nitsch
PCV Packed cell volume
PDA Photodiode array
QL Quiorin and Lepoivre
RI Refractive index
rpm revolutions per minute
SH Schenk and Hildebrandt
TDZ thisdiazuron
TLC thin layer chromatography
vvm volume of gas per volume of culture per minute
WPM McCown's Woody Plant Medium

II. Terms

Unless otherwise noted, technical terms are used according to conventional usage. In order to facilitate review of the various embodiments of the invention, the following explanations of specific terms are provided:

Antioxidants are substances that reduce oxidative damage (damage due to oxygen) such as that caused by free radicals.

Callus is a mass of thin-walled, undifferentiated plant cells, developed as the result of wounding or culture on nutrient media.

Catechins are polyphenolic compounds which occur in plants naturally. They are also called flavan-3-ols.

Cocoa is the seed from *Theobroma cacao* (of the order Sterculiacae) and consists of mainly two varieties: Criollo and Forestero divided into several subvarities. A third group called Trinitario is a cross between Criollo and Forestero. Other species included here are, for example, *Theobroma grandiflorum, Theobroma obovatum, Theobroma speciosum, Theobroma subincanum* and *Theobroma sylvestris*.

Flavonoids are any of a group of compounds containing a characteristic aromatic trimeric heterocyclic nucleus, usually occurring in glycosidic form and widely distributed in plants, often as a pigment.

Polyphenols are water-soluble plant pigments that are also known as bioflavonoids, which encompass more than 4,000 chemically unique flavonoids that can be categorized according to their chemical structure. Polyphenol monomers include catechin, epicatechin, leucocyanidin. Polyphenol oligomers include procyanidins.

Procyanidins are polymeric compounds consisting of coupled catechin units ranging from two and greater than fifty units. Procyanidins are also commonly called proanthocyanidins or condensed tannins.

Suspension culture is the process by which either prokaryotic or eukaryotic cells are grown under controlled conditions in a liquid nutrient medium.

Tissue culture is the technique or process of keeping tissue alive and growing in a culture medium.

Xanthines, derivatives of xanthine (3,7-dihydro-purine-2, 6-dione), are a group of alkaloids that are commonly used for their effects as mild stimulants and as bronchodilators. Methylated xanthine derivatives include caffeine, paraxanthine, theophylline, and theobromine (found mainly in chocolate). These compounds inhibit phosphodiesterase and antagonize adenosine.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and"

unless the context clearly indicates otherwise. Hence "comprising A or B" means including A, or B, or A and B. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Embodiment of Invention

Development of isolated cocoa cell lines, extracts prepared from such isolated cell lines, methods for developing cocoa cell lines that are adapted for growth in liquid culture, methods for generating cell culture methods that can produce high yields of procyanidins and methods for efficiently extracting these compounds from the cultures can significantly increase the production of these valuable compounds. The use of cell cultures for producing procyanidins does not require the burdensome task of developing novel methods for processing cocoa beans to reduce losses of procyanidins. Also, cell cultures are not subject to environmental conditions that can disrupt crop production. Such cell cultures and methods are described herein.

Provided herein are isolated cocoa cell lines selected to be substantially free of caffeine and theobromine. That is, the products produced by the isolated cocoa cell line are substantially free of caffeine and theobromine. As a result, preparations (e.g., lysates, extracts, etc) derived from the isolated cocoa cell line are naturally substantially free of caffeine and theobromine. This is in contrast to typical cocoa cell preparations where caffeine and theobromine must be removed from the cocoa cell preparation with the use of a solvent extraction. Such a solvent extraction is costly and time consuming. In addition, such solvent extractions typically employ harsh solvents (e.g., hexanes) that may leave potentially toxic residues in the treated cocoa cell extract. In one embodiment, the isolated cocoa cell line may be adapted for growth in suspension cell culture.

The isolated cocoa cell line may be derived from essentially any part of the cocoa plant. For example, the isolated cocoa cell line may be derived from at least one of floral tissue or a non-floral vegetative tissue. Examples of floral tissue include, but are not limited to, petals, sepals, staminodes, and combinations thereof. Examples of non-floral vegetative tissue include, but are not limited to, nodes, internodes, young leaves, mature leaves, stems, roots, and combinations thereof.

In one embodiment, the isolated cocoa cell line yields greater than 100 mg/L packed cell volume ("PCV"), greater than 200 mg/L PCV of procyanidins, greater than 300 mg/L PCV, greater than 400 mg/L PCV, or greater than 500 mg/L PCV. In one embodiment, the isolated cocoa cell line yields greater than 100 mg, greater than 200 mg, or at least 250 mg of procyanidins per liter of cell culture.

Provided herein are methods of preparing a substantially xanthine alkaloid-free cocoa polyphenol preparation, which methods include growing *Theobroma* or *Herrania* cells in suspension culture for a time sufficient and under conditions sufficient to result in production of cocoa polyphenols, and harvesting cocoa polyphenols from the cell suspension culture. In particular embodiments, *Theobroma* or *Herrania* cells are grown in suspension culture for a time sufficient and under conditions sufficient to result in production of cocoa procyanidins (for example, oligomeric procyanidins) (e.g., from 1 to 3 weeks), and harvesting cocoa procyanidins from the cell suspension culture. In examples of these methods, the resultant cocoa polyphenol (or procyanidin) preparation is substantially (or in some cases, completely) free of detectable caffeine and/or theobromine.

Also provided are methods of producing a cell suspension culture of cacao cells. Examples of these methods involve growing callus from an immature *Theobroma* sp. floral explant or from *Theobroma* sp. vegetative material on solid growth medium; selecting a rapidly growing cell line from the *Theobroma* sp. callus culture; and initiating the cell suspension culture by inoculating the rapidly growing cell line into liquid cell culture medium. By way of example, the immature *Theobroma cacao* floral explant is in some cases selected from staminode, sepal and petal base explants. In other specific, non-limiting examples, the *Theobroma* sp. vegetative material is selected from young or mature leaves, stems, meristem, nodes, or internodes. In some instance, vegetative cell cultures can be preferred as being capable of producing more procyanidins than floral cell cultures. Such cell suspension cultures of cacao cells may be selected such that the cells and the extracts that may be produced therefrom are substantially free of caffeine and theobromine.

Also provided is a substantially xanthine alkaloid-free cocoa polyphenol (e.g., procyanidin) preparation produced using any one of the methods described herein. In particular embodiments, the cocoa polyphenol (e.g., procyanidin) preparation lacks detectable levels of xanthine alkaloids (the preparation is xanthine alkaloid-free). In specific, non-limiting examples, the cocoa polyphenol preparations comprise procyanidins (for example, oligomeric procyanidins) and are substantially free of caffeine and/or theobromine. In particular, non-limiting embodiments, the cocoa polyphenols described herein can be used in dietary, cosmetic, therapeutic, or veterinary compositions.

By way of example, a cocoa polyphenol preparation is considered substantially xanthine alkaloid-free (e.g., substantially free of caffeine and theobromine) if it contains less than 2% theobromine and less than 0.5% caffeine by weight or volume of the extract. In specific, non-limiting examples, a cocoa polyphenol preparation is considered substantially xanthine alkaloid-free if it contains less than 1.5%, less than 1%, less than 0.5%, or 0% theobromine and/or contains less than 0.25%, less than 0.2%, less than 0.1% or 0% caffeine. In another example, a cocoa procyanidin preparation is considered substantially xanthine alkaloid-free if it contains less than 2% theobromine and less than 0.5% caffeine. In specific, non-limiting examples, a cocoa polyphenol preparation is considered substantially xanthine alkaloid-free if it contains less than 1.5%, less than 1%, less than 0.5%, or 0% theobromine and/or contains less than 0.25%, less than 0.2%, less than 0.1% or 0% caffeine. The most desired substantially xanthine alkaloid-free level is 0% theobromine and 0% caffeine (the preparation is xanthine alkaloid-free). It is further contemplated that representative preparations described herein and/or produced using the methods described herein contain cocoa polyphenols that comprise catechin, epicatechin, and procyanidin oligomers. In specific examples, the oligomers are dimers through dodecamers. For instance, in some preparations the oligomers comprise dimers, trimers, tetramers, pentamers, hexamers, heptamers, octamers, nonamers, or mixtures of any two or more thereof.

Also contemplated are preparations wherein the cocoa polyphenols are cocoa procyanidins. Cocoa polyphenol preparations as provided herein may be provided in liquid form, dry form, or lyophilized form. Cocoa polyphenol may be provided without extraction in the form of dried or lyophilized cells.

In one embodiment, the addition of supplemental glucose to the suspension culture can be used to increase production of procyanidins. It has been found that adding glucose to cell culture at the end of the exponential growth stage can augment procyanidin production. As such, glucose can be used as an elicitor for increasing the production of procyanidins. The glucose may be substituted with another sugar. The glucose can be added in an amount from about 0.5% to about to about 20% by weight or volume of the culture medium, more preferably from about 1% to about 10%, more preferably from about 2% to about 8%, more preferably from about 3% to about 6%, and most preferably about 5 or 6% by weight or volume of the culture medium. Optionally, the glucose can be substituted with another monosaccharide, such as sucrose or fructose. The glucose or other monosaccharide can be added at any time during the cell culture so as to increase the production of procyanidins. The monosaccharide can be introduced from 1 to 21 days after seeding, and may be introduced one or more times before extraction of the procyanidins. In one example, the addition of monosaccharide can be add at 1 to 7 days post seeding and then again at 7 to 21 days post seeding, more particularly added at day 5 to 8 post seeding and then again at 12 to 18 days, and more particularly added at about 7 days and again at about 14 days. In another example, the addition of monosaccharide can be before, during, and/or after a late stage of the exponential growth stage, preferably at or after a late stage of the exponential growth stage. The cells can be extracted for procyanidins 1 to 21 days after glucose addition, more particularly from 7 to 18 days, or more particularly around 10 days after glucose addition.

Also provided is a substantially hormone-free cocoa polyphenol (e.g., procyanidins) preparation produced using any one of the methods described herein. In particular embodiments, the cocoa polyphenol (e.g., procyanidins) preparation lacks detectable levels of hormone. Associated methods of producing such hormone-free composition can include culturing the cells for 1 day to 3 weeks in a hormone-free cell culture medium. Surprisingly and unexpectedly, cells grown in hormone-free media produced sufficient amounts of procyanidins for extraction. The use of a hormone-free medium can be beneficial for reducing hormone levels in an extract of the cell culture. It has been found that the cell culture was viable within an acceptable range such that hormone-free media can be used in the production of procyanidins with reduced hormone content in the cell culture extract. Surprisingly and unexpectedly, it was found that use of hormone-free media also resulted in an increase in procyanidin production. Accordingly, hormone-free cell cultures can be used before extraction to reduce hormone content levels and to increase the production of procyanidins. The lack of hormone in the cell culture media can be useful in undifferentiated cells.

The cell culture method can include removing hormone from the cell culture medium at seeding or some time thereafter. The method of removing hormone can include removal of cell culture medium from cells and/or introducing a hormone-free medium to cells such that the cells are substantially devoid of hormone. In one aspect, the hormone can be removed from the cells from 1 to 14 days after seeding, more particularly from 1 to 7 days after seeding or from 7 to 14 days after seeding. The cells can be cultured in the absence of hormone for 1 to 3 weeks prior to extraction, more preferably from 1 to 2 weeks, and most preferably 1 week after culturing in absence of hormone. The seeding prior to hormone free culture media can be at 25%.

In one embodiment, cells for producing procyanidins can be cultured in the absence of hormone while being supplemented with glucose. While hormone-free media and supplemental glucose independently showed increased procyanidin production, it is surprising and unexpected that using both hormone-free media that is supplemented with glucose further increased procyanidin production over hormone-free media or supplemental glucose alone. The results of increased procyanidin production were surprising and unexpected because modulation of multiple variables in cell culture often leads to unsatisfactory results. However, in this instance the combination of hormone-free media supplemented with glucose had a substantially additive effect where the increases from hormone-free media or supplemental glucose alone were now combined to further increase procyanidin production. The steps of hormone removal from the cell culture, introduction of glucose and extraction of procyanidins can be performed by combining the features of glucose introduction and culturing in hormone-free media as discussed above.

Additionally, the combination of culturing in hormone-free media and culturing in the presence of glucose can be in tandem, where first the cells are grown in hormone-free medium before being dosed with glucose. The culture technique can include one of the following: remove hormone from cells for 1 week, add glucose, and then wait a period of 1 to 21 days before extraction of procyanidins; remove hormone from cells for 2 weeks, add glucose, and then wait a period of 1 to 21 days before extraction of procyanidins; remove hormone from cells for 3 weeks, add glucose, and then wait a period of 1 to 21 days before extraction of procyanidins; remove hormone from cells for 1 or more weeks, add glucose in two or more doses 1 to 14 days apart, and then wait a period of 1 to 21 days before extraction of procyanidins; remove hormone from cells from 0 to 14 days after seeding, add glucose as described herein, and then wait a period of 1 to 21 days before extraction of procyanidins; or other similar culturing technique.

In one embodiment, the extraction process for obtaining procyanidins can use ethanol as an extraction solvent to increase extraction efficacy of monomer-decamer procyanidins from cell culture. Now, ethanol can be used, which is more environmentally friendly as acetone is known to be an environmental contaminant. Also, the ethanol extractant can be recycled and reused. On the other hand, acetone is difficult to recycle.

In one embodiment, the extraction process for obtaining procyanidins can be conducted in the presence of an acid that can also be an antioxidant, such as ascorbic acid or citric acid. The acidic extraction solution with antioxidant properties can improve the extraction or procyanidins because of reduced oxidative degradation. Also, the extraction efficacy is increased in part due to the extraction solvent having enhanced penetration into the cells and liberation of procyanidins. Alternatively, an acid and a separate antioxidant could be used.

The cell cultures can be conducted with *Theobroma* or *Herrania* cell suspension cultures produced by any one of the described methods, as well as use of these cell suspension cultures to produce cocoa polyphenols (e.g., procyanidins) as described herein.

In one embodiment, a method of preparing a substantially xanthine alkaloid-free cocoa polyphenol preparation can include growing *Theobroma* or *Herrania* cells in suspension culture for a time sufficient and under conditions sufficient to result in production of cocoa polyphenols, and harvesting cocoa polyphenols from the cell suspension culture. In examples of this method, the resultant cocoa polyphenol preparation is substantially (or in some cases, completely) free of detectable caffeine and/or theobromine. In other specific examples, the preparation contains less than 50% of the levels of caffeine and/or theobromine as would be present in a cocoa polyphenol preparation made from fermented pods. In preferred embodiments, the cell-culture generated preparation contains less than 30%, less than 20%, less than 15%, less than 10%, or less than 5% of the levels of caffeine and/or theobromine as would be present in a cocoa polyphenol preparation made from fermented beans. In particular embodiments of the disclosed methods, *Theobroma* or *Herrania* cells are grown in suspension culture for a time sufficient and under conditions sufficient to result in production of cocoa procyanidins (for example, oligomeric procyanidins), and harvesting cocoa procyanidins from the cell suspension culture.

In representative methods provided herein, the *Theobroma* or *Herrania* cell suspension culture is produced by growing callus from an immature *Theobroma* or *Herrania* floral explant or from *Theobroma* or *Herrania* vegetative material on solid growth medium, selecting a rapidly growing cell line from the *Theobroma* or *Herrania* callus culture, and initiating the cell suspension culture by inoculating the rapidly growing cell line into liquid medium.

The production of cocoa polyphenols (including procyanidins) in certain of the provided methods includes harvesting the cells; homogenizing cell biomass in a suitable solvent (e.g., ethanol extractant) for extraction of polyphenol rich fraction; isolating a procyanidin rich fraction (e.g., using solvent-solvent extraction and/or chromatography); and optionally drying, lyophilizing, or concentrating the procyanidin fraction. Harvesting the cells in some cases comprises centrifugation, filtration, or a combination thereof.

Yet another embodiment is a method of producing a cell suspension culture of cacao cells. Examples of this method include growing callus from an immature *Theobroma* or *Herrania* floral explant or from *Theobroma* or *Herrania* vegetative material on solid growth medium; selecting a rapidly growing cell line from the *Theobroma* or *Herrania* callus culture; and initiating the cell suspension culture by inoculating the rapidly growing cell line into liquid medium. By way of example, the immature *Theobroma cacao* or *Herrania* floral explant is in some cases selected from staminode, sepal and petal base explants. In other specific, non-limiting examples, the *Theobroma cacao* or *Herrania* vegetative material is selected from young or mature leaves, stem, meristem, nodes, or internodes.

Optionally, the method of producing a cell suspension culture of cacao cells further comprises growing the cell suspension culture in flasks, any suitable culture vessels, or bioreactors. For instance, the growing in some cases is effected in vessels or bioreactors and in batch, fedbatch or continuous mode.

Also contemplated herein are *Theobroma* or *Herrania* cell suspension cultures produced by any one of the described methods, as well as use of these cell suspension cultures to produce cocoa polyphenols or, more specifically, procyanidins.

Another embodiment provided by this enclosure is a cocoa polyphenol preparation comprising a mixture of cocoa polyphenols and naturally substantially free of caffeine and theobromine, which preparation is extracted from a *Theobroma* or *Herrania* cell suspension culture. The term "naturally" in reference to "naturally substantially free of caffeine and theobromine" indicates that the relative absence of caffeine and theobromine occurs not through a purification procedure, such as LH-20 size exclusion chromatography. As such, the primary cell culture extract obtained by the processes described herein can be substantially free of caffeine and/or theobromine without additional purification. However, further purification can be performed if some caffeine and/or theobromine above a desirable level is obtained from the primary extract.

A further embodiment is a method of cocoa polyphenol extract preparation that is conducted without a defatting step using a hexane or another organic solvent. Ethanol is not considered an organic solvent for these purposes. As such, there is contemplated herein the preparation of cocoa polyphenols (for example, procyanidins) that are produced (e.g., extracted) without the use of a hexane. The cocoa polyphenol extract can be substantially or completely devoid of any organic solvent, such as hexane or acetone or the like.

It is contemplated that the cocoa polyphenol preparations provided herein may be used in a dietary composition, and/or in a therapeutic composition, and/or in a veterinary composition, and/or in a cosmetic composition.

IV. Cocoa Tissue Culture

Described herein are methods for efficiently isolating procyanidins from cell cultures of *Theobroma* or *Herrania*. Specifically, *Theobroma* or *Herrania* cell suspension cultures have been established that allow routine isolation of procyanidins that are similar to the procyanidins extracted from cocoa beans. Moreover, methods provided herein have resulted in production of prolific cell culture source of these procyanidins. Representative advantages of these methods include: reliable and continuous source of biomass due to control of climatic conditions; rapid and efficient isolation procedures that minimizes degradation of procyanidins during the extraction process; procyanidins isolated from cell culture are similar in composition to those isolated from cocoa beans; and/or techniques useful to manipulate and optimize cell culture procyanidin productivity In general, described herein is the establishment of callus cultures from various tissues of *Theobroma* or *Herrania* plant. Established calli are used to raise suspension cultures using various types of cell culture media. When stable suspension cell cultures are established the cells are extracted and analyzed for procyanidin content by recognized spectrophotometric methods, while HPLC-MS methods are used for identifying individual procyanidins. From such analysis, suspension cultures capable of producing the desired procyanidins are selected for further optimization of productivity.

Generation of Cocoa Culture

The process of generating cocoa cultures is generally outlined here, and detailed exemplary protocols are described in the Examples. Briefly, although the specifics may be varied by those skilled in the art according to known variations, initiation of the procyanidin-producing cell cultures is achieved by establishing callus and suspension cultures from explants derived from any of various plant parts, for example, floral tissues such as petals, sepals, staminodes, etc., or non-floral vegetative tissues such as node, internode, young leaves, mature leaves, as described for somatic embryogenesis. The suspension cultures are maintained in fresh suspension culture medium by periodic transfer of a portion of the cultured cells to fresh medium. Transfer schedule and inoculum density is determined by cell growth performance and sugar consumption from the medium.

One embodiment provides a method for modifying the content of procyanidins which involves initiating the procyanidin-producing cultures under conditions sufficient to initiate such cultures and establishing a production medium sufficient to establish productive cell cultures, followed by scaling up of the productive cell cultures for an appropriate amount of time to isolate the procyanidins. Accordingly, altering the conditions required to initiate a culture or establish productive cultures results in modified content (amount) of procyanidins in such cultures. Physical aspects (e.g., light irradiance) and/or chemical aspects (e.g., media composition or chemical elicitors) of the plant cell culture microenvironment may be varied to achieve the desired modified content.

For instance, carbohydrate (e.g. sucrose or glucose) concentration in a suspension medium may be increased initially or during elicitation in order to increase the amount of procyanidins in the culture. Furthermore, nitrogen sources (e.g., ammonium nitrate) may be manipulated for production of secondary metabolites in plant cell cultures (see Neera et al., Phytochemistry. 31(12): 4143-4149, 1992). Therefore, decreasing the concentration of nitrogen sources in Theobroma or Herrania cell culture medium might be used to increase production of procyanidins in the culture. In addition, infusion of certain amino acids (such as glutamine, glycine, and serine) also may significantly affect the production of secondary metabolites. As a result, the concentrations of these amino acids in Theobroma or Herrania suspension medium may be increased in order to enhance the production of procyanidins. Additional amino acids may also be included in the medium and tested for their ability to increase the production of procyanidins by suspension cultures of Theobroma or Herrania. In addition, hormones may be removed from culture medium to enhance production of procyanidins by suspension cultures of Theobroma or Herrania.

Lighting conditions also can be varied in order to achieve modified procyanidins content in cell cultures of Theobroma or Herrania. For example, the lighting can be changed by increasing irradiance or length of exposure to the light, thereby increasing procyanidin production. The wavelength of the light irradiance can also be changed to achieve increased production of procyanidins. For instance, UV light is known to induce anthocyanin production in plant cell cultures (Meyer, J. Biotechnology 93: 45-57, 2002).

Other modifications known in the art for manipulation of plant cell culture microenvironments are also contemplated as being within the scope of the present description and can be performed by anyone skilled in the art.

Additionally, the cocoa cells can be cultured as described herein. For example, the cultures can be dosed with glucose at some point prior to extraction of procyanidins. The glucose may be substituted with other sugar such as sucrose, fructose, or the like. The glucose can be introduced into a cell culture: at the time of seeding; 1-7 days after seeding; 7-14 days after seeding; 14-21 days after seeding; or combinations thereof. In another example, the cultures can be grown in a hormone-free medium prior to extraction of procyanidins. The hormone-free medium can be introduced to the cells in culture: at the time of seeding; 1-7 days after seeding; 7-14 days after seeding; 14-21 days after seeding; or combinations thereof.

Harvesting of Cocoa Cells from Culture

A batch of cells of Theobroma or Herrania producing procyanidins are grown as described herein, and cells are harvested to extract the procyanidins. Harvesting of suspension cells can be performed in a number of ways, examples of which are described herein.

Once a cell culture has reached stationary phase and the desired productivity of procyanidins is reached, the culture is allowed to settle as a compact mass in the container and the medium can be decanted, leaving behind the mostly solid cell biomass. The cell biomass is then washed to remove remaining medium and similarly decanted. Alternatively, the cell suspension can be centrifuged and the supernatant (medium) discarded followed by washing of the cell mass and centrifugation again to discard the liquid. A third option is to filter the cell culture suspension to remove the medium. Any of these methods can be employed with cell culture volumes ranging from a few milliliters to production scale volumes of several thousand liters of cultures.

Extraction Procedures

The harvested cell mass is crushed, milled or ground to homogenize the cell mass and break up the cells to enhance the surface area with extraction solvent with the sample, and to ensure that the extracted portion is representative for the entire sample.

Procyanidins are unstable compounds. Thus, if the cell biomass needs to be stored prior to extraction it is preferably stored frozen, for instance by freezing with liquid nitrogen.

Extraction of total polyphenols from cell cultures of Theobroma or Herrania is similar to procedures used for extracting total polyphenols from cocoa beans, except for a few major differences. In case of cocoa beans, the initial step after grinding the beans is to defat the ground flakes (nibs). This process results in a loss of polyphenols. Since cell cultures do not have as much fat as the beans, this step is not required. Removing this step reduces the loss of polyphenols during the extraction process from a cell culture.

Furthermore, defatting requires solvents such as hexane, and traces of the solvent are found in the final extract. This causes an unpleasant odor in extracts produced from cocoa beans, and the solvents may be toxic or undesirable for certain uses, such as a food ingredient. Since the methods described herein for extraction from cell culture biomass eliminate the use of solvents (such as hexane), there is no solvent contamination or unpleasant solvent odor in the resultant extract.

Polyphenols in a representative method are extracted from the ground, homogenized cells with 70-80% aqueous methanol or 70% aqueous acetone, or combinations thereof. Water and ethanol have also been used, though oligomeric procyanidins are extracted only partially using these solvents, and high molecular weight polymers are not extracted at all (Grayer, In J. B. Harborne, *Plant Phenolics* (Vol. 1), pp 283-323, 1989. San Diego, Academic Press, Inc.; Lee & Widmer, In L. M. L. Nollet, *Handbook of Food Analysis* (Vol. 1), pp 821-894, 1996, Basel, New York, Hong Kong, Marcel Dekker, Inc.).

In one embodiment, the extraction solvent can include ethanol. The ethanol can be an aqueous composition that includes from about 25% to about 100% ethanol by weight or volume, more preferably more than about 50%, more preferably more than 75%, and even more preferably more than 90%. Specific examples include 50% ethanol, 60% ethanol, 70% ethanol, and 80% ethanol, where FIG. 12 shows 60% ethanol being superior. In this embodiment, the ethanol extraction solvent is devoid of other alcohols or ketones.

In one embodiment, the extraction solvent can include other alcohols or ketones along with water and/or ethanol, such as aqueous organic solvents. Examples include isopropyl alcohol, ethanol, methanol, acetone, ethylacetate or a combination thereof. The aqueous organic solvents can include water from about 25% to about 99%, more preferably from about 30% to about 90%, or even more preferably more than 50% water.

In one embodiment, the extraction solvent is combined with the processed or unprocessed cells at various amounts depending on the amount of cell mass. The amount of extraction solvent can be 50% or more of the mass or volume of the cell mass, more preferably more than or about 75%, even more preferably more than or about 100%, and even more preferably more than 200% of the mass or volume of cell mass. Of course, larger volumes of extraction solvent can be used.

In one embodiment, the extraction solvent can include an acid, such as an antioxidant acid. Examples of acids include acetic acid, citric acid, or ascorbic acid. The acid can be present from about 0.05% to 10% by volume of the extraction composition or by volume of the extraction solvent, more preferably from about 0.75% to about 5%, or most preferably from about 0.1% to about 1% or to about 2% by volume of the extraction composition or by volume of the extraction solvent.

After an exhaustive extraction for minor components, individual procyanidins may be present in the extract in a dilute level. Concentration is achieved at low temperature (below 40° C.) and under reduced pressure to minimize degradation of procyanidins (Lee & Widmer. In L. M. L. Nollet, *Handbook of Food Analysis* (Vol. 1), pp 821-894, 1996, Basel, New York, Hong Kong, Marcel Dekker, Inc.).

The polyphenol extracts from cell cultures of *Theobroma* or *Herrania* at this stage are relatively clean can be analyzed immediately. One benefit of the methods described herein is that cell culture-derived extracts of *Theobroma* or *Herrania* polyphenols have undetectable levels of impurities (e.g., caffeine and theobromine) to start with, compared to polyphenol extracts of beans. However, it may be beneficial to do further clean-up to remove minor impurities, such as caffeine and theobromine. It is possible to clean up the extract to remove even traces of these impurities. Such clean-up steps can include liquid-liquid partitioning with a non-miscible solvent and column chromatography on Sephadex LH-20, polyamide, Amberlite XAD-2, preparative HPLC, and solid phase extraction (SPE) using commercially available disposable cartridges (Grayer, In J. B. Harborne, *Plant Phenolics* (Vol. 1), pp 283-323, 1989. San Diego, Academic Press, Inc.; Markham & Bloor, In C. A. Rice-Evans and L. Packer, *Flavonoids in Health and Disease*, pp 1-33, 1998, Basel, New York, Hong Kong, Marcel Dekker, Inc.). Removal of theobromine and caffeine usually can be accomplished by extraction with chloroform or methylene chloride, since most flavonoids have limited solubility in these solvents.

Analysis Procedures

Analytical techniques used for detection and identification of procyanidins from *Theobroma* or *Herrania* cell cultures are similar to those used for extracts from beans. Identification of cocoa procyanidins has predominantly been achieved using a variety of chromatographic techniques for separation of oligomers and then using independent methods for structural characterization. Quesnel (*Phytochemistry* 7: 1583-1592, 1968) and Jalal and Collin (*Phytochem.* 16: 1377-1380, 1977) identified procyanidins in cocoa using paper chromatography and TLC methods, respectively. However, although these publications acknowledged the presence of procyanidins in cocoa, the stereospecific structures of the procyanidins were not elucidated. Porter et al. (*Phytochemistry* 30: 1657-1663, 1991) conducted a rigorous investigation of procyanidins in cocoa using column chromatography, TLC, HPLC, and negative ion FAB/MS to establish the presence of procyanidin oligomers through heptamers. Additionally they confirmed the structures of procyanidins through tetramers using NMR, and found them to consist primarily of (−)-epicatechin. Evidence of cocoa procyanidin oligomers through octamers was reported by Clapperton et al. (*Proceedings, 16$^{th}$ International Conference of Groupe Polyphenols, Lisbon, Portugal; Groupe Polyphenols Norbonne, France, Vol II, pp 112-115, 1992*), who used a combination of column chromatography, reversed phase HPLC, and positive ion LSIMS to characterize the procyanidin oligomers. This work demonstrated the utility of positive ion LSIMS and the use of sodium adducts as means of identifying larger procyanidin oligomers. Unfortunately, all of these methods are laborious, require lengthy preparation times to obtain structural information, and are not amenable to high throughput analysis and screening of large numbers of cell culture samples. Also, these methods are not suitable for small samples.

For the current disclosure, we developed a high throughput microscale method for the extraction of procyanidins from *Theobroma* or *Herrania* cell cultures, reverse phase HPLC methods for rapid separation of procyanidin monomers and oligomers, and mass spectroscopy (MS) methods for simultaneous identification of procyanidin oligomers based on their molecular characteristics.

Large-scale Process Optimization of *Theobroma* or *Herrania* Cell Culture

Large-scale plant cell culture is important technology in the development of a commercial process. This can be performed in large tanks similar to those used in microbial fermentation. Productivity enhancement in these tanks can be achieved by determining biomolecular factors based on cellular growth and production characteristics in the large scale process and by optimizing large-scale bioprocess variables that enhance procyanidin productivity. Biomolecular factors include medium components, elicitors and precursors in biosynthetic pathway. Prior to large-scale process, these factors should be tested in flask-scale process, since the goal of scale-up process is to reproduce on a large scale those conditions observed to be optimal on the smaller scale. However, conditions in large-scale bioreactor culture can be different than *Theobroma* or *Herrania* suspended cells in flask-scale culture. The macrokinetics of the culture are affected by changes in environmental conditions affecting the suspended cells caused by transport limitation. For instance, while parameters of growth kinetics are scale independent, the overall growth of a cell culture in a vessel is scale dependent because of the scale dependency on transport of gaseous and dissolved nutrients and metabolites (Dicosmo & Misawa, *Plant Cell Culture Secondary Metabolism*, pp 11-44, 1996. Boca Raton, Fla., CRC Press LLC). Therefore, in scale up of the bioreactor process for cocoa procyanidin production, a number of basic experiments were performed to yield essential data of growth rate, product formation rate, nutrient uptake rate and respiration rate.

In general, high productivity in plant cell cultures can be achieved by increasing the cell concentration and specific productivity. The maximum cell concentration is dependent on the nutrient supply, yield of biomass per substrate and water content. Based on the basic data, additional environmental factors are varied one by one or multiple factors can be varied at one time to increase biomass. Bioprocess variables such aeration rate, rheological properties of suspension cultures affect mass transfer and mixing in bioreactors and in turn, influence not only cell growth but also production of plant secondary metabolites. Therefore, two stage cultures may be considered, because most polyphenols are usually non-growth associated compounds. Because single stage process ideally limits the culture to a single growth rate and presumably a single developmental stage, this operation would be unsuited when several developmental stages are prerequisite for production of the non-growth associated compounds. The variables of aeration rate, agitation speed, other mixing-related variables and even medium composition are optimized separately for growth stage and production stage. However, it is impossible to scale up a process while keeping all conditions optimal. A choice has to be made as to which variable is considered the most important.

The effects of supplementing carbon and nitrogen sources on growth and production are also studied based on basic engineering data of carbon and nitrogen consumption, since the relative amounts of carbon and nitrogen sources play an important role in enhancing the biosynthesis of secondary metabolites and cell growth (Basaria, *Current Biology*, 2: 370-374, 1990). Then, supply of oxygen and carbon dioxide can be studied. In addition to oxygen, carbon dioxide has been reported to improve cell growth and secondary metabolite production in plant cell cultures (Thanh et al., *Biologia Plantarum*, 50: 752-754, 2006; Tate & Payne, *Plant Cell Reports*, 10: 22-25, 1991). Oxygen requirements of plant cells are relatively low in cell growth stage, but may significantly increase during metabolite synthesis. The level of these gases is controlled for their optimal utilization in reactor culture of *Theobroma* or *Herrania* cells. In large scale fermentation, it is impossible to introduce the same amounts of gas (air, oxygen etc.) as can be introduced on a laboratory scale. Therefore, the mass transfer coefficient constant should be maintained in order to make the superficial gas velocity constant during the bioreactor process.

Oxygen plays a key role in the metabolism of carbon sources and it may be introduced into the growth and elicitation medium of bioreactors via a sparger at rates depending on the growth or product formation kinetics of the organism (Shuler & Kargi, *Bioprocess Engineering Basic Concepts, Second Edition*, 2002. Upper Saddle River, N.J., USA, Prentice-Hall, Inc.). Cultivation of plant cells in bioreactors in the presence of elevated dissolved oxygen levels has been demonstrated previously for taxane production (see, for example, U.S. Pat. No. 7,264,951). The effect of elevated dissolved oxygen gas levels on growth and production in cocoa cell culture was investigated in a variety of types and sizes of bioreactors, including 7.5 L and 30 L mechanically agitated reactors as well as 10 L and 20 L air-lift bioreactors. The inventors have found that gaseous regimes with elevated dissolved oxygen levels were required for large scale cocoa cell growth and elevated polyphenol production. In a blend of air and purified oxygen supplied to the bioreactor, the oxygen portion of the inlet gaseous regime may range from 1% to 100%, with optima dependent on the requirements of the cocoa cells suspension during the growth or the elicitation stages of cultivation. Dissolved oxygen concentration in the cocoa cell cultivation medium during the growth stage and the elicitation stage may range from 1% of air saturation to 400% of air saturation. The portion of oxygen that is provided via the sparger as an air/oxygen mixture into the bioreactor during the growth stage is in the range of 1% to 100% of the gaseous mixture. The portion of oxygen that is provided in an air/oxygen mixture into the bioreactor during the elicitation stage is in the range of 1% to 100% of the gaseous mixture, preferably in the range of 25% to 100%.

The use of elicitors to stimulate metabolite formation and secretion is an important process strategy. It has been very useful to reduce the process time necessary to reach a high product concentration, e.g. volumetric productivity. Further, elicitation may result in the formation of novel compounds (Payne et al., *Plant Cell and Tissue Culture in Liquid Systems*, pp 333-351, 1995, New York, John Wiley & Sons, Inc). Optimization of elicitation with several biotic/abiotic candidates is tested in large-scale reactor culture to optimize when they should be treated, what dosage can be the best, how long the cells should be exposed to them and when the cells should be harvested. Synergistic effect using multiple treatments of elicitors is also tested to enhance productivity, since each elicitor can induce different type of enzymes in biosynthetic pathway.

Reactor operation method depends on cellular dynamics for growth, production and their relationship. As described earlier, the target compounds in this study are non-growth associated, which means two-stage culture process must be considered. Therefore, fed-batch culture is a particularly attractive option when the production time is considerably longer than the time required to grow the biomass and in this case, larger steps in the volume of the succeeding bioreactors are possible, resulting in a smaller number of bioreactors in the biomass train.

V. Use and Administration of Procyanidins

Procyanidins generated by the methods disclosed herein can be administered to a subject for therapeutic, dietary, or cosmetic purposes. The subject can be a human or veterinary mammal, such as a monkey, a horse, a cow, a pig, a dog, a cat, a mouse or a rat.

With regard to therapeutic uses, the procyanidins can be used to treat or prevent several disorders or diseases, such as atherosclerosis, cardiovascular disease, cancer, blood pressure modulation and/or hypertension. For example, the procyanidins can be administered prophylactically to a subject at risk of developing a tumor, to a subject having a tumor, or to a subject previously treated for a tumor. Treatment of the tumor includes, but is not limited to, surgical removal of the tumor, chemotherapy, immunotherapy or radiation therapy. In other embodiments, the procyanidins generated by the methods disclosed herein are administered to the subject in combination with at least one additional agent either prior to, simultaneously with, or following treatment of a tumor. The additional agent can also be another agent described herein that inhibits or reduces tumor growth. Alternatively, the additional agent can be an agent that improves the subject's ability to inhibit tumor growth or an agent (such as an antibiotic) that helps the subject fight infection during the course of treatment for the tumor. For example, the additional agent can be an agent that stimulates the immune system, such as a cytokine.

Procyanidins generated by the methods provided herein can be administered to a subject at risk of developing any type of tumor or to a subject suffering from any type of tumor. The tumor can be a benign tumor or a malignant tumor. The tumor can include a carcinoma, a sarcoma, a leukemia, a lymphoma, or a tumor of the nervous system. In several specific, non-limiting embodiments, the tumor includes a breast tumor, a liver tumor, a pancreatic tumor, a gastrointestinal tumor, a colon tumor, a uterine tumor, a ovarian tumor, a cervical tumor, a testicular tumor, a prostate tumor, a brain tumor, a skin tumor, a melanoma, a retinal tumor, a lung tumor, a kidney tumor, a bone tumor, an osteosarcoma, a nasopharyngeal tumor, a thyroid tumor, a leukemia, or a lymphoma. In general, the procyanidins generated by the methods provided herein are administered to a subject in an amount sufficient to prevent or inhibit tumor growth.

In other embodiments, the procyanidins can be administered prophylactically to a subject at risk of developing atherosclerosis, cardiovascular disease, or hypertension. Alternatively, the procyanidins can be administered to a subject to treat an existing condition, such as atherosclerosis, cardiovascular disease, or hypertension. The compositions can be co-administered or sequentially administered with other agents, such as antineoplastic agents, antioxidants, or agents that alleviate the symptoms or conditions associated with atherosclerosis, cardiovascular disease, blood pressure modulation and/or hypertension.

In addition, the procyanidins generated by the methods disclosed herein can be used in dietary compositions. When orally administered in the form of a liquid, the liquid may be water-based, milk-based, tea-based, fruit juice-based, or some combination thereof. Solid and liquid formulations for internal administration can further comprise thickeners sweeteners.

The procyanidins generated by the methods disclosed herein can also be used in cosmetic compositions to improve the quality or appearance of the skin of a subject. Improved skin appearance, texture, and moisture can be achieved by administering the procyanidins composition externally, internally, or some combination thereof. An acceptable carrier may act variously as solvent, carrier, diluent or dispersant for the constituents of the composition, and allows for the uniform application of the constituents to the surface of the skin at an appropriate dilution. The acceptable carrier may also facilitate penetration of the composition into the skin.

Compositions containing the procyanidins generated by the disclosed methods are useful in a wide variety of finished products, including pharmaceutical products, food products, and beverage compositions and can be prepared in accordance with standard techniques well known to those skilled in the pharmaceutical arts. Pharmaceutical compositions that include an active agent can be formulated with an appropriate solid or liquid carrier, depending on the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the procyanidin composition to be administered can also contain minor amounts of non-toxic auxiliary substances, such as wetting or emulsifying agents, preservatives, and pH buffering agents and the like, for example sodium acetate or sorbitan monolaurate.

In addition to injectable fluids, topical and oral formulations can be employed. Oral formulations can be liquid (for example, syrups, beverages, solutions, or suspensions), or solid (for example, powders, pills, tablets, or capsules). For solid compositions, conventional non-toxic solid carriers can include pharmaceutical grades of mannitol, lactose, starch, or magnesium stearate. Topical preparations can include eye drops, ointments, creams, sprays and the like. Preferably, formulations of the present invention that are suitable for topical administration are mixed with a solvent, carrier, diluent or dispersant for the constituents of the composition, and allows for the uniform application of the constituents to the surface of the skin at an appropriate dilution. The acceptable carrier may also facilitate penetration of the composition into the skin.

The dosage form of the procyanidin composition will be determined by the mode of administration chosen. Actual methods of preparing such dosage forms are known, or will be apparent, to those skilled in the art.

The procyanidin compositions generated by the methods of this disclosure can be administered to humans or veterinary mammals on whose cells they are effective in various manners such as topically, orally, intravenously, intramuscularly, intraperitoneally, intranasally, intradermally, intrathecally, and subcutaneously. The particular mode of administration and the dosage regimen will be selected by one skilled in the art, taking into account the particulars of the case (for example, the subject, the disease, the disease state involved, and whether the treatment is prophylactic). Treatment can involve daily or multi-daily doses of compound(s) over a period of a few days to months, or even years.

Such compositions can be administered to a subject in need of such administration in dosages and by techniques well known to those skilled in the medical, nutritional, or veterinary arts taking into consideration such factors as the age, sex, weight, and condition of the particular subject and the route of administration.

Preparation, dosage, and administration of compositions for therapeutic, dietary, cosmetic, and veterinary use are well known in the art (see, for example, U.S. Pat. Nos. 5,554,645, 5,853,728, 6,194,020, 6,312,753, 6,998,417, 7,122,574, 7,314,634, 7,320,797 and U.S. Patent Application Publication No. 2007/0148107, all of which are incorporated herein by reference).

The following examples are provided to illustrate certain particular features and/or embodiments. These examples should not be construed to limit the invention to the particular features or embodiments described.

EXAMPLES

Example 1

*Theobroma cacao* Callus Induction and Proliferation from Floral Tissue

Compact callus aggregates were established using full strength Driver and Kuniyuki walnut (DKW) medium augmented with auxin (2 mg/L 2,4-dichlorophenoxyacetic acid (2,4-D)), cytokinin (0.005 mg/L thisdiazuron (TDZ)) and the other supplements (250 mg/L L-glutamine, 100 mg/L myo-inositol) under controlled conditions using [D$^+$]-glucose as the carbon source (Medium I in Table 1). The medium was sterilized by autoclaving after adjusting the pH to 5.8. Samples of *Theobroma cacao* immature flower materials were collected from a number of cultivated plants. To prevent contamination of the culture, the materials were surface-sterilized prior to introducing them to the culture medium. The material was first immersed in 1% (w/v) sodium hypochlorite for 20 minutes and gently agitated every 5 minutes. Under sterile conditions the material was decanted and rinsed three times with sterile deionized water and gently agitated during each rinse. The final rinse was decanted and only the flower buds were transferred to sterile Petri plates. The flower buds were cut across at a position ⅓ of the flower length from the base using a sterile scalpel. Staminodes, sepal and petal base explants were extracted through the opening at the cut end.

The extracted materials were plated on solid callus induction medium. About 50 explants were distributed on the entire surface across each plate. The Petri plates were sealed with parafilm and maintained in the dark at 25° C. for 14 days. Substantial callus formation was observed after 10 days. Within 14 days of placing the flower parts on callus inducing medium, the callus was separated from the explants and placed on the callus proliferation media of Medium I, II and III listed in Table 1. At four week intervals, rapidly growing cells were isolated from the surface of the callus and subcultured to fresh medium. Rapidly growing cell lines showing a whitish to pale yellow color were selected for subculture (FIG. 1).

Example 2

*Theobroma cacao* Callus Induction and Proliferation from Vegetative Tissue

Callus was established on Murashige and Skoog (MS) medium, supplemented with auxins (2 mg/L IAA and 4 mg/L IBA), cytokinins (0.005 mg/L TDZ), and L-Glutamine (250 mg/L) with Glucose (20 g/L) as the carbon source (Medium XXVII, Table 1). The medium was sterilized by autoclaving, after adjusting the pH to 5.8. Samples of *Theobroma cacao* vegetative material (young and mature leaves, nodes and internodes) was collected from a number of greenhouse grown plants. To prevent contamination of the culture, the materials were surface-sterilized prior to introducing them to the culture medium. The material was first immersed in 70% ethanol for 1 minute, followed by immersion in 25% bleach for 10 minutes and gently agitated every 5 minutes. Under sterile conditions the material was decanted and rinsed three times with sterile deionized water and gently agitated during each rinse. Leaves were cut into 5 mm squares and nodes and internodes into 1-2 mm cylinders, and explanted onto plates containing solid medium. Plates were maintained in the dark at 25° C. They were observed everyday for signs of contamination and the contaminated material was discarded. Callus formation was observed after 4 weeks. After 6 weeks, the callus was separated from the explants and placed on the callus proliferation media as described above and as shown in Medium XXVII (Table 1). However, after initiation, the callus proliferated and established very rapidly. Newly formed cells were isolated from the surface of the callus and subcultured to fresh medium at two week intervals. Rapidly growing cell lines showing a pale yellow to light brown color were selected for subculture.

After establishing the cocoa callus, it was necessary to test the effect of lower amounts of auxin on the sustainability of the callus because the high auxin content in medium XXVII was retarding cell growth and formed very brown callus in subsequent generations, indicating that the cells were experiencing stress. Various media were tested for their ability to sustain the cocoa callus as well as the downstream effect of the maintenance medium on cell suspension creation. Medium XXVII had 6 mg/L of auxins (2 mg/L IAA and 4 mg/L IBA), 2×MS vitamins and 250 mg/L of glutamine supplemented on to MS medium with 20 g/L of glucose and 7 g/L agar. For maintenance, the auxin in the medium was reduced to 4 mg/L (2 mg/L IAA and 2 mg/L IBA, medium XXVIII in Table 1) and 2 mg/L auxin in the form of IBA (medium XXIX in Table 1).

Reducing the auxin to 4 mg/L improved the color of the callus from dark brown to light brown through yellow. The callus cell growth was back up to vigorous levels. Cell suspension cultures were established with the same ease as those established from healthy callus subcultured on medium XXVII.

In medium with 2 mg/L auxin the color of the callus changed and the cell growth was back up to vigorous levels. However, when these calli were subcultured onto the same medium, the cell growth of callus was reduced, compared to callus on medium)(XVIII. After reducing the auxin to 2 mg/L, the effect of removal of extra MS vitamins (Medium XXX in Table 1) in conjunction with removal of glutamine (Medium XXXI in Table 1) on growth was also recorded. Callus from these two media did not look different in growth characteristics from callus on medium XXIX. However, it was noticed that the presence of the extra vitamins in the medium was advantageous in terms of production of procyanidin. The best medium for maintaining the cocoa vegetative callus was medium XXVIII as this allowed for long term sustainability of callus as well as allowing easy establishment of cell suspension and maintenance of procyanidin productivity.

Example 3

*Theobroma grandiflorum* and *Theobroma obovatum* Callus Induction and Proliferation Callus cultures of *Theobroma grandiflorum* and *Theobroma obovatum* are established using methods such as those described in Examples 1 and 2 for *Theobroma cacao*.

Example 4

Suspension Initiation

Cell suspension cultures were established by inoculating white fresh calli raised from floral explants described in Example 1 into 125 ml Erlenmeyer flasks containing 25 ml of 20 different kinds of liquid media (Medium IV-XXIII; Table 1). The flasks were covered with silicone foam caps and agitated at 120 rpm with gyratory shaking in a thermostatically controlled room at 24±1° C. under complete darkness for 54 days. The subcultures were transferred weekly or biweekly as deemed necessary. Cultures that formed as either granular or fine suspension of cells were retained, while cultures that did not form suspension cultures were discarded. After 14 days of cell growth, 10% (v/v) of the cells were transferred into new 125 ml flasks containing 25 ml of fresh medium and were thereafter subcultured biweekly. Medium VIII showed the best performance (45% PCV at day 14) of cell propagation in suspended cell initiation.

Figure 2A:
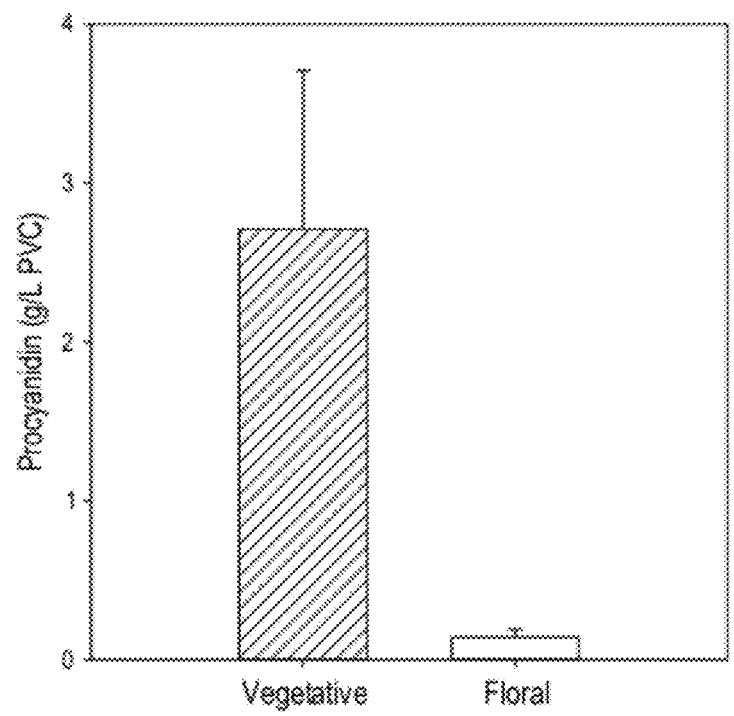
FIGS. 2A-2E includes a series of graphs showing procyanidin productivity and yield and carbohydrate consumption in *Theobroma cacao* cell cultures.
Figure 2B:
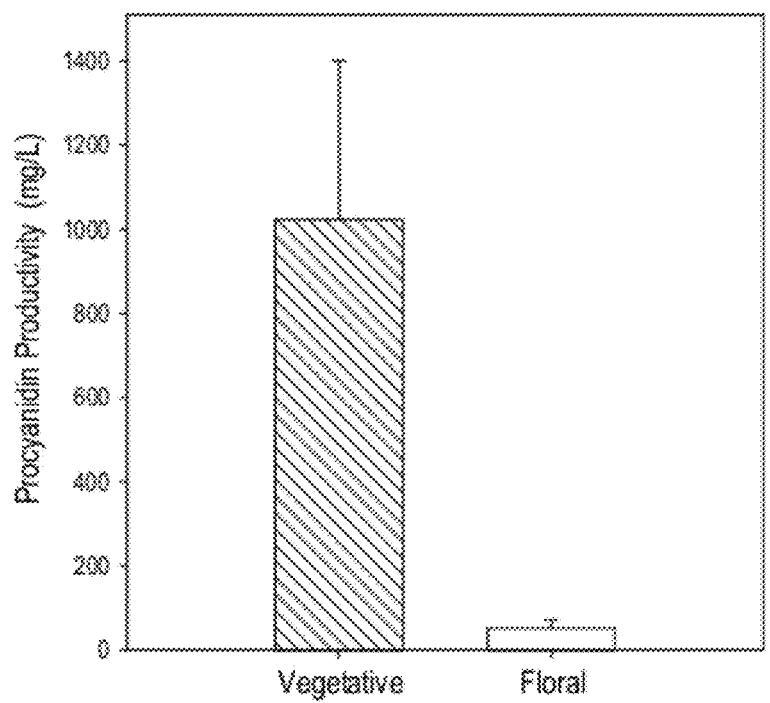

For raising suspensions of non-floral (vegetative) tissue (node, internode, young leaves, mature leaves), calli generated in Example 2 were transferred to liquid medium in a manner similar to that described above for floral explants. The medium used was Medium XXIV, which differs from the regular maintenance Medium VIII in terms of the type of salts (MS salts, rather than DKW salts, which contain more ammonium and nitrogen source and lower sulfate), includes 2 mg/L IAA and 4 mg/L IBA as auxins instead of 2,4-D and twice the strength MS vitamins (Table 1). This medium is similar to the solid medium in which the vegetative tissue were initiated, Medium XXVIII but without the gelling agent agar. In this medium, suspension cultures were established faster and the calli consumed all the sugar in the medium in seven days, whereas it takes usually 2 to 3 weeks for calli initiated in Medium VIII to consume the entire carbohydrate source. The procyanidin productivity of these established suspensions of non-floral tissue was also higher than that of the suspensions raised from floral tissue (1.1 g of total procyanidin/L of culture) (FIGS. 2A-2B).

Example 5

Figure 3:
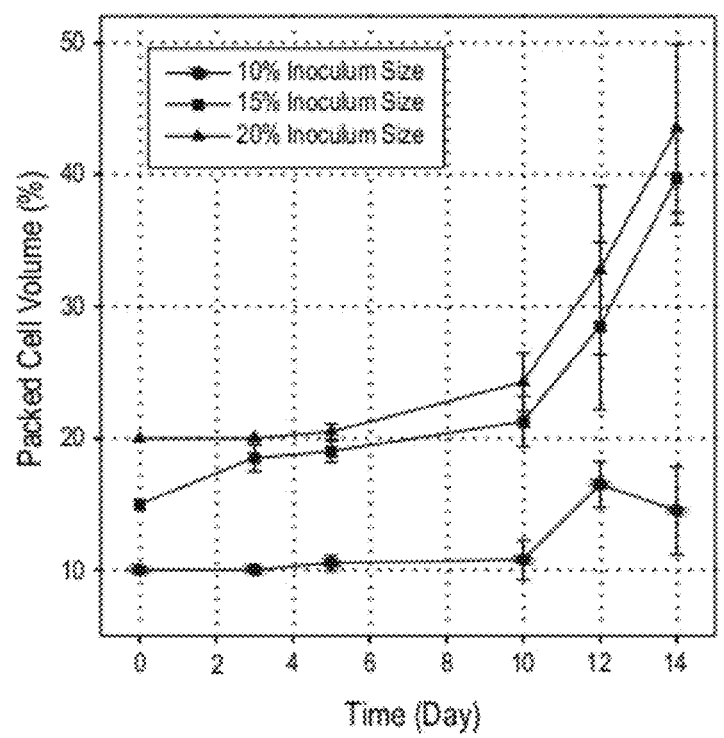
FIG. 3 includes a graph showing typical time courses of biomass density in cultures of various inoculum densities.

Cell Growth, Cell Selection and Medium Optimization of Floral Tissue-derived Suspension Cell Culture This example describes methods used to increase cell growth of suspensions. Cell culture productivity increases as a function of the rate of cell growth and the density at which cell growth stops. To determine the optimal inoculation density, suspension cultures of *Theobroma cacao* cells were initiated with a starting cell density of 10, 15 and 20% (v/v) and allowed to grow for 14 days. FIG. 3 shows typical time courses of biomass density as a function of inoculum density. Cultures initiated at a cell density of 10% showed a significant lag in growth and did not reach maximal density within 14 days. Cultures initiated at a cell density of 15% and 20% in Medium VIII doubled in density within 13 days and reached a maximal average cell density of 40-43% within 14 days. However, some cultures showed over 50-60% packed cell volume (PCV) at day 14 after the cell selection process.

Medium VIII and Medium I are identical recipes except that Medium VIII does not contain Phytagel. Both these media are based on DKW salts and vitamins prepared using several stock solutions which could lead to batch to batch variation in media components. Thus, Medium XXXII was created using premixed DKW basal salts (Phytotechnology Laboratories, LLC, Catalogue # D190) and suspension cell growth was compared between media VIII and XXXII. There were no significant differences in growth of cells in either media. Thus, Medium XXXII was routinely used for the maintenance of suspension cultures from floral tissue.

Biomass increase, sugar consumption, and procyanidin productivity were measured every seven days of culture. These data are very important for desirable cell selection process. Well-growing cells were preferentially selected based on PCV and sugar consumption measurements, and well-producing cell lines were then chosen among the well-growing cell lines based on procyanidin production yield. Higher biomass and higher procyanidin production yield can increase productivity in a batch cycle. Average procyanidin productivity before the cell selection process was 52 mg of procyanidin/L of culture, which improved up to the level of 251 mg/L after one year of the cell selection process, and the highest level achieved was 1.6 mg of procyanidin per liter of culture. The highest production yield increased to over 5.0 g/L of PCV as well.

Medium XXV was developed using B5 major salts and MS minor salts, thus lowering the concentration of ammonium ions in the medium compared to the usual maintenance medium of Medium VIII. Carbohydrate source was 60 g/L sucrose and hormones were 0.1 mg/L NAA and 0.2 mg/L kinetin, compared to 2 mg/L 2,4-D and 0.005 mg/L TDZ. Over the course of 2 weeks, the suspension tested in Medium XXV showed no growth, but procyanidins accumulated in the suspension to levels 4 times greater than in the control Medium VIII (over 95 mg/L with Medium XXV, compared to 22 mg/L with Medium VIII). This could be due to the higher ratio of nitrate/ammonium ions in this medium, coupled with an excess of cytokinin, compared to auxin.

Medium XXVI was developed with MS salts, 30 g/L sucrose, and 2,4-D at 1.5 mg/L. Suspension cultures transferred in this medium showed a higher accumulation of procyanidin to levels 4 times greater at day 13 than in the control Medium VIII (87 mg/L of procyanidin with Medium XXVI, compared to 22 mg/L with Medium VIII). Whereas cell growth is relatively similar between the two media (61% PCV from 22% PCV in Medium VIII, compared to 60% PCV to 25% PCV in Medium XXVI), sugar consumption was different, indicating the cells would prefer glucose as carbohydrate source.

Similar studies are performed with *Theobroma grandiflorum* and *Theobroma obovatum*. Cell culture productivity increases as function of the rate of cell growth and the density at which cell growth stops. To determine the optimal inoculation density, suspension cultures of *Theobroma grandiflorum* and *Theobroma obovatum* cells are initiated with a starting cell density of 10, 15 and 20% (v/v) and allowed to grow for 14 days.

In general, cultures initiated at a higher density have a shorter growth period or reach maximum cell density earlier. Cultures initiated at a cell density of 10% show a significant lag in growth and do not reach maximal densities within 14 days. Cultures initiated at a cell density of 15% and 20% double in density within 13 days and reach a maximal cell density of 40-43% within 14 days. This growth rate is slower than that reported previously for other plant cell suspension cultures, such as *Taxus* sp. However, cell growth of *Theobroma* cell cultures may be increased by further optimization of the growth medium and rigorous cell selection as described in Example 6, below.

Example 6

Cell Growth, Cell Selection and Medium Optimization of Vegetative Tissue-Derived Suspension Cell Culture Biomass increase, sugar consumption, and procyanidin productivity were measured every seven days of culture. These data are very important for desirable cell selection process. Well-growing cells were preferentially selected based on PCV and sugar consumption measurements, and well-producing cell lines were then chosen among the well-growing cell lines based on procyanidin production yield. Higher biomass and higher procyanidin production yield can increase productivity in a batch cycle. Newly created cell suspension cultures are normally a heterogeneous mixture of cells. This heterogeneity results in unbalanced cell growth and unstable production pattern of desired metabolites in large-scale suspension cultures. Homogeneous cell cultures that are appropriate for large scale production can be derived from these heterogeneous mixtures by subculturing and selecting cultures with the desired characteristics. Selective and rapid screens were developed to detect polyphenols and cell growth to assist in this process. Butanol-HCl hydrolysis method, described in Example 8 was used to monitor polyphenol accumulation and Packed Cell Volume (PC—V (%)=cell volume×100/total culture volume) was employed as a measure of biomass. The rate of carbohydrate consumption was measured by refractive index (Brix %) as a measure of cellular metabolism.

Vegetative tissue (nodes) derived suspension cultures were derived from calli as described in Examples 2 and 4. One well-growing cell line (MX1440-3496) was selected and grown in three different media that varied in the type of basal media (DKW salts versus MS medium) and types and amounts of hormones (Media XXXII, XXXIII and XXXIV in Table 1). Packed Cell Volume (PCV) in Media XXXII and XXXIV was just 33.7±4.7% and 25.7±4.0% on day 7, which showed slower growth than Medium XXXIII (47.6±6.6%). Cell growth rate is significantly important for maximizing the volumetric productivity in cell culture process. Medium XXXIII was also superior in carbohydrate consumption rate measured by refractive index (RI) of spent medium. Initial glucose concentration (2%) in Medium XXXIII was adjusted to 3%, since glucose consumption rate of MX1440-3496 cell line was retarded in the late exponential growth phase. Thus, Medium XXXV was chosen as maintenance medium for the further cell selection process of MX1440-3496 cell line.

Figure 4:
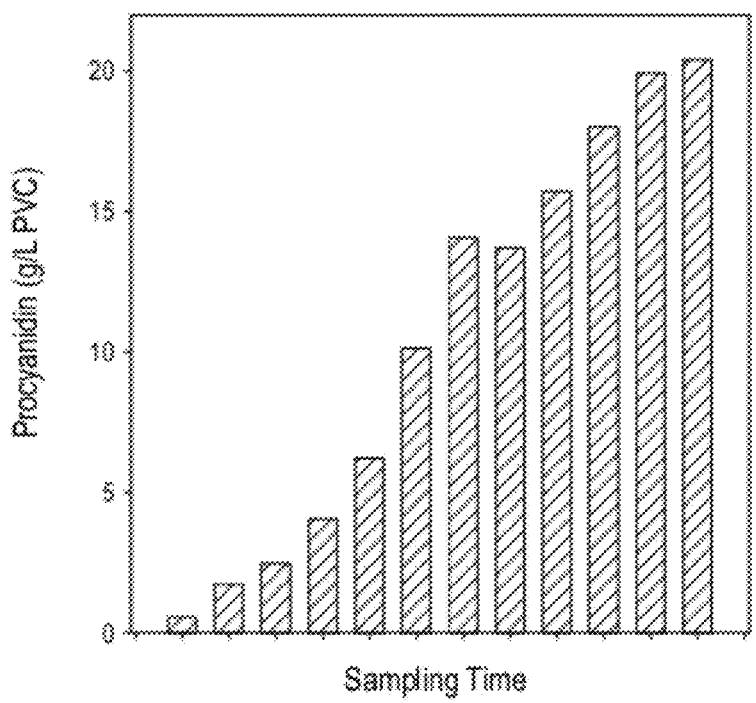
FIG. 4 includes a graph showing procyanidin production improvement over time due to cell selection process of cells derived from vegetative tissue.

Well-growing, fine cells that are not clumpy or forming aggregates were preferably selected at each subculture time to increase the volumetric productivity and eliminate aggregated cells, since selection of large or clumpy cell aggregates leads to poor culture performance. Therefore, the selected cells had mainly yellow-colored fine cell morphology and the fine suspension culture resulted in better growth and production of homogeneous suspension culture. The MX1440-3496 cell line initially grew at a doubling time of over 15 days, while the doubling time showed a decrease to 10 days after executing the cell selection process. Total procyanidin production level was initially 0.5 g/L PCV before the cell selection process, but increased by 20.4 times (10.2 g/L PCV) with the cell selection process (FIG. 4).

Example 7

Extraction of Polyphenols from Theobroma Callus Culture and Suspension Cultures

This example describes methods developed for extracting polyphenols from callus and suspension cells of Theobroma cultures developed in examples 1-4. Experiments in this example specifically used cultures of Theobroma cacao. Polyphenols were extracted from approximately 0.25±0.04 g fresh weight of calli with 1.5 ml 50% (v/v) ethanol including 0.1% $H_2SO_4$, and 0.1±0.003 g dried weight of suspended cells (no supernatant medium) with 1.5 ml 80% (v/v) methanol including 0.1% $H_2SO_4$. The cells were placed in a micro-centrifuge tube (2.0 ml) and homogenized with a bead mill homogenizer for 1 minute. The homogenates were centrifuged at 3500 rpm for 20 minutes and only the supernatants were moved to another micro-centrifuge tube.

When large numbers of suspended cell cultures needed to be screened, a more robust high throughput method was used as follows: From each flask of cell culture to be analyzed, 1 ml was aliquoted into a 96-deep well plate. The packed cell volume (PCV) of the sample was also recorded prior to transfer to the 96-deep well plate. Cells in each well were pelleted by centrifuging the plate at 6000 rpm for 4 minutes in a bench top centrifuge. The supernatant from each well was removed and discarded with a plastic transfer pipette. Next, 0.5 ml of extraction solvent (80:20 methanol:water) and a tungsten carbide bead were added to each well, and the plate was placed on a Mixer Mill to grind the cells at 15 Hz for 2 minutes. The plate was then transferred to the centrifuge and cell debris was pelleted by centrifugation at 6000 rpm for 4 minutes.

Example 8

Preliminary Analysis of Polyphenol Production in Culture

Figure 5A:
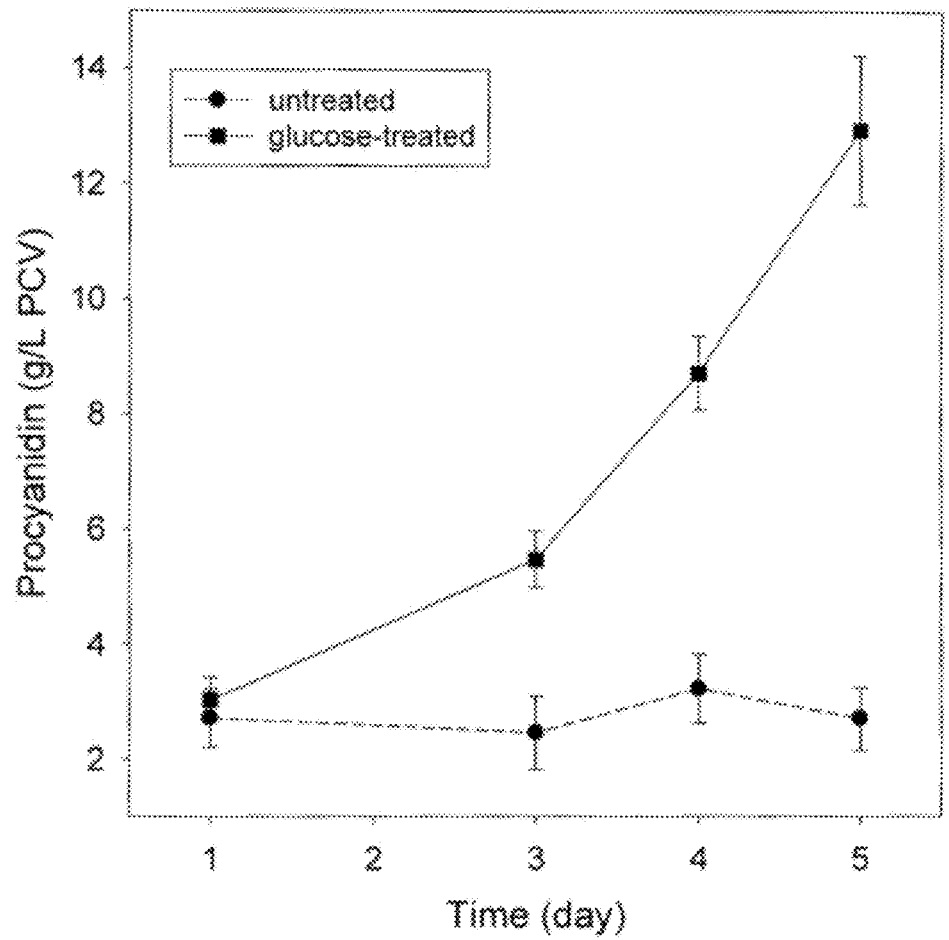
FIG. 5A includes a graph showing increased procyanidin production in response to incubation with glucose.

The method used to carry out the procyanidin analysis reaction was designed to approximate fairly closely the original Swain and Hillis (J. SCI. Food Agric. 10:63, 1959) method and Porter et al. (Phytochemistry, 25(1):223, 1986) method. The butanol-HCl extraction assay was used to measure polyphenols in the extracts of Theobroma cacao suspended cells. The polyphenols are hydrolyzed to the monomers of (−)-epicatechin and cyanidin by combining 0.1 ml of aqueous methanol extract and 1.0 ml of butanol-HCl reagent (95:5 v/v) and heating the solution at 75° C. for 60 minutes in a Qiagen deep well block (Valencia, Calif., USA). Presence of cyanidin in the hydrolyzed sample was observed by the formation of a pink color. The absorbance at 280 and 520 nm was determined, and procyanidin content was calculated based on the amount of cyanidin formed using a calibration curve created using different concentrations of procyanidin B2 purchased from Chromadex, Inc. (Irvine, Calif.). Brighter pink color indicated higher concentration of procyanidins in suspension cultures (FIG. 5A). Based on this method the procyanidin content of several suspension cultures ranged from 250 mg/L to 1000 mg/L.

Example 9

Figure 2C:
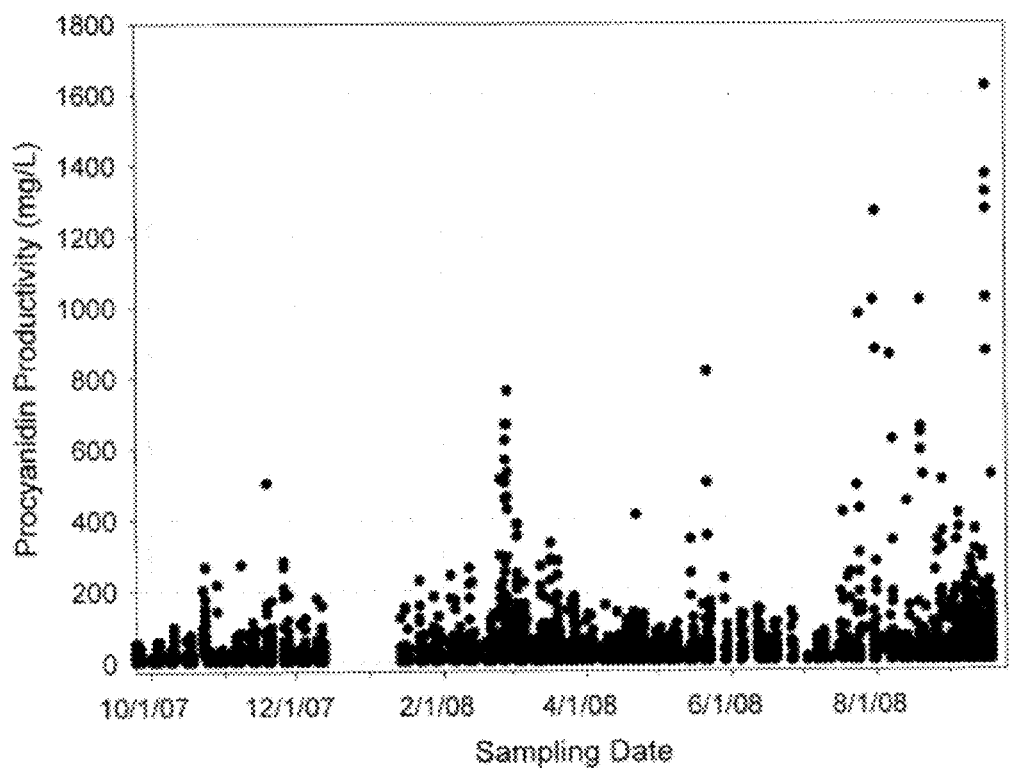
Figure 2D:
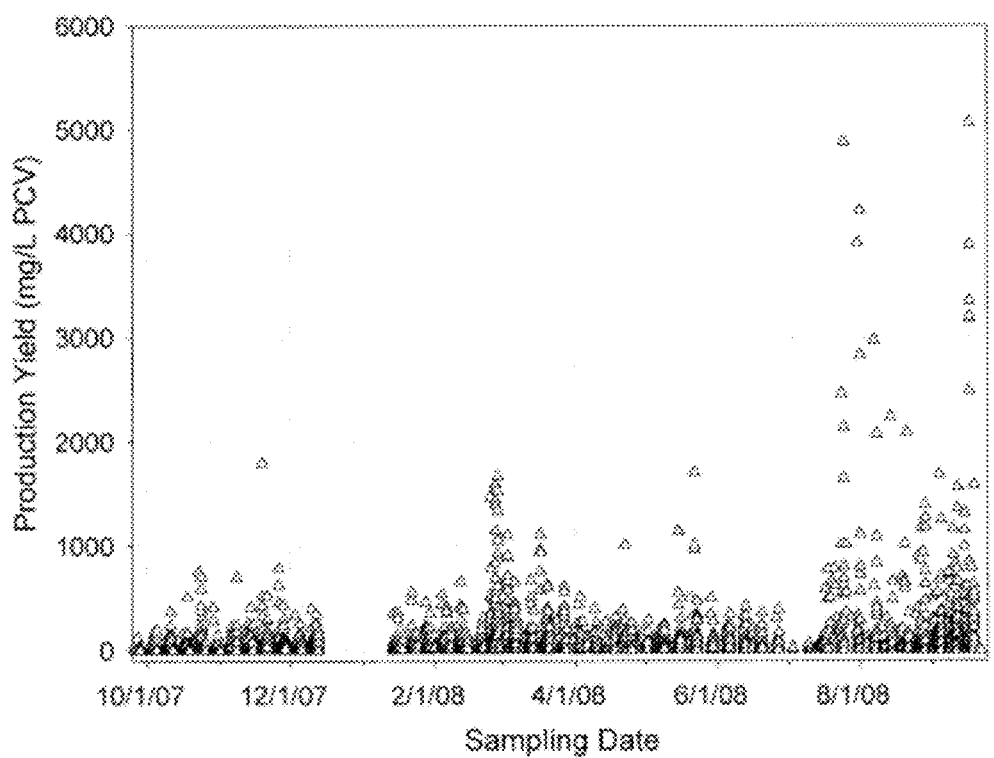

Cell Selection and Medium Optimization Process for Floral Derived Cell Suspensions Biomass increase, sugar consumption, and procyanidin productivity were measured every seven days of culture. These data are very important for desirable cell selection process. Well-growing cells were preferentially selected based on PCV and sugar consumption measurements, and well-producing cell lines were then chosen among the well-growing cell lines based on procyanidin production yield. Higher biomass and higher procyanidin production yield can increase productivity in a batch cycle. Average procyanidin productivity before the cell selection process was 52 mg of procyanidin/L of culture, which improved up to the level of 251 mg/L after one year of the cell selection process, and the highest level achieved was 1600 mg of procyanidin per liter of culture (FIG. 2C). The highest production yield increased to over 5000 mg/L of PCV as well (FIG. 2D).

Medium XXV was developed using B5 major salts and MS minor salts, thus lowering the concentration of ammonium ions in the medium compared to the usual maintenance medium of Medium VIII. Carbohydrate source was 60 g/L sucrose and hormones were 0.1 mg/L NAA and 0.2 mg/L kinetin, compared to 2 mg/L 2,4-D and 0.005 mg/L TDZ. Over the course of 2 weeks, the suspension tested in Medium XXV showed no growth, but procyanidins accumulated in the suspension to levels 4 times greater than in the control Medium VIII (over 95 mg/L with Medium XXV, compared to 22 mg/L with Medium VIII). This could be due to the higher ratio of nitrate/ammonium ions in this medium, coupled with an excess of cytokinin, compared to auxin.

Figure 2E:
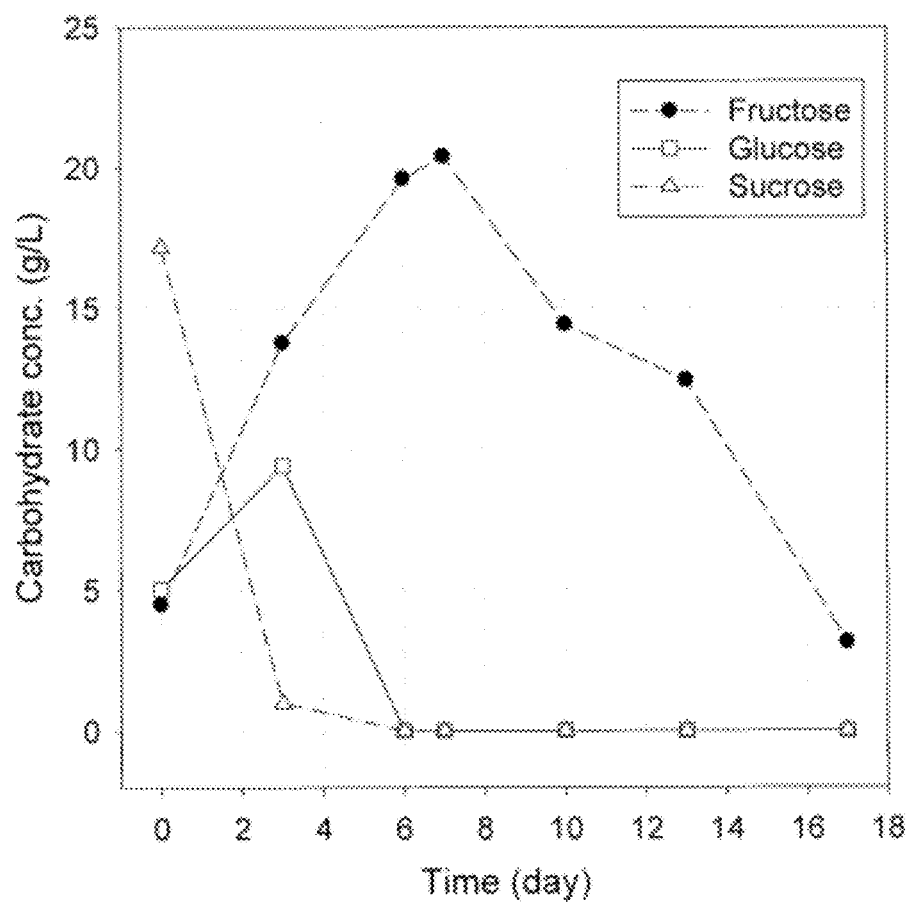

Medium XXVI was developed with MS salts, 30 g/L sucrose, and 2,4-D at 1.5 mg/L. Suspension cultures transferred in this medium showed a higher accumulation of procyanidin to levels 4 times greater at day 13 than in the control Medium VIII (87 mg/L of procyanidin with Medium XXVI, compared to 22 mg/L with Medium VIII). Whereas cell growth is relatively similar between the two media (61% PCV from 22% PCV in Medium VIII, compared to 60% PCV to 25% PCV in Medium XXVI), sugar consumption was different, indicating the cells would prefer glucose as carbohydrate source (FIG. 2E).

Example 10

Glucose Addition for Productivity Enhancement

This example describes the development of a protocol for increasing the procyanidin productivity of suspension cultures of cacao through supplemental addition of glucose.

Plant secondary metabolite production has been induced by changing medium from a growth medium to a production medium. For production medium optimization, either carbohydrate source or nitrogen source can be considered as critical factors. Additional carbohydrate in the form of glucose was used at the end of the exponential growth stage in order to enhance procyanidin production from floral and vegetative tissue-derived suspension cultures.

Significant improvements in procyanidin productivity were obtained from a floral tissue-derived suspension cell line (MX1241-58) by glucose addition. For 7 days, the culture was normally maintained in Medium XXXII under the normal cell culture condition as described in Example 5. MX1241-58 cell culture was sampled at day 7 before glucose addition and its PCV and RI were 49.5±3.5% and 0.2 on average. The average procyanidin production level was 189.5±17.7 mg/L PCV. At day 7, 5 ml of 50% glucose stock solution was added to the suspension culture to adjust RI to over 3% and was subsequently repeated when glucose concentration in medium was below 0.5%. After the glucose addition, the culture in the flask was shaken vigorously by hand for approximately 10 seconds to disperse the concentrated glucose in the suspension and the RI was measured again, which was 3 on average. With 3-4 times glucose addition at different culture days (at day 7, 11, 16 and 21) and one time fresh medium addition (day 25), procyanidin production level increased to up to 4.4 g/L PCV, which was 24 times higher than its initial value and PCV increased from 49.5±3.5% to 69.0±1.4%.

A similar treatment was applied to the cell line MX1440-3496 (described in Example 6) to improve its production level. This experiment was designed to test the cell line's response to glucose addition. MX1440-4496 cell line was maintained in Medium XXXIII, as described in Example 6. At day 6, 6 flasks of MX1440-3496 cell line were randomly chosen and divided into two sets of three flasks each. One set of three flasks were treated with a 50% glucose stock solution and the other 3 flasks were left untreated. The measurements prior to glucose addition for all six flasks on day 6 were, on average, 45% of PCV, 0.3±0.1 of RI and 2.41±0.19 g/L PCV of procyanidin production. 5 mL of 50% glucose stock solution was added to the three treated flasks. The average RI of the treated flasks after glucose addition increased to 6.0±1.1 and the average PCV was 39.7±0.6%.

All the flasks were sampled and their PCV, RI and procyanidin production were measured at day 1, 3, 4, 5 and 6 post glucose addition. The untreated flasks showed no significant change of RI and slight increase of PCV from 45% to 53±3.6%. Their production stayed at 2.83±1.17 g/L PCV at day 6 post treatment. In contrast, the treated flasks showed an increase in PCV to 53±2.7% at day 6, steadily increasing. RI dropped significantly at a rate of 0.6 to 0.8 units of RI per day, going from 6±1.1 at day 0 to 2.0±1.3 at day 6. Meanwhile, their production also increased from 2.42±1.93 g/L PCV prior to glucose addition to 12.93±2.24 g/L PCV at day 5. The glucose treatment resulted in increased procyanidin production and these production characteristics represent a significant improvement for a cell culture process for procyanidin production as shown in FIG. 5A.

Also, improvements in procyanidin productivity were obtained from MX1440-3496 cell line by glucose addition at 3%, 5%, and 6% glucose. This experiment was designed to test the cell line's response to glucose addition. MX1440-4496 cell line was maintained in Medium XXXV, as described in Example 6. At day 4, 12 flasks of MX1440-3496 cell line were randomly chosen and divided into four sets of three flasks each. Three sets were treated with varying concentrations (3%, 5%, and 6% by volume of culture medium) of glucose and the fourth set was left untreated. The concentration of glucose in each flask was verified by using the refractometer to check if the RIs were at 3, 5 and 6 respectively.

Figure 5B:
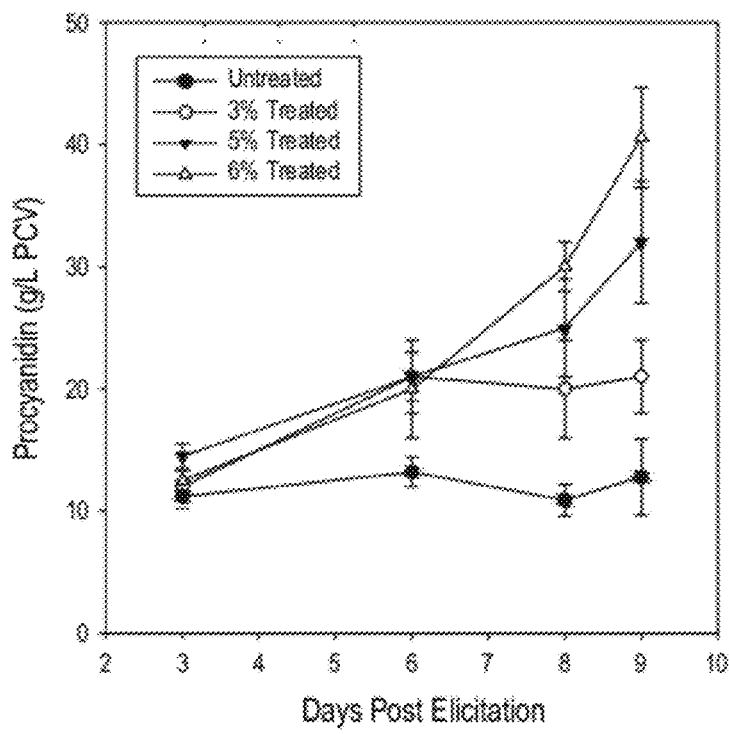
FIG. 5B includes a graph showing increased procyanidin production with various concentrations of glucose.

The measurements prior to glucose addition for all six flasks on day 4 were, on average, 45% of PCV, 0.7±0.1 of RI and 13.5±1.0 g/L PCV of procyanidin production. All the flasks were sampled and their PCV, RI and procyanidin production were measured at day 3, 6, 8 and 9 post glucose addition. The untreated flasks showed no significant change of RI and slight increase of PCV. Their production stayed at 12.8±3.1 g/L PCV at day 9 post treatment. In contrast, the treated flasks showed that RI dropped significantly at a rate of 0.7 units of RI per day, going down to 0.07±1.3 at day 9. Meanwhile, their production also increased steadily and especially 6% treated set showed dramatic increase from 13.5±1.0 g/L PCV prior to glucose addition to 40.6±4.12 g/L PCV at day at day 9 post treatment. The glucose treatment resulted in increased procyanidin production and these production characteristics represent a significant improvement for a cell culture process for procyanidin production as shown in FIG. 5B.

Figure 6:
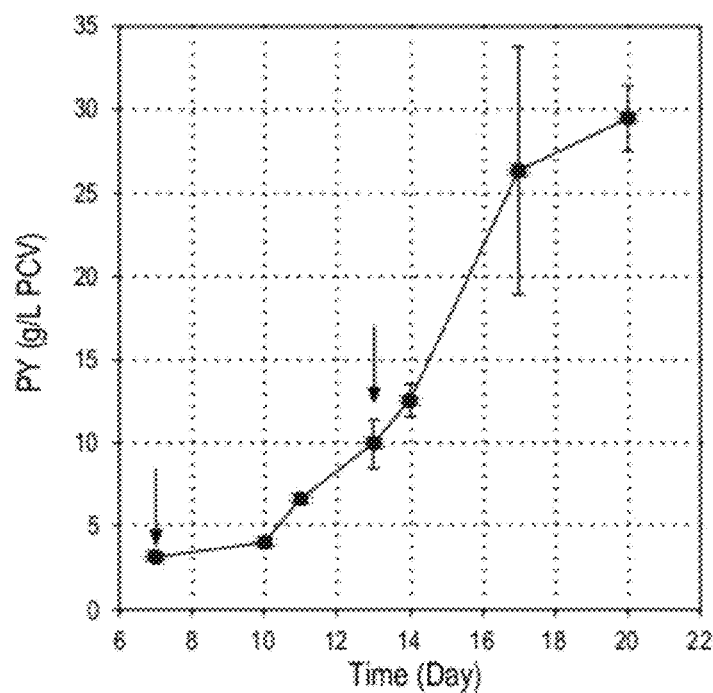
FIG. 6 includes a graph showing procyanidin production enhancement over 2 elicitation events, in cell line MX1440-3496 due to supplemental glucose addition.

Another method for boosting procyanidin production in suspension culture was repeated elicitation. At day 7 and 13, glucose was added to culture medium and their RI was increased up to 6% Brix. The repeated elicitation made the suspended cells produce procyanidin compounds steadily. Prior to the first elicitation, procyanidin production was 3.2±0.1 g/L PCV, but it was improved to 12.6±1.3 g/L PCV at day 13 and 29.5±2.8 g/L PCV at day 20. The repeated addition of glucose provided a simple and effective approach to enhancing procyanidin production by cocoa suspended cell culture, as shown in FIG. 6 where the arrows show the dosing with glucose.

Repetitive cell selection at every subculture time collected well-growing and well-producing cells and then the initial 3% glucose concentration in medium XXXV became limited from day 4~5. It provided very serious stress to the cells and they began to be more aggregated in suspension culture. Typically aggregation can be a hindrance to process scale-up to large scale production systems. Therefore, the initial glucose concentration of 3% was increased up to 4% (medium) (XXVII) in order not to give any stress from carbohydrate limitation. The 4% glucose concentration made the cell line maintenance more stable without aggregation phenomena in the flask suspension culture as well as bioreactor culture.

Example 11

Culturing Cells in Hormone Free Medium and Elicitation of these Cells

Figure 7A:
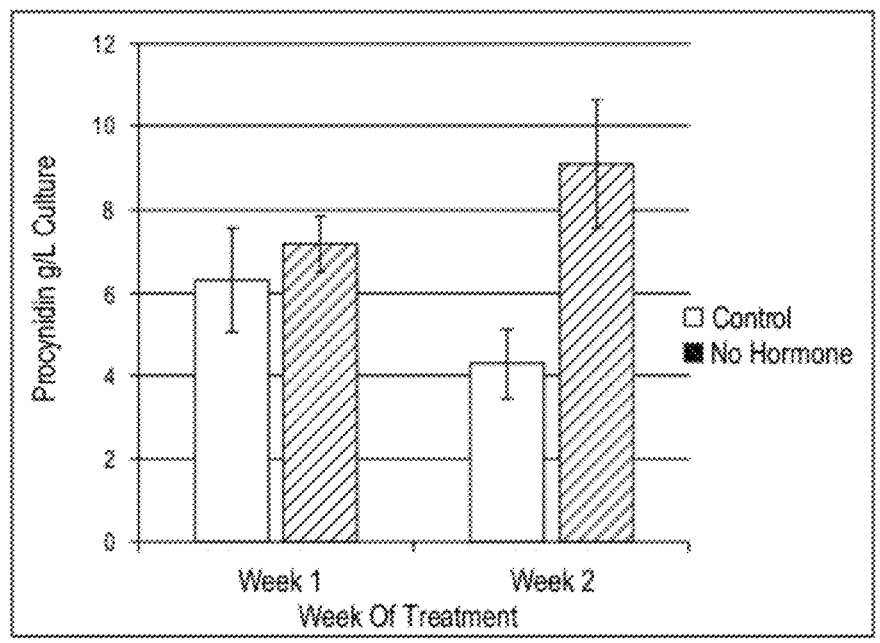
FIG. 7A includes a graph showing an increase of procyanidin production per liter culture after removal of hormones for 2 consecutive weeks.

This example describes the growth of cells and production of procyanidin in medium devoid of hormones for 2 consecutive weeks. Cells produced by the methods in Examples 2 and 4 were cultured for 2 consecutive weeks in Medium XXXVI (Table 1). This medium had no hormones added to the base medium, Medium XXXV (Table 1). Initial inoculum was set at 25%. The cells were allowed to grow in hormone free medium for 7 days and subcultured for a second time in hormone free medium for another period of 7 days. Growth and production data were recorded on the $6^{th}$ day of transferring into fresh medium. It was seen that growth of cells was reduced by 10-15% from 45-50%% to 35-40%. However, the production per liter PCV had increased 2.5-3 times compared to control cells. The total volumetric productivity was at ~2-2.5 times that of the control cells. This shows the ability to maintain productivity after removal of hormones from the culture as shown in FIG. 7A. This is a significant achievement in terms of processing as removal of hormones from the final weeks of production is a great advantage from a regulatory standpoint.

Figure 7B:
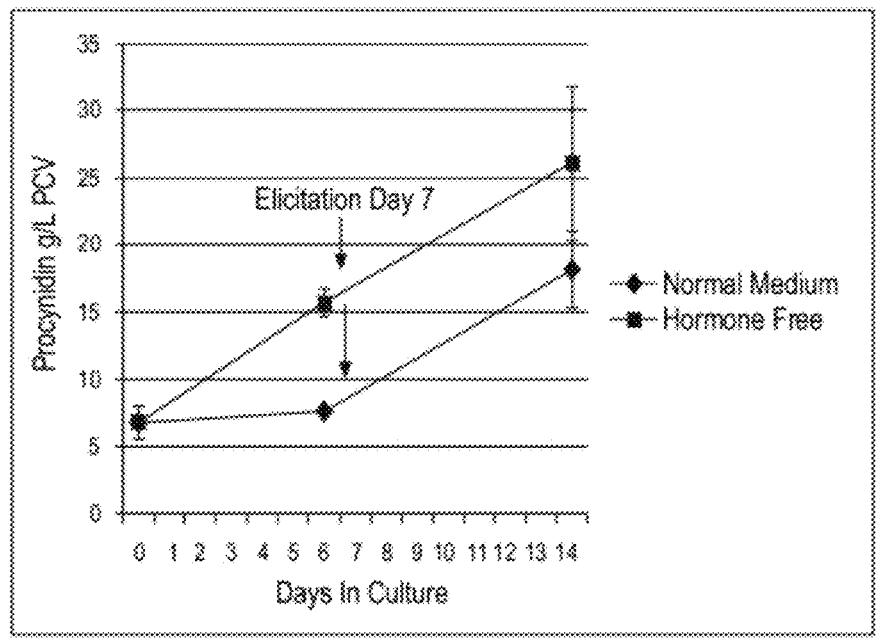
FIG. 7B includes a graph showing the additive effect of two treatments: removal of hormone for 1 week and then a second treatment of elicitation of the cells with 6% glucose for 1 week, where the elicitation is 7 days after the removal of hormone from the media.

The feasibility of a synergistic effect of growing cells in a hormone free medium with glucose elicitation was tested. Cells were grown in hormone free medium TC3015 for 1 week. On day 7 of the culture, both control and treated cells were at RI between 0-0.6 from an original of 3.0. At this time, the cells were dosed with 6% glucose and left to grow for 7 additional days. Samples were taken on days 0 and 7 of elicitation. It was seen that there was an additive effect of removal of hormones and the glucose elicitation. The production per liter PCV increased by ~2.5 fold in the control cells that were just treated with elicitation whereas, in the cells that were treated with both hormone free medium and an addition of elicitor (e.g., glucose), the fold change was ~4 fold. The removal of hormones increased the production by nearly 2 fold and then a further 2 fold increase was seen after elicitation of these cells, hence, there was a clear additive effect of the two treatments together (FIG. 7B).

Example 12

Small Scale Extraction of Polyphenols from Fresh Cocoa Cells or Ground Freeze Dried Cells Cocoa cells (0.5 mL) without media or 50 mg of ground cocoa cells were sampled in 2.0 ml of micro-tubes or 1.2 ml tubes in a 96 well block from Qiagen, Inc. Appropriate volumes of acidic (0-2% of citric, acetic or ascorbic) aqueous extraction solvent (30-80% of acetone, ethanol, methanol) was added to each of the cocoa cells and then placed into ultrasonicator or BeadMill to extract procyanidins. The samples were centrifuged for 4 minutes at 6000 rpm (RCF 5996). The supernatant may be filtered with 0.45 um membrane filter and diluted to 10× (if necessary) by using the same aqueous extraction solvents prior to analysis. The leftover extracts were stored in –20 degree of freezer for further analyses. FIG. 12 illustrates the results from various solvent systems.

Example 13

Analysis of Polyphenols from *Theobroma cacao* Callus and Suspension Cells

Figure 8C:
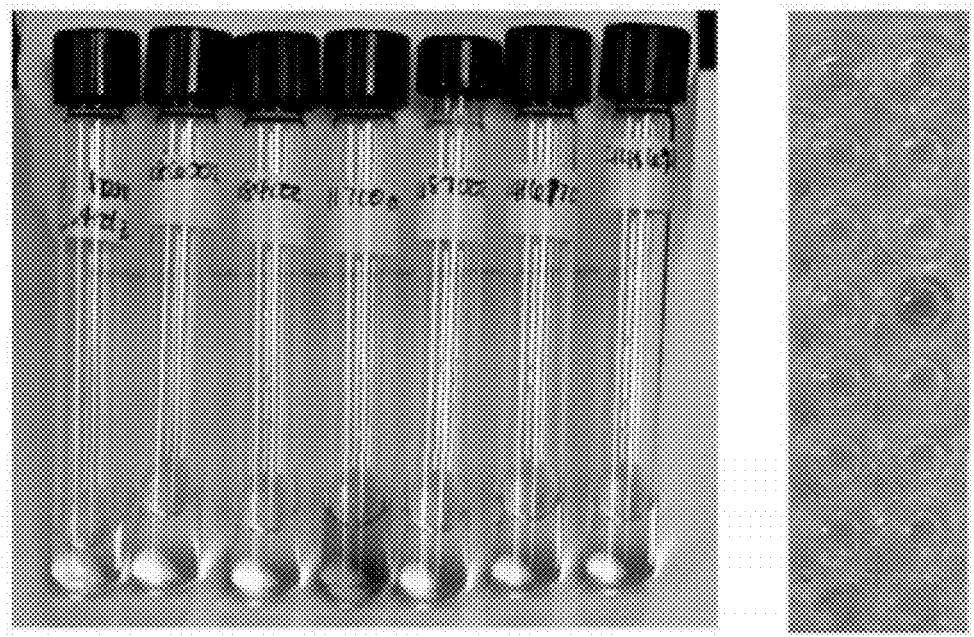

The method used to carry out the procyanidin analysis reaction was designed to approximate the original Swain and Hillis (*J. SCI. Food Agric.* 10:63, 1959) method and Porter et al. (*Phytochemistry*, 25(1):223, 1986) method. The butanol-HCl hydrolysis assay was used to measure procyanidins in the extracts of *Theobroma cacao* cells. The procyanidins are hydrolyzed to the monomers of (−)-epicatechin and cyanidin by combining 0.1 ml of aqueous ethanol, methanol or acetone extract and 1.0 ml of butanol-hydrochloric acid reagent (95:5 v/v) and heating the solution at 75° C. for 60 minutes in a Qiagen deep well block (Valencia, Calif., USA). Presence of cyanidin in the hydrolyzed sample was observed by the formation of a red color. The absorbance at 280 and 520 nm was determined spectrophotometrically, and procyanidin content was calculated based on the amount of cyanidin formed using a calibration curve created using different concentrations of procyanidin B2 purchased from Chromadex, Inc. (Irvine, Calif.). Darker red color indicated higher concentration of procyanidins in callus or suspension cultures (FIGS. 8A-8C).

Figure 9A:
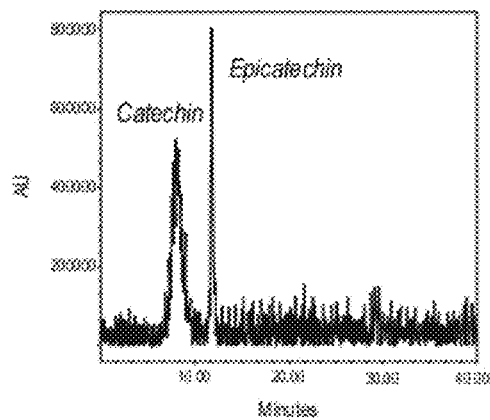
FIGS. 9A-9F include a series of chromatographs for procyanidins and alkaloids from *Theobroma cacao* cell cultures.
Figure 9D:
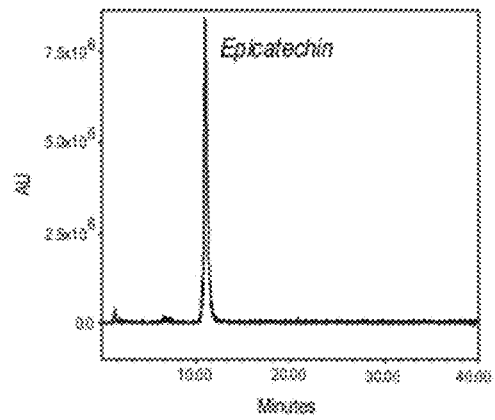
Figure 9B:
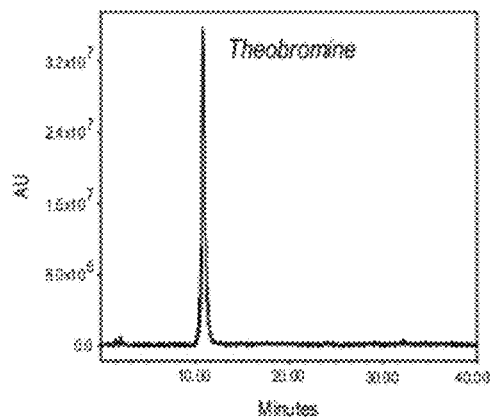
Figure 9E:
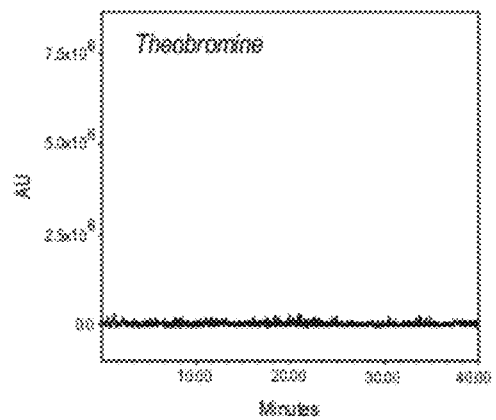
Figure 9C:
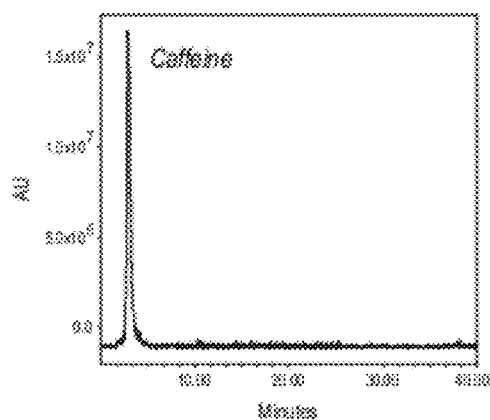

LC analyses were performed on the *Theobroma cacao* cell extracts using a Waters (Milford, Mass., USA) Alliance HPLC system equipped with a CTC Analytics PAL autosampler (Leap Technologies, Carrboro, N.C., USA), Waters 626 pump with 600S Controller and a Waters 2996 photodiode-array detector (PDA) scanning from 190 to 780 nm. Gradient elution was carried out with water-0.1% formic acid (solvent A) and acetonitrile-0.1% formic acid (solvent B) at a constant flow-rate of 0.3 ml/minute. A linear gradient with the following proportions (v/v) of solvent B was applied (t(min), % B): (0, 7), (5, 15), (20, 75), (25, 100), (35, 100), (35.1, 7) (45, 7). The column was Ultra Aqueous C18 column (100×2.1 mm i.d., 3.5 µm) (Restek, Bellefonte, Pa. USA). The procyanidin monomers of (+)-catechin, (−)-epicatechin, and oligomeric procyanidins (dimer to hexamer) were monitored at 280 nm. A Waters Quattro Micro triplequadrupole mass detector (Milford, Mass., USA) was used to obtain the MS data and analyzed by MassLynx™ software. Full-scan data acquisition was performed, scanning from m/z 150 to 1800. Authentic standards for catechin, epicatechin, were purchased from Sigma-Aldrich, Inc. (St. Louis, Mo.) and dilutions made to create calibration curves in order to detect and quantify the metabolites. (FIGS. 9A to 9C).

Total polyphenol content of cell extracts was measured using the Folin-Ciocalteau assay (waterhouse.ucdavis.edu/phenol/folinmicro website; and Slinkard, K.; Singleton, V. L. Total Phenol Analysis: Automation and Comparison with Manual Methods. *American Journal of Enology and Viticulture* 1977, 28: 49-55). Cell culture extracts, as described in Example #9, were analyzed for total polyphenol content by taking 20 µl extract and adding it to 1.58 ml of water plus 100 µl of Folin-Ciocalteau reagent. The reaction is then stopped by the addition of 300 µl sodium carbonate solution. The resulting solution is measured at 765 nm and compared to a calibration curve of various dilutions of gallic acid solution measured by the same assay to determine the concentration of total polyphenols in the cell extracts.

Figure 10A:
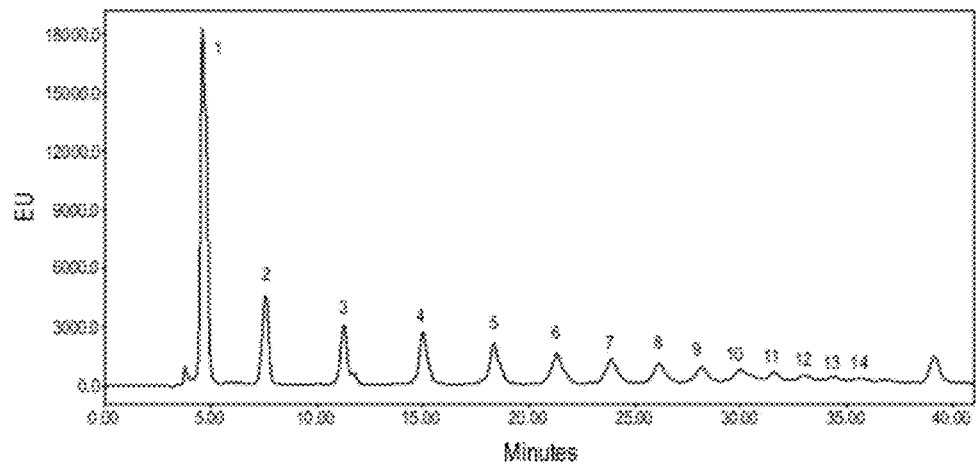
FIGS. 10A-10B include graphs that illustrate a series of HPLC chromatograms of suspension cell extract: in fluorescence detector mode (FIG. 10A); or in PDA detector mode at 280 nm (FIG. 10B). The labels 1 through 12 indicate the degree of polymerization of procyanidins, respectively: 1, monomers; 2, dimers; 3, trimers; 4, tetramers; 5, pentamers; 6, hexamers; 7, heptamers; 8, octamers; 9, nonamers; 10, decamers; 11, undecamers; 12, dodecamers.
Figure 10B:
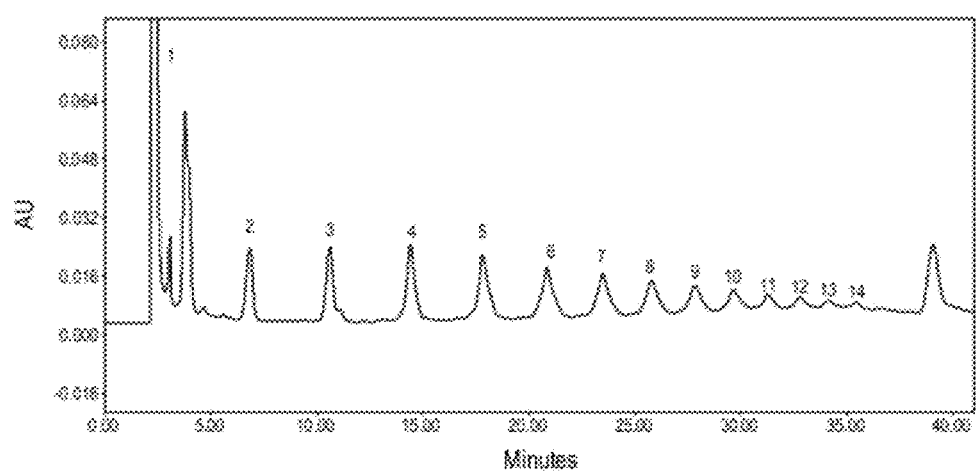

Analysis of quantifiable procyanidins was performed by normal phase HPLC system consisted of the Waters 2795 separation module, the Waters 996 PDA detector and the Waters 474 scanning fluorescence detector. Characterization and separation conditions of procyanidins in cocoa cell extracts obtained using Develosil Diol (250×4.6 mm ID, 5µ particle size) adapted from Kelm et al., the improved process for analyzing for separating, and for isolating polar protic monomers and/or oligomers. (U.S. Pat. No. 0,075,020). The binary mobile phase consist of solvent (A), acetonitrile:acetic acid (98:2, v/v) and solvent (B), methanol:water:acetic acid (95:3:2, v/v/v). A linear gradient elution was performed at 30° C. with 0.8 mL/min flow rate as follows: 0-35 min, 100-60% A; 35-40 min, 60% A; 40-45 min, 60-100% A. Separations of oligomer procyanidins were monitored by fluorescence detection (excitation wavelength at 276 nm, emission wavelength at 316 nm), UV detection at 280 nm (FIG. 10A). (Lazarus et al. J. Agric. Food Chem. 47 (1999), 3693) and PDA (FIG. 10B).

The purpose of the analytical method is to quantify the amount of ten different individual procyanidins in fresh cocoa cells or freeze-dried cells. Quantifiable procyanidins are monomer, dimmers, trimers, tetramers, pentamers, hexamers, heptamers, octamers, nonamers and decamers.

The samples prepared from fresh cocoa cells, freeze-dried cocoa cells and cocoa cell extract were analyzed for procyanidin quantification by executing internal HPLC method on Empower 2. Calibration curves of oligomeric procyanidins are prepared using in-house standard stock solution. A set of standards were prepared at serial dilutions of 20, 40, 80, and 100 ug/ml using in-house purified standard compounds. These standard calibration curves are the basis for quantification of the 10 target compounds (monomers-decamers).

Example 14

Analysis of Theobromine and Caffeine

Figure 9F:
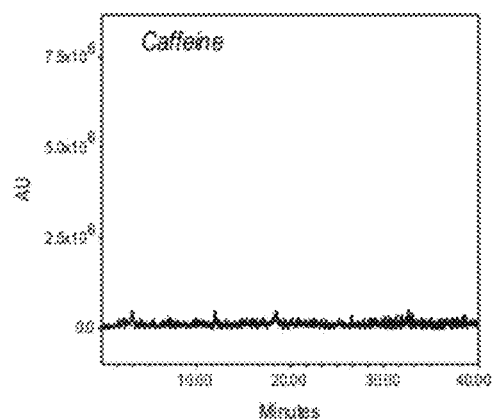

Using the LC/MS analysis method, the levels of theobromine and caffeine, the major alkaloids in individual defatted Theobroma cacao seeds, were determined to be 25.2 mg/g dry weight and 4.6 mg/g dry weight, respectively. In contrast, Theobroma cacao suspended cells did not produce measurable caffeine (FIGS. 9C and 9F) or theobromine (FIGS. 9B and 9E) while they produced catechin and epicatechin at levels comparable to the seeds (FIGS. 9A and 9D). Authentic standards for theobromine and caffeine were purchased from Sigma-Aldrich, Inc. (St. Louis, Mo.) and dilutions made to create calibration curves in order to detect and quantify those metabolites. These results demonstrate that plant cell cultures can produce high concentrations of the compound of interest with little contamination by unwanted compounds.

Figure 11:
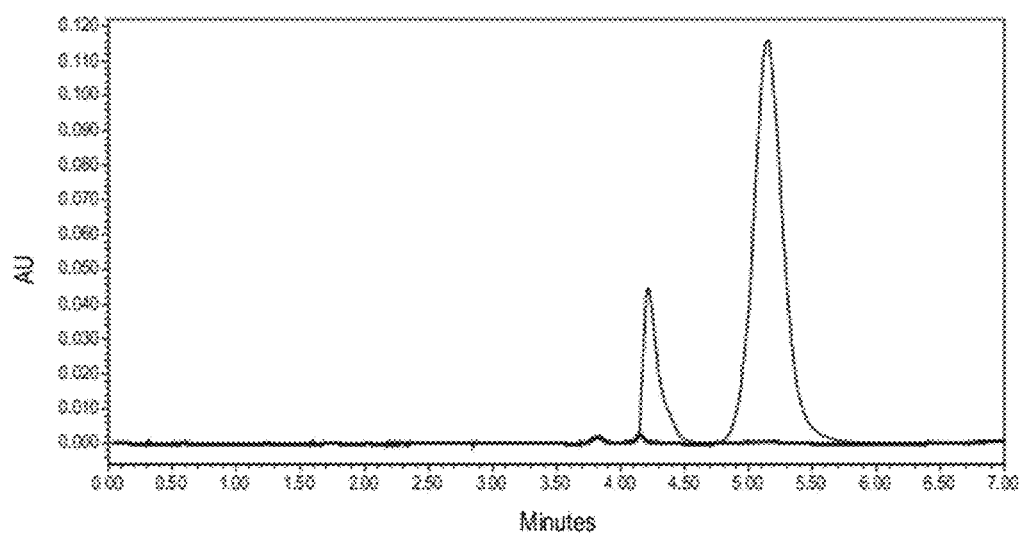
FIG. 11 includes a chromatogram comparing the concentrations of theobromine and caffeine in suspension cell extract and unfermented cocoa bean extract, showing trace amounts of the metabolites in suspension cell extract as opposed to the cocoa bean extract.

Quantifications of caffeine and theobromine were also performed on the Waters 2795 separation module consisting of the Waters 996 PDA detector (Milford, Mass.). Separation of caffeine and theobromine in cocoa cell extracts carried out on Develosil Diol (250×4.6 mm ID, 5μ, particle size, Phenomenex, Torrance, Calif.) using UV at 280 nm adapted from Kelm et al., (J. Agric. Food Chem., 2006, 54, 1571). The binary mobile phases consist of solvent (A), acetonitrile: acetic acid (98:2, v/v) and solvent (B), methanol:water:acetic acid (95:3:2, v/v/v). A linear gradient elution was performed at 30° C. with 0.8 mL/min flow rate as follows: 0-35 min, 100-60% A; 35-40 min, 60% A; 40-45 min, 60-100% A. Standard stock solutions of caffeine (Sigma Aldrich, St. Louis, Mo.) and theobromine (Sigma Aldrich, St. Louis, Mo.) were prepared using serial dilutions of 1, 10, 20, 50, 100, 200, and 500 ug/mL respectively. Samples were prepared in duplicates according the above-described in Example # for cocoa suspension cell and Example# for unfermented cocoa bean. All samples were injected in to the HPLC module after filtering through a 0.45 um membrane filter. Table 3 shows the determination of caffeine and theobromine in samples. Caffeine and theobromine were determined to be in range 0.27~0.49 ug/mg and 0.32~0.73 ug/mg in cocoa cell extract respectively and 14.1 ug/mg and 49.3 ug/mg in unfermented cocoa bean extract respectively. On the basis of the analyses of data, cocoa cells has substantially free of caffeine and theobromine than unfermented cocoa bean extract (FIG. 11). Accordingly, an extract composition can be considered to be substantially xanthine-alkaloid free when caffeine and theobromine are less than about 0.5 ug/mg and 0.75 ug/mg, respectively.

Example 15

Scale-Up of Cocoa Suspension Culture

A common problem in the use of plant cell cultures is obtaining consistent production of target products (Kim et al., Biotechnol Prog. 20(6) 1666, 2004). Therefore, a key for successful large-scale plant cell culture is to maintain stable productivity. A process to scale-up suspensions of cocoa cell cultures from 125 ml flasks to 500 ml flasks was successfully conducted, as cocoa cell growth and production were very consistent and stable under the scaled-up conditions. Average PCV of selected cell lines was 45~55% for seven days, which was about 2.5 times greater than the initial PCV level of 20%. Larger-scale flask cultures were grown in maintenance medium of Medium VIII on a gyratory shaker at 110 rpm for 125 ml and 500 ml Erlenmeyer flasks, and 50 rpm for 2800 ml Fernbach flasks, all under dark conditions. Every seven days of culture, biomass, sugar concentration in medium, and procyanidin productivity were measured 2.7 L of cacao cells were inoculated into a 6.5 L bioreactor (working volume=5.0 L) and cultivated for seven days under 0.2 vvm (volume of gas per volume of culture per minute) of air flow rate, 100 rpm agitation speed and 23° C. vessel temperature. Biomass increased very slowly and lag phase lasted four days. High inoculation volume was an issue for the cells because this could limit nutrient availability and also make it difficult for uniform mixing of the cells. Ideally starting inoculum volume should be between 25 and 40% PCV. One of the important factors that affects biomass concentration and specific productivity is the gas exchange of dissolved oxygen (DO) concentration and dissolved gaseous metabolites such as $CO_2$ (Dicosmo & Misawa, "Plant Cell Culture Secondary Metabolism", 1996, pp 44). In flask cultures, it is impossible to control the dissolved oxygen and gaseous metabolites, but controlling them in a reactor culture is feasible. In this example, DO level dropped gradually, which was a good indicator of cellular metabolism.

Example 16

Large-Scale Separation from Suspension Cell Cultures

The biomass recovered from 1 L of cocoa suspension cell was used as fresh cells or lyophilized to give 75.0 g of dried cocoa cells using Labconco freeze-dryer. The fresh cells or dried cocoa cell powder was extracted twice with either 1 L of $H_2O$ with 0.1%-2% of ascorbic acid, acetic acid, citric acid or 1 L of aqueous extraction solvents (30, 40, 50, 60, 70, 80% of acetone, 30, 40, 50, 60, 70 80% of methanol, or 30, 40, 50, 60, 70, 80% of ethanol in the presence of 0.1%-2% of ascorbic acid, acetic acid, citric acid for 1 hr at 0-80° C. using a shaker. The extraction solution was filtered using a Buchner funnel or centrifuged. The filtrates or supernatants were combined together and then evaporated by rotary evaporator under partial vacuum at 40° C. to final volume of 300 mL. The concentrated aqueous residue was frozen at −20° C. and dried out using Labconco freeze-dryer to give bright yellow crude extract. The yields of crude procyanidins from the dried cocoa cells weight determined by the HPLC quantification method in Example 10 ranged between 10-15%.

The lyophilized biomass recovered from 10 L of cocoa suspension cell cultures is mixed with 80% methanol at a ratio of 1:1 of the volume of biomass and stirred at room temperature for 1 hour. This is filtered under vacuum in a Buchner funnel through filter paper. Extraction is repeated at least three times. Each methanol extract is collected, pooled and concentrated at 40° C. under reduced pressure to reduce the volume of the methanol extract to 30% of original. The concentrated methanol extract is added to dichloromethane for liquid-liquid extraction and the dichloromethane layer extract is collected, pooled and concentrated at a ratio of 25% at room temperature under reduced pressure. The dried extract is dissolved in methanol, dropped into distilled water and left at 0° C. for two days to obtain precipitate.

The actual yield of pre-purified procyanidin from the dried cells ranges between 10~20% with 50~60% purity. For efficient removal of impurities, further purification is performed by Waters prep-LC (Milford, Mass., USA) using a C18 and a silica column and the purity will be increased up to over 99% after the prep-LC purification process. To obtain the target compound of procyanidin in high purity, the additional process of crystallization can be employed.

Example 17

Comparison of Polyphenols and Procyanidins Produced from Cell Cultures of Theobroma cacao and Cocoa Beans Extraction of Crude Proanthocyanidins from Suspension Cultures The biomass recovered from 1 L of Theobroma cacao suspension cell cultures was lyophilized to give 14.0 g of dried cacao cells using Labconco freeze-dryer. The dried powder was extracted with 250 mL of mixed aqueous acetone (70% v/v) for 30 minutes. The aqueous solution was centrifuged at 3500 rpm for 15 minutes and supernatant removed. The solid residue was extracted a second time in the same manner. The supernatants from the two extractions were combined together and then evaporated by rotary evaporator under partial vacuum at 40° C. The concentrated aqueous residue was frozen at −20° C. and dried using Laboconco freeze-dryer to give thick yellow crude extract. The yields of crude procyanidins from the dried cell weight were determined by the acid butanol hydrolysis method described in Example B and ranged between 10-15%.

Extraction of Crude Proanthocyanidins from Non-Fermented Raw Cocoa Beans

Unfermented raw cocoa beans were obtained from the Raw Harmony (Los Angeles, Calif.). Crude procyanidins were extracted from 5 g of ground dried, non-fermented beans or ground, defatted, non-fermented cocoa beans. Extraction was similar to the procedure used for suspension cell cultures described above except that 50 mL of aqueous acetone (70% v/v) was used for each extraction step and extraction was repeated three times. The combined extracts were centrifuged at 3500 rpm for 15 minutes. The supernatant was decanted and then evaporated to remove solvent under partial vacuum at 40° C. The concentrated aqueous residue was frozen at −20° C. and dried using Laboconco freeze-dryer to give reddish purple crude extract. The yields of crude procyanidins as estimated by the acid butanol hydrolysis assay described in Example 8 ranged between 10-13%.

High Performance Liquid Chromatography (HPLC) Analysis of Procyanidins

HPLC analysis of procyanidins was performed by normal phase HPLC system consisting of a Waters 2795 separation module, the Waters 996 PDA detector and the Waters 474 scanning fluorescence detector. Characterization and separation conditions of procyanidins in *Theobroma cacao* cell extract and raw cocoa bean extract obtained using Develosil Diol column (250×4.6 mm ID, 5μ particle size) adapted from Kelm et al. (U.S. Pat. Appl. No. 2007075020) which describes an improved process for polar protic monomers and/or oligomers. The binary mobile phase consists of solvent (A), acetonitrile:acetic acid (98:2, v/v) and solvent (B), methanol:water:acetic acid (95:3:2, v/v/v). A linear gradient elution was performed at 30° C. with 0.8 mL/min flow rate as follows: 0-35 minutes, 100-60% A; 35-40 minutes, 60% A; 40-45 minutes, 60-100% A. Separations of procyanidins was monitored by fluorescence detection (excitation wavelength at 276 nm, emission wavelength at 316 nm), UV detection at 280 nm. (Lazarus et al., *J. Agric. Food Chem.* 47: 3693, 1999).

Figure 8C:
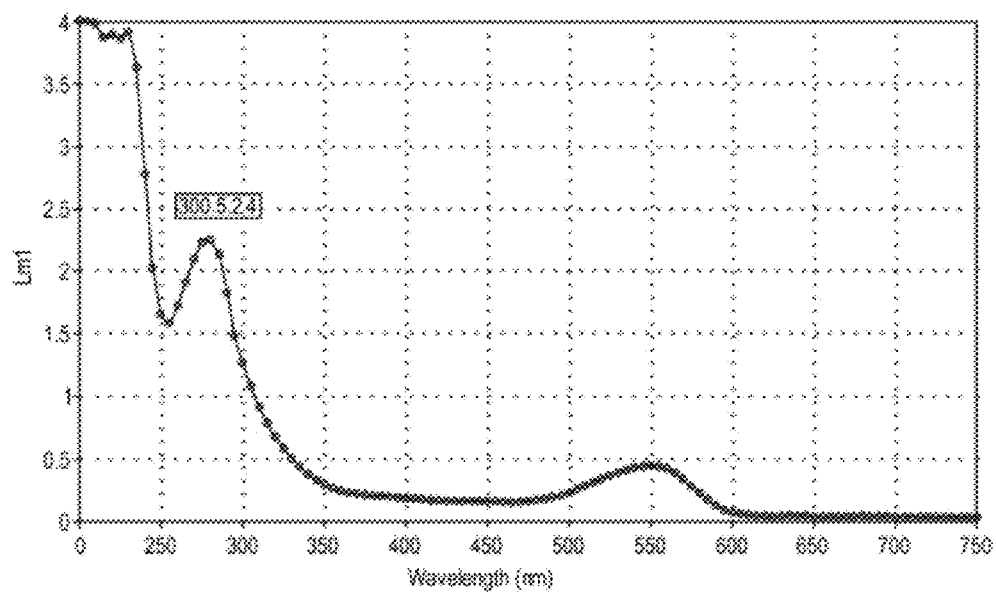

FIG. 8 shows chromatograms of unfermented cocoa bean extract (FIG. 8A) and *Theobroma cacao* cell suspension extract (FIG. 8B) by fluorescence detector. In agreement with the chromatographic separation described by Kelm et al. (U.S. Pat. Appl. No. 2007075020), the unfermented cocoa bean extract consists of up to dodecamer (degree of polymerization=12). This example confirms that procyanidin extracts from cell cultures of *Theobroma cacao* also have the same profile as that reported for beans. FIG. 9 shows the UV absorbance chromatograms of the unfermented cocoa bean extracts (FIG. 9A) and *Theobroma cacao* cell culture extracts (FIG. 9B). This detection mode allows the detection of caffeine and theobromine and the results of this experiment demonstrate that while the extracts from beans show the presence of these two compounds in the extract they are not detected in the extracts of the cell cultures.

Thus, this example shows that cell cultures of *Theobroma cacao* are able to produce procyanidins identical to those in cocoa beans while they do not produce the undesirable compounds caffeine and theobromine. Further, the extraction procedure described here for cell cultures does not require the use of solvents such as hexanes which would be required for the defatting of cocoa beans. Thus, procyanidin extracts derived from cell cultures of *Theobroma cacao* would not have residues of toxic solvents such as hexanes.

Example 18

Antioxidant Activity of Procyanidin Extracts from Cacao Cell Suspension Cultures This example describes the ways to test for antioxidant activity of procyanidins extracted from cacao cells cultured by methods described in the above examples.

Evidence in the literature suggests a relationship between the health promoting properties of cacao procyanidins and the antioxidant properties of these compounds. It is generally believed that these antioxidants affect certain oxidative and free radical processes involved with some types of tumor promotion and LDL oxidation in cardiovascular diseases. Thus, measuring the antioxidant potential of the cacao procyanidins is a reasonable way to determine the effectiveness of these compounds in preventing human diseases such as cancers and heart disease to enable the use of these compounds in compositions with health promoting properties. Similarly, antioxidants are believed to help maintain a younger looking skin with fewer wrinkles and thus, the cacao procyanidins can be used in cosmetic compositions.

The antioxidant capacity of polyphenolic compounds such as cacao procyanidins are measured by a number of procedures known in the art. The most popular method is the Oxygen Radical Absorbance Capacity (ORAC) method (Cao G, Alessio H, Cutler R (1993). "Oxygen-radical absorbance capacity assay for antioxidants" *Free Radic Biol Med* 14 (3): 303-11). The assay measures the oxidative degradation of the fluorescent molecule (either beta-phycoerythrin or fluorescein) after being mixed with free radical generators such as azo-initiator compounds. Azo-initiators are considered to produce peroxyl free radical by heating, which damages the fluorescent molecule, resulting in the loss of fluorescence. Antioxidants are able to protect the fluorescent molecule from oxidative degeneration. The degree of protection will be quantified using a fluorometer. Fluorescein is currently used most as a fluorescent probe. Equipment that can automatically measure and calculate the capacity is commercially available (Biotek, Roche Diagnostics).

The fluorescent intensity decreases as the oxidative degeneration proceeds, and this intensity is typically recorded for 35 minutes after the addition of the azo-initiator (free radical generator). The degeneration (or decomposition) of fluorescein that is measured as the fluorescence delay becomes less prominent by the presence of antioxidants. Decay curves (fluorescence intensity vs. time) are recorded and the area between two decay curves (with or without antioxidant) is calculated. Subsequently, the degree of antioxidant-mediated protection is quantified using the antioxidant trolox (a vitamin E analogue) as a standard. Different concentrations of trolox are used to make a standard curve, and test samples are compared to this. Results for test samples (foods) are reported as "trolox equivalents" or TE.

Example 19

Extraction Efficiency of Procyanidins in Cocoa Cells Using Organic Solvents

Figure 12A:
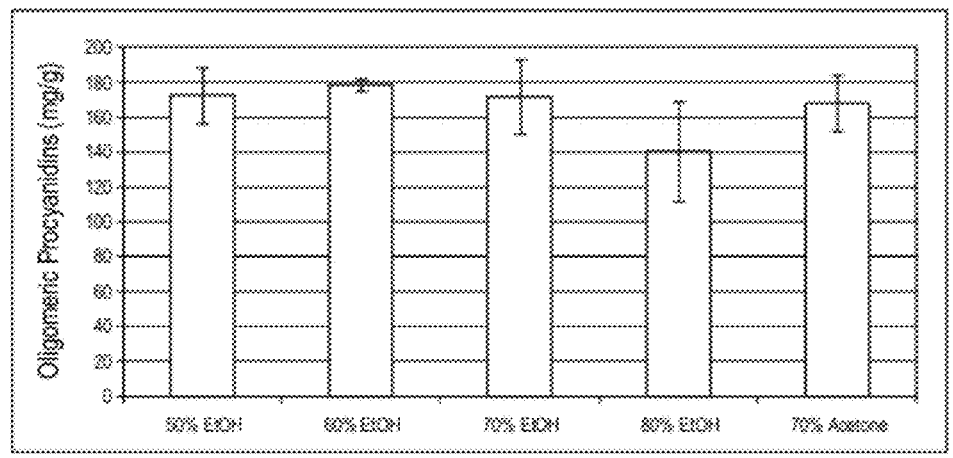
FIG. 12A includes a graph showing comparison of overall procyanidin yields in various aqueous solvents (Intraday, n=3).
Figure 12B:
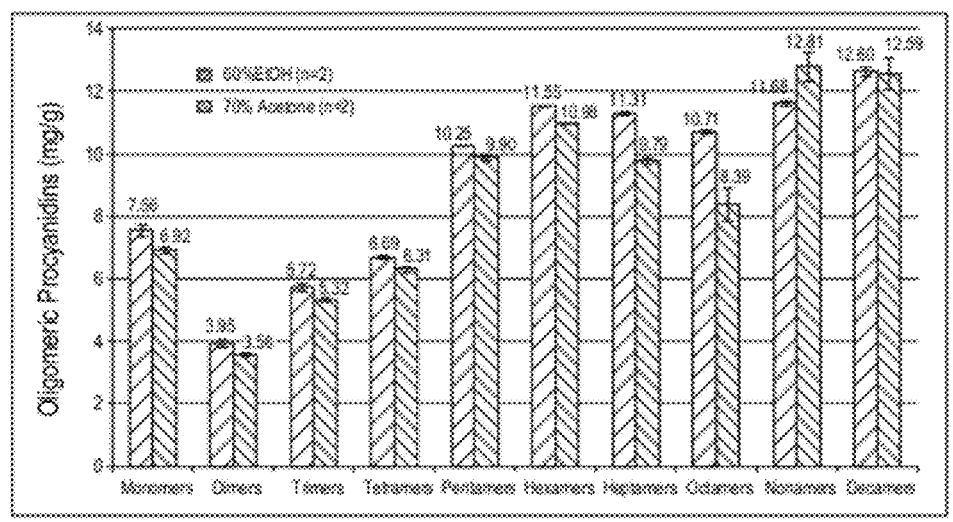
FIG. 12B includes a graph showing comparison of overall extraction rate of oligomeric procyanidins (Monomers through Decamers) for the extraction procedure (n=2).
Figure 12C:
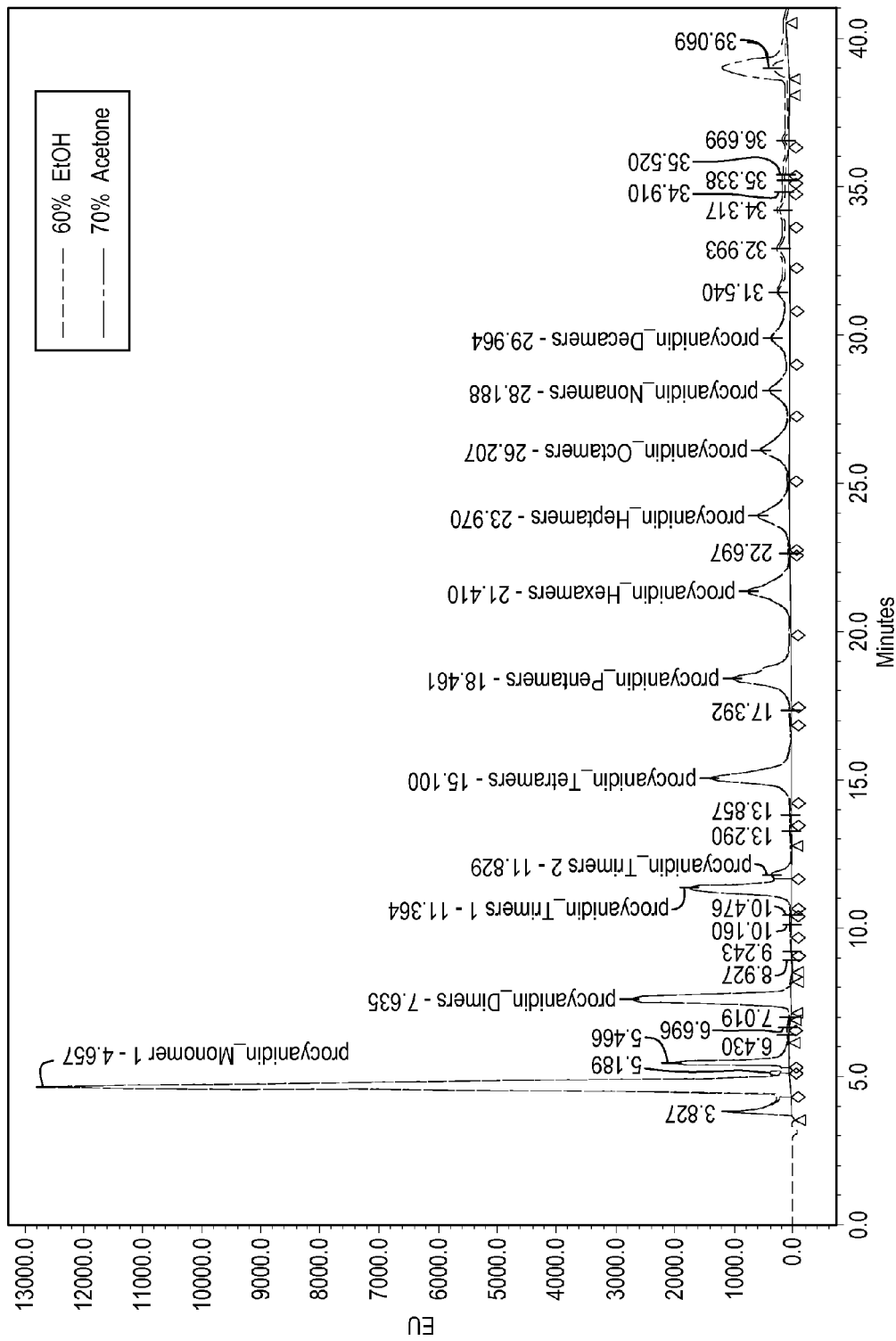
FIG. 12C includes a graph showing comparison of procyanidin profiles in extracts between 60% ethanol and 70% acetone.
Figure 13:
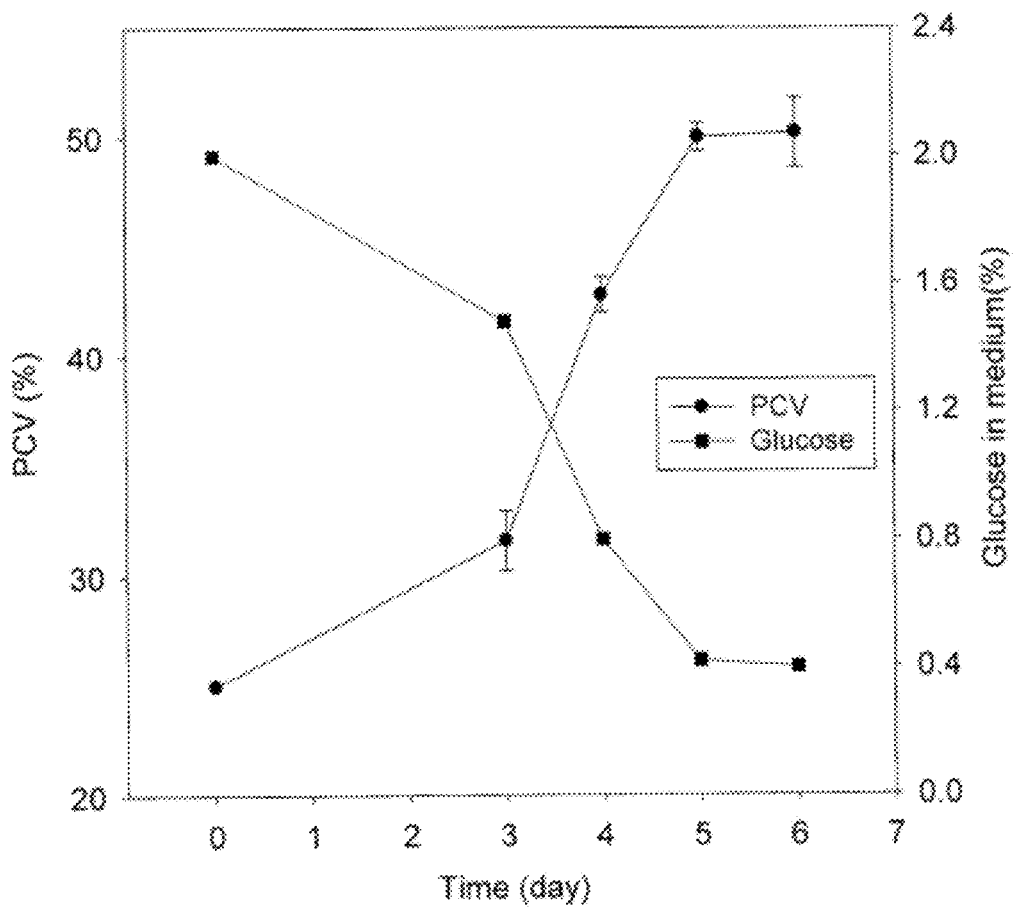
FIG. 13 includes a graph showing typical time courses of biomass density in cultures of various inoculum densities.

In this example the effectiveness of extraction of procyanidins from various aqueous solvents was studied. The solvents were used in various aqueous conditions (30, 40, 50, 60, 70, 80% of acetone, 30, 40, 50, 60, 70 80% of methanol, or 30, 40, 50, 60, 70, 80% of ethanol in the presence of acetic acid, in a range of pH about 3.0-6.0. The extract was analyzed to compare the efficiency of extraction in different conditions. The extracts were prepared from ground cocoa cells as described in example 9. Either 50 mg or 1 g of the ground cocoa cells was used for extracting oligomeric procyanidins using solvents in triplicate. The amounts of individual procyanidins (Monomer through Decamers) in the extracts were determined by the HPLC analytical method as described in example 14. From the results, the 80% EtOH solvent was a less efficient extraction system than other solvents. The 50, 60, 70% EtOH and 70% Acetone were most efficient for all oligomeric procyanidins. In this study the result illustrated that 60% EtOH was the most potent extraction solvent for overall oligomeric procyanidins (FIG. 12A). The 60% EtOH preferentially extracted overall procyanidins (Monomers through Decamers) over the 70% acetone (FIG. 12B, FIG. 12C). In contrast to extraction from cocoa cells, it has been reported that acidified 70% acetone is most effective for extracting oligomeric procyanidins from defatted cocoa solid (U.S. Pat. No. 6,627,232).

Example 20

Stability Testing of Dimeric Procyanidins in Acidic and Neutral Condition

Figure 14B:
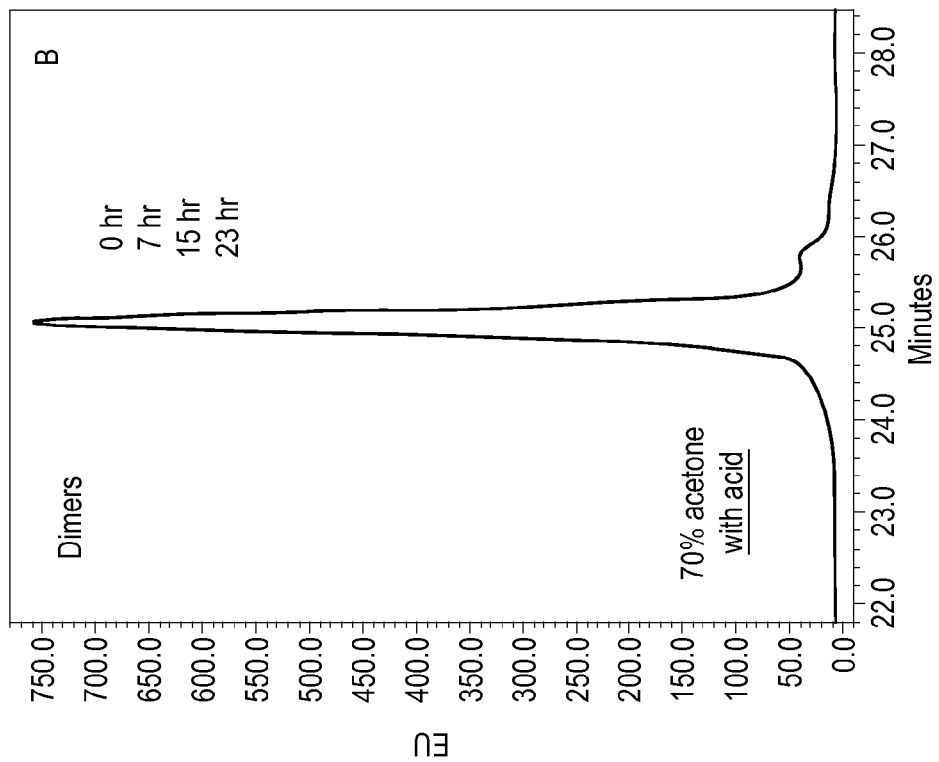
FIGS. 14A-14B include a graph showing comparison of stability of dimeric procyanidins in acidic and non-acidic extraction solvent systems at room temperature within 23 hr.
Figure 14A:
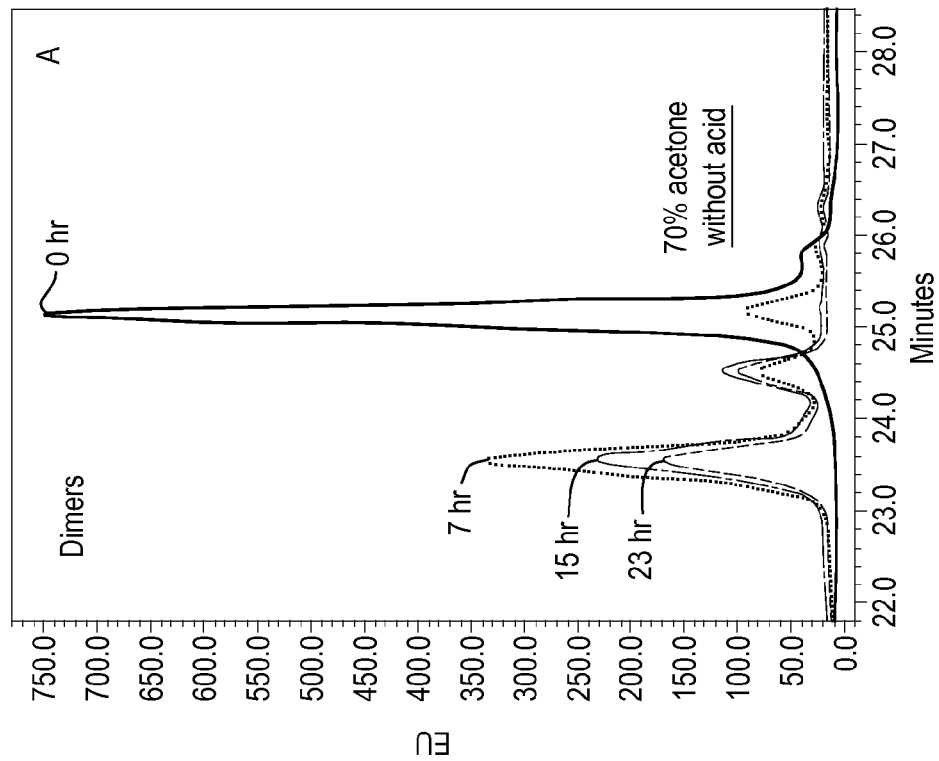

For procyanidins stability acidified 70% acetone has been reported as most effective solvent (Rohr, G. E.; Meier, B.; Sticher, O. *Analysis of procyanidins*. In *Studies in Natural products Chemistry*. Volume 21. *Bioactive Natural Products (Part B)*. Attu-ur-Rahman; Elsevier; Amsterdam, The Netherlands, 2000; pp 497-570). The stability of dimeric procyanidins was carried out under acidic and neutral 70% acetone solvent. Samples were prepared from purified dimeric procyanidin as 5 ug/mL and kept at room temperature over 0 hr to 23 hr. The dimeric procyanidin was detected using a fluorescence detector at 275 nm excitation and 316 nm emission. The chromatographic conditions used were identical to that described above. FIGS. 14A-14B show that after 23 hrs, the dimeric procyanidin (FIG. 14A) in neutral 70% acetone showed significantly degradation. However, the dimeric procyanidin (FIG. 14B) in acidified 70% acetone remained highly stable.

Example 21

Aeration Conditions for Scale-Up of Cocoa Cell Suspensions

Dissolved gases play a critical role for primary and secondary product formation in plant cell culture. In this example, the effectiveness of an aeration strategy whereby gaseous oxygen was supplemented to the inlet gas mixture to boost polyphenol in bioreactor-grown cocoa cells was demonstrated. In a 7.5 L mechanically agitated bioreactor, 0.875 L of cacao cells were inoculated (working volume=3.5 L) and cultivated for a seven day period under 0.1 vvm (volume of gas per volume of culture per minute) of gas (air only) flow rate, 100 RPM agitation speed and 26° C. vessel temperature, followed by a 10 day cultivation period in the presence of glucose elicitor. A parallel bioreactor treated as above, but with a gaseous regime consisting of supplemented oxygen added to the culture medium, which resulted in a 3.1 fold increase in the final concentration of polyphenol per unit packed cell volume as compared to the air-only treated bioreactor-grown cells. The final production yield in the air-only treatment was 9.4 grams procyanidin per PCV and 29.2 grams procyanidin per PCV in the oxygen-supplemented treatment.

TABLE 1

Composition of media I - XXXVI (Recipes for stock solutions are provided in Table 2.

| | I<br>TC723 | II<br>TC726 | III<br>TC727 | IV<br>TC768 | V<br>TC769 | VI<br>TM783 | VII<br>TC784 | VIII<br>TC786 | IX<br>TC787 |
|---|---|---|---|---|---|---|---|---|---|
| MS Medium (Phytotech Catalog # M519) (g/L) | | | | | | | | | |
| MS Vitamins 1000X Stock Solution (Phytotech Catalog # M533) (mL/L) | | | | | | | | | |
| DKW Macro Elements A 10X Stock Solution (mL/L) | 100.0 | | | 100.0 | 100.0 | | 100.0 | | |
| DKW Macro Elements B 10X Stock Solution (mL/L) | 100.0 | | | 100.0 | 100.0 | | 100.0 | | |
| DKW Micro Elements 100X Stock Solution (mL/L) | 10.0 | | | 10.0 | 10.0 | | 10.0 | | |
| DKW Salts (Phytotech Catalog # D190) (g/L) | | | | | | | | | |

TABLE 1-continued

Composition of media I - XXXVI (Recipes for stock solutions are provided in Table 2.)

| Component | | | | | | | | | |
|---|---|---|---|---|---|---|---|---|---|
| WPM Salts (Sigma-Aldrich Catalog # M6774) (g/L) | | 2.3 | 2.3 | | | | | | |
| CP Salts (Sigma-Aldrich Catalog # C6798) (g/L) | | | | | | | | | 4.5 |
| SH Salts (Phytotech Catalog # S816) (g/L) | | | | | 3.2 | 3.2 | | | |
| QL Salts (Phytotech Catalog # Q673) (g/L) | | | | | | | | | |
| B5 Major Salts IM1 medium 10X Stock Solution (mL/L) | | | | | | | | | |
| MS Minor Salts MM medium 1000X Stock Solution (mL/L) | | | | | | | | | |
| MS Salts (Phytotech Catalog # M524) (g/L) | | | | | | | | | |
| MM/IM1 Vitamins 1000X Stock Solution (mL/L) | | | | | | | | | |
| NN Vitamins 1000X Stock Solution (Phytotech Catalog # N608) (mL/L) | | | | | 1.0 | 1.0 | | | |
| DKW Vitamins 1000X Stock Solution (mL/L) | 1.0 | | | 1.0 | 1.0 | | | 1.0 | |
| B5 Vitamins Stock Solution (Phytatech Catalog # G249) (mL/L) | | 1.0 | 1.0 | | | | | | 1.0 |
| Dicamba (mg/L) | | | | | | | | 0.5 | |
| 2,4-D (mg/L) | 2.0 | 2.0 | 2.0 | 1.0 | | 0.5 | | 2.0 | 1.0 |
| 2iP (mg/L) | | | | | 0.5 | 0.5 | | | 0.05 |
| IAA (mg/L) | | | | | 10.0 | | | | 4.0 |
| NAA (mg/L) | | | | | | 0.5 | | | |
| Kinetin (mg/L) | | | 0.3 | | | | | | |
| TDZ (mg/L) | 0.005 | | | 0.005 | 0.005 | | | 0.005 | |
| BA (mg/L) | | 0.05 | | | | | | | |
| Sucrose (g/L) | | | | | | | 20.0 | | 15.0 |
| D-Glucose (g/L) | 20.0 | 20.0 | 20.0 | 20.0 | 20.0 | | 20.0 | 20.0 | 15.0 |
| Coconut water (mL/L) | | | 50.0 | | | | | | |
| L-Glutamine (mg/L) | 250.0 | | | 250.0 | 250.0 | 800.0 | 800.0 | 250.0 | 800.0 |
| Myo-Inositol (mg/L) | 100.0 | | | 100.0 | 100.0 | | | 100.0 | 100.0 |
| Glycine (mg/L) | | | | | | | | | 2.0 |
| Iron Solution 1000X Stock Solution (mL/L) | 1.0 | | | 1.0 | 1.0 | | | 1.0 | |
| Phytagel (g/L) | 2.0 | 2.2 | 2.2 | 2.0 | 2.0 | | | | |
| Agar (g/L) | | | | | | | | | |
| IBA (mg/L) | | | | | | | | | |
| Casein Enzymatic Hydrolysate (mg/L) | | | | | | | | | |

TABLE 1-continued

Composition of media I - XXXVI (Recipes for stock solutions are provided in Table 2.

| | X TC788 | XI TC810 | XII TM812 | XIII TC815 | XIV TC819 | XV TC822 | XVI TC823 | XVII TC824 | XVIII TC825 |
|---|---|---|---|---|---|---|---|---|---|
| MS Medium (Phytotech Catalog # M519) (g/L) | | | | | | | | | |
| MS Vitamins 1000X Stock Solution (Phytotech Catalog # M533) (mL/L) | | | | | | | | | |
| DKW Macro Elements A 10X Stock Solution (mL/L) | | | | 100.0 | | | | | |
| DKW Macro Elements B 10X Stock Solution (mL/L) | | | | 100.0 | | | | | |
| DKW Micro Elements 100X Stock Solution (mL/L) | | | | 10.0 | | | | | |
| DKW Salts (Phytotech Catalog # D190) (g/L) | | | | | | | | | |
| WPM Salts (Sigma-Aldrich Catalog # M6774) (g/L) | | | | | 2.3 | | | | |
| CP Salts (Sigma-Aldrich Catalog # C6798) (g/L) | | | | | | | | | |
| SH Salts (Phytotech Catalog # S816) (g/L) | | 3.2 | | | | | | | 3.2 |
| QL Salts (Phytotech Catalog # Q673) (g/L) | 3.56 | | 3.56 | | | 3.56 | 3.56 | 3.56 | |
| B5 Major Salts IM1 medium 10X Stock Solution (mL/L) | | | | | | | | | |
| MS Minor Salts MM medium 1000X Stock Solution (mL/L) | | | | | | | | | |
| MS Salts (Phytotech Catalog # M524) (g/L) | | | | | | | | | |
| MM/IM1 Vitamins 1000X Stock Solution (mL/L) | | | | | | | | | |
| NN Vitamins 1000X Stock Solution (Phytotech Catalog # N608) (mL/L) | | 1.0 | 1.0 | | 1.0 | 1.0 | 1.0 | | |
| DKW Vitamins 1000X Stock Solution (mL/L) | | | | 1.0 | | | | | |
| B5 Vitamins Stock Solution (Phytatech Catalog # G249) (mL/L) | 1.0 | | | | | | | 1.0 | 1.0 |
| Dicamba (mg/L) | | 0.5 | 0.5 | | 0.5 | 0.5 | 0.5 | | |
| 2,4-D (mg/L) | 1.0 | | | 2.0 | | | | 2.0 | 2.0 |

TABLE 1-continued

Composition of media I - XXXVI (Recipes for stock solutions are provided in Table 2.

| | | | | | | | | | |
|---|---|---|---|---|---|---|---|---|---|
| 2iP (mg/L) | 0.05 | 0.5 | 0.5 | | 0.5 | 0.5 | 0.5 | | |
| IAA (mg/L) | 4.0 | | | | | | | | |
| NAA (mg/L) | | 0.5 | 0.5 | | 0.5 | 0.5 | | | |
| Kinetin (mg/L) | | | | | | | | | |
| TDZ (mg/L) | | | | 0.005 | | | | 0.005 | 0.005 |
| BA (mg/L) | | | | | | | | | |
| Sucrose (g/L) | 15.0 | 10.0 | 20.0 | | 20.0 | | 10.0 | | |
| D-Glucose (g/L) | 15.0 | 10.0 | | 20.0 | | 20.0 | 10.0 | 20.0 | 20.0 |
| Coconut water (mL/L) | | | | | | | | | |
| L-Glutamine (mg/L) | 800.0 | 800.0 | 800.0 | 250.0 | 800.0 | 800.0 | 800.0 | 800.0 | 800.0 |
| Myo-Inositol (mg/L) | 100.0 | | | 100.0 | | | | | |
| Glycine (mg/L) | 2.0 | | | | | | | 2.0 | 2.0 |
| Iron Solution 1000X Stock Solution (mL/L) | | | | 1.0 | | | | | |
| Phytagel (g/L) | | | | | | | | | |
| Agar (g/L) | | | | | | | | | |
| IBA (mg/L) | | | | | | | | | |
| Casein Enzymatic Hydrolysate (mg/L) | | | | | | | | | |

| | XIX TC826 | XX TC827 | XXI TC829 | XXII TM434 | XXIII TM784 | XXIV TC1599 | XXV TC1234 | XXVI DC1151 | XXVII TC1248 |
|---|---|---|---|---|---|---|---|---|---|
| MS Medium (Phytotech Catalog # M519) (g/L) | | | | | | 4.43 | | | 4.43 |
| MS Vitamins 1000X Stock Solution (Phytotech Catalog # M533) (mL/L) | | | | | | 1.0 | | | 1.0 |
| DKW Macro Elements A 10X Stock Solution (mL/L) | | | | | | | | | |
| DKW Macro Elements B 10X Stock Solution (mL/L) | | | | | | | | | |
| DKW Micro Elements 100X Stock Solution (mL/L) | | | | | | | | | |
| DKW Salts (Phytotech Catalog # D190) (g/L | | | | | | | | | |
| WPM Salts (Sigma-Aldrich Catalog # M6774) (g/L) | 2.3 | 2.3 | 2.3 | | | | | | |
| CP Salts (Sigma-Aldrich Catalog # C6798) (g/L) | | | | | | | | | |
| SH Salts (Phytotech Catalog # S816) (g/L) | | | | 3.2 | 3.2 | | | | |
| QL Salts (Phytotech Catalog # Q673) (g/L) | | | | | | | | | |

TABLE 1-continued

Composition of media I - XXXVI (Recipes for stock solutions are provided in Table 2.)

| Component | | | | | | | | | |
|---|---|---|---|---|---|---|---|---|---|
| B5 Major Salts IM1 medium 10X Stock Solution (mL/L) | | | | | | 100 | | | |
| MS Minor Salts MM medium 1000X Stock Solution (mL/L) | | | | | | | 1.0 | | |
| MS Salts (Phytotech Catalog # M524) (g/L) | | | | | | | | 4.3 | |
| MM/IM1 Vitamins 1000X Stock Solution (mL/L) | | | | | | | 1.0 | | |
| NN Vitamins 1000X Stock Solution (Phytotech Catalog # N608) (mL/L) | | 1.0 | 1.0 | 1.0 | 1.0 | | | 1.0 | |
| DKW Vitamins 1000X Stock Solution (mL/L) | | | | | | | | | |
| B5 Vitamins Stock Solution (Phytatech Catalog # G249) (mL/L) | 1.0 | | | | | | | | |
| Dicamba (mg/L) | | 0.5 | 0.5 | 0.5 | 0.5 | | | | |
| 2,4-D (mg/L) | 2.0 | | | | | | | 1.5 | |
| 2iP (mg/L) | | 0.5 | 0.5 | 0.5 | 0.5 | | | | |
| IAA (mg/L) | | | | | | 2.0 | | | 2.0 |
| NAA (mg/L) | | 0.5 | 0.5 | 0.5 | 0.5 | | 0.1 | | |
| Kinetin (mg/L) | | | | | | | 0.2 | | |
| TDZ (mg/L) | 0.005 | | | | | 0.005 | | | 0.005 |
| BA (mg/L) | | | | | | | | | |
| Sucrose (g/L) | | | 10.0 | 20.0 | | | 60.0 | 30.0 | |
| D-Glucose (g/L) | 20.0 | 20.0 | 10.0 | | 20.0 | 20.0 | | | 20.0 |
| Coconut water (mL/L) | | | | | | | | | |
| L-Glutamine (mg/L) | 800.0 | 800.0 | 800.0 | 800.0 | 800.0 | 250.0 | | | 250.0 |
| Myo-Inositol (mg/L) | | | | | | | | | |
| Glycine (mg/L) | 2.0 | | | | | | | | |
| Iron Solution 1000X Stock Solution (mL/L) | | | | | | | | | |
| Phytagel (g/L) | | | | | | | | | |
| Agar (g/L) | | | | | | | | | 7.0 |
| IBA (mg/L) | | | | | | 4.0 | | | 4.0 |
| Casein Enzymatic Hydrolysate (mg/L) | | | | | | | 250.0 | | |

| | XXVIII TC1596 | XXIX TC1632 | XXX TC1633 | XXXI TC1634 | XXXII TC1482 | XXXIII TC1682 | XXXIV TC1701 |
|---|---|---|---|---|---|---|---|
| MS Medium (Phytotech Catalog # M519) (g/L) | 4.43 | 4.43 | 4.43 | 4.43 | | 4.43 | 4.43 |
| MS Vitamins 1000X Stock Solution (Phytotech Catalog # M533) (mL/L) | 1.0 | 1.0 | | | | 1.0 | 1.0 |

TABLE 1-continued

Composition of media I - XXXVI (Recipes for stock solutions are provided in Table 2.

| | | | | | | | |
|---|---|---|---|---|---|---|---|
| DKW Macro Elements A 10X Stock Solution (mL/L) | | | | | | | |
| DKW Macro Elements B 10X Stock Solution (mL/L) | | | | | | | |
| DKW Micro Elements 100X Stock Solution (mL/L) | | | | | | | |
| DKW Salts (Phytotech Catalog # D190) (g/L | | | | | 5.22 | | |
| WPM Salts (Sigma-Aldrich Catalog # M6774) (g/L) | | | | | | | |
| CP Salts (Sigma-Aldrich Catalog # C6798) (g/L) | | | | | | | |
| SH Salts (Phytotech Catalog # S816) (g/L) | | | | | | | |
| QL Salts (Phytotech Catalog # Q673) (g/L) | | | | | | | |
| B5 Major Salts IM1 medium 10X Stock Solution (mL/L) | | | | | | | |
| MS Minor Salts MM medium 1000X Stock Solution (mL/L) | | | | | | | |
| MS Salts (Phytotech Catalog # M524) (g/L) | | | | | | | |
| MM/IM1 Vitamins 1000X Stock Solution (mL/L) | | | | | | | |
| NN Vitamins 1000X Stock Solution (Phytotech Catalog # N608) (mL/L) | | | | | | | |
| DKW Vitamins 1000X Stock Solution (mL/L) | | | | | 1.0 | | |
| B5 Vitamins Stock Solution (Phytatech Catalog # G249) (mL/L) | | | | | | | |
| Dicamba (mg/L) | | | | | | | |
| 2,4-D (mg/L) | | | | | 2.0 | | |
| 2iP (mg/L) | | | | | | | |
| IAA (mg/L) | 2.0 | | | | | 1.0 | 2.0 |
| NAA (mg/L) | | | | | | | |
| Kinetin (mg/L) | | | | | | | |
| TDZ (mg/L) | 0.005 | 0.005 | 0.005 | 0.005 | 0.005 | 0.005 | 0.005 |
| BA (mg/L) | | | | | | | |
| Sucrose (g/L) | | | | | | | |
| D-Glucose (g/L) | 20.0 | 20.0 | 20.0 | 20.0 | 20.0 | 20.0 | 20.0 |
| Coconut water (mL/L) | | | | | | | |
| L-Glutamine (mg/L) | 250.0 | 250.0 | 250.0 | | 250.0 | 250.0 | 250.0 |
| Myo-Inositol (mg/L) | | | | | 100.0 | | |
| Glycine (mg/L) | | | | | | | |
| Iron Solution 1000X Stock Solution (mL/L) | | | | | | | |
| Phytagel (g/L) | | | | | | | |

TABLE 1-continued

Composition of media I - XXXVI (Recipes for stock solutions are provided in Table 2.

| | | | | | | |
|---|---|---|---|---|---|---|
| Agar (g/L) | 7.0 | 7.0 | 7.0 | 7.0 | | |
| IBA (mg/L) | 2.0 | 2.0 | 2.0 | 2.0 | 2.0 | 2.0 |
| Casein Enzymatic Hydrolysate (mg/L) | | | | | | |

| | XXXV TC1878 | XXXVI TC3015 | XXXVII TC3150 |
|---|---|---|---|
| MS Medium (Phytotech Catalog # M519) (g/L) | 4.43 | 4.43 | 4.43 |
| MS Vitamins 1000X Stock Solution (Phytotech Catalog # M533) (mL/L) | 1.0 | 1.0 | 1.0 |
| DKW Macro Elements A 10X Stock Solution (mL/L) | | | |
| DKW Macro Elements B 10X Stock Solution (mL/L) | | | |
| DKW Micro Elements 100X Stock Solution (mL/L) | | | |
| DKW Salts (Phytotech Catalog # D190) (g/L) | | | |
| WPM Salts (Sigma-Aldrich Catalog # M6774) (g/L) | | | |
| CP Salts (Sigma-Aldrich Catalog # C6798) (g/L) | | | |
| SH Salts (Phytotech Catalog # S816) (g/L) | | | |
| QL Salts (Phytotech Catalog # Q673) (g/L) | | | |
| B5 Major Salts IM1 medium 10X Stock Solution (mL/L) | | | |
| MS Minor Salts MM medium 1000X Stock Solution (mL/L) | | | |
| MS Salts (Phytotech Catalog # M524) (g/L) | | | |
| MM/IM1 Vitamins 1000X Stock Solution (mL/L) | | | |
| NN Vitamins 1000X Stock Solution (Phytotech Catalog # N608) (mL/L) | | | |
| DKW Vitamins 1000X Stock Solution (mL/L) | | | |
| B5 Vitamins Stock Solution (Phytatech | | | |

TABLE 1-continued

Composition of media I - XXXVI (Recipes for stock solutions are provided in Table 2.

| | | | |
|---|---|---|---|
| Catalog # G249) (mL/L) | | | |
| Dicamba (mg/L) | | | |
| 2,4-D (mg/L) | | | |
| 2iP (mg/L) | | | |
| IAA (mg/L) | 1.0 | | 1.0 |
| NAA (mg/L) | | | |
| Kinetin (mg/L) | | | |
| TDZ (mg/L) | 0.005 | | 0.005 |
| BA (mg/L) | | | |
| Sucrose (g/L) | | | |
| D-Glucose (g/L) | 30.0 | 30.0 | 40.0 |
| Coconut water (mL/L) | | | |
| L-Glutamine (mg/L) | 250.0 | 250.0 | 250.0 |
| Myo-Inositol (mg/L) | | | |
| Glycine (mg/L) | | | |
| Iron Solution 1000X Stock Solution (mL/L) | | | |
| Phytagel (g/L) | | | |
| Agar (g/L) | | | |
| IBA (mg/L) | 2.0 | | 2.0 |
| Casein Enzymatic Hydrolysate (mg/L) | | | |

TABLE 2

Recipes for Stock Solutions Used in Media Described in Table 1

| Stock Solution Name | Volume | Chemical | Amount |
|---|---|---|---|
| DKW 10X Macro Elements Solution A | 1 L | $NH_4NO_3$ | 14.16 g |
| | | $Ca(NO_3)_2 \cdot 4H_2O$ | 19.69 g |
| DKW 10X Macro Elements Solution B | 1 L | $CaCl_2 \cdot 2H_2O$ | 1.49 g |
| | | $K_2SO_4$ | 15.59 g |
| | | $MgSO_4 \cdot 7H_2O$ | 7.40 g |
| | | $KH_2PO_4$ | 2.65 g |
| DKW 100X Micro Elements Solution | 1 L | $Zn(NO_3)_2 \cdot 6H_2O$ | 1.70 g |
| | | $MnSO_4 \cdot H_2O$ | 3.34 g |
| | | $CuSO_4 \cdot 5H_2O$ | 25.0 mg |
| | | $H_3BO_4$ | 480.0 mg |
| | | $Na_2MoO_4 \cdot 2H_2O$ | 39.0 mg |
| Iron Solution 1000X Stock Solution | 1 L | $Na_2EDTA$ (0.5M solution) | 200 ml |
| | | $FeSO_4 \cdot 7H_2O$ | 27.8 g |
| DKW 1000X Vitamins Stock Solution | 100 mL | Myo-Inositol | 10.0 g |
| | | Thiamine-HCl | 0.2 g |
| | | Nicotinic acid | 0.1 g |
| | | Glycine | 0.2 g |
| B5 1000X Vitamin Stock Solution | 50 mL | Myo-Inositol | 5.0 g |
| | | Nicotinic acid | 50.0 mg |
| | | Pyridoxine | 50 mg |
| | | Thiamine | 500.0 mg |
| B5 Major Salts IM1 10X Stock Solution | 1 L | $(NH_4)_2SO_4$ | 2.68 g |
| | | $CaCl_2$ | 1.13 g |
| | | $MgSO_4$ | 2.44 g |
| | | $KNO_3$ | 25.0 g |
| | | $NaH_2PO_4$ | 3.0 g |
| MS Minor Salts MM 1000X Stock Solution | 1 L | $MnSO_4 \cdot H_2O$ | 16.9 g |
| | | $ZnSO_4 \cdot 7H_2O$ | 8.6 g |
| | | $H_3BO_4$ | 6.2 g |
| | | KI | 0.83 g |
| | | $Na_2MoO_4 \cdot 2H_2O$ | 0.25 g |
| | | $CuSO_4 \cdot 5H_2O$ | 25.0 mg |
| | | $CoCl_2 \cdot 6H_2O$ | 25.0 mg |

TABLE 2-continued

Recipes for Stock Solutions Used in Media Described in Table 1

| Stock Solution Name | Volume | Chemical | Amount | |
|---|---|---|---|---|
| MM/IM1 Vitamins 1000X Stock Solution | 1 L | Biotin | 10.0 | mg |
| | | Calcium pantothenate | 1.0 | g |
| | | Myo-Inositol | 100.0 | g |
| | | Pyridoxine | 1.0 | g |
| | | Thiamine | 1.0 | g |
| | | Pyridine-3-carboxylic acid | 1.0 | g |

TABLE 3

Analysis of caffeine and theobromine in cocoa cell and unfermented cocoa bean extract

| | | Concentration (ug/mg) | Concentration (%) | STDEV | RSD (%) |
|---|---|---|---|---|---|
| Cocoa cell extract | Caffeine (n = 2) | 0.73 | 0.07 | 0.04 | 5.10 |
| | Theobromine (n = 2) | 0.29 | 0.03 | 0.00 | 0.70 |
| Unfermented cocoa bean extract | Caffeine (n = 2) | 14.14 | 1.41 | 0.00 | 0.00 |
| | Theobromine (n = 2) | 49.36 | 4.94 | 0.68 | 1.40 |

The invention claimed is:

1. An isolated cocoa cell line, comprising cocoa callus cells derived from a *Theobroma cacao* plant, the callus cells being selected to produce greater than 100 mg of procyanidins per liter of cell culture, greater than 200 mg of procyanidins per liter of packed cells, and less than 0.5 ug caffeine and less than 0.75 ug theobromine per mg of procyanidins when grown in a cell suspension culture comprising a carbon source, a nitrogen source, and one or more supplements selected from the group consisting of a macronutrient, a micronutrient, an auxin, a cytokinin, a vitamin, an amino acid, a hormone, inositol, and a myo-inositol.

2. The isolated cocoa cell line of claim 1, wherein the isolated cocoa cell line is derived from floral tissue or a non-floral vegetative tissue, or both, the floral tissue being selected from the group consisting of petals, sepals, staminodes, and combinations thereof, the non-floral vegetative tissue being selected from the group consisting of nodes, internodes, young leaves, mature leaves, stems, roots, and combinations thereof.

3. A method of preparing cocoa oligomeric procyanidins, the method comprising:
culturing cocoa callus cells derived from a *Theobroma cacao* plant in a culture medium for a time sufficient and under conditions sufficient to result in production of cocoa oligomeric procyanidins at a first rate; and
inducing the cells to produce the cocoa oligomeric procyanidins at a second rate that is higher than the first rate by introducing a selected amount of a carbohydrate to the cells, the cells producing greater than 100 mg of procyanidins per liter of cell culture, greater than 200 mg of procyanidins per liter of packed cells, and less than 0.5 ug caffeine and less than 0.75 ug theobromine per mg of procyanidins, thereby preparing cocoa oligomeric procyanidins,
wherein said step of culturing the cocoa cells is carried out in the presence of dissolved oxygen concentration at 1% to 400% of air saturation.

4. The method of claim 3, further comprising extracting the cocoa oligomeric procyanidins from the cells after the inducing step.

5. The method of claim 4, wherein the extracting occurs between 1 day to 10 days after introduction of the carbohydrate.

6. The method of claim 4, wherein the extracting is carried out with an ethanol-based extraction solution or an acidic extraction solution, or both.

7. The method of claim 3, wherein the carbohydrate comprises glucose.

8. The method of claim 3, wherein the carbohydrate is introduced during or after a last phase of an exponential growth state.

9. The method of claim 3, wherein the culture medium is a hormone-free medium.

10. The method of claim 9, further comprising introducing a carbohydrate to the cells in the hormone-free medium in an amount sufficient for inducing the cells to produce the cocoa oligomeric procyanidins at a third rate that is higher than the second rate.

11. The method of claim 3, wherein introduction of the carbohydrate is in an amount of about 0.5% to about 20% by volume of the culture medium and results in one or more of stable cell line maintenance, induction of overproduction of the cocoa oligomeric procyanidins, or prevention of cell aggregation.

12. The method of claim 3, wherein said step of inducing the cells is carried out in the presence of dissolved oxygen concentration at 1% to 400% of air saturation.

13. The method of claim 3, further comprising one or more of the following:
harvesting the cells;
homogenizing cell biomass in a suitable solvent for extraction of polyphenol rich fraction;
isolating a procyanidin rich fraction using solvent-solvent extraction and/or chromatography; or
drying or concentrating the procyanidin fraction.

14. The method of claim 3, further comprising one or more of the following:
growing callus cells derived from a plant belonging to the genus *Theobroma* on solid growth medium;
selecting a rapidly growing cell line from a callus culture comprising cells derived from a plant belonging to the genus *Theobroma*; or initiating a cell suspension culture by inoculating the rapidly growing cell line into liquid medium.

15. A method of preparing cocoa oligomeric procyanidins, the method comprising:
   culturing cocoa callus cells derived from a *Theobroma cacao* plant in a hormone-free medium for a time sufficient and under conditions sufficient for inducing the cells to produce cocoa oligomeric procyanidins at a first rate; and
   inducing the cells to produce the cocoa oligomeric procyanidins at a second rate that is higher than the first rate by introducing a selected amount of a carbohydrate to the cells, the cells producing greater than 100 mg of procyanidins per liter of cell culture, greater than 200 mg of procyanidins per liter of packed cells, and less than 0.5 ug caffeine and less than 0.75 ug theobromine per mg of procyanidins, thereby preparing cocoa oligomeric procyanidins.

16. The method of claim 15, further comprising extracting the cocoa oligomeric procyanidins from the cells after the inducing step.

17. The method of claim 15, wherein the carbohydrate comprises glucose.

18. The method of claim 15, wherein introduction of the carbohydrate is in an amount of about 0.5% to about 20% by volume of the culture medium and results in one or more of stable cell line maintenance, induction of overproduction of the cocoa oligomeric procyanidins, or prevention of cell aggregation.

19. The method of claim 15, wherein said step of culturing the cocoa cells is carried out in the presence of dissolved oxygen concentration at 1% to 400% of air saturation during a growth stage.

20. The method of claim 15, wherein said step of inducing the cocoa cells is carried out in the presence of dissolved oxygen concentration at 1% to 400% of air saturation.

21. The isolated cocoa cell line of claim 1, wherein the callus cells are selected to have a doubling time between 10 and 15 days and are selected to grow to a biomass concentration between 40% and 69% packed cell volume in cell suspension culture.

22. The isolated cocoa cell line of claim 1, wherein the procyanidins include oligomeric procyanidins selected from the group consisting of dimers through dodecamers.

23. The isolated cocoa cell line of claim 1, wherein the callus cells are selected to produce at least 250 mg of procyanidins per liter of cell culture and greater than 500 mg of procyanidins per liter of packed cells.

24. The isolated cocoa cell line of claim 1, wherein the callus cells are selected to produce at least 1600 mg of procyanidins per liter of cell culture and greater than 5000 mg of procyanidins per liter of packed cells.

25. A cell suspension culture, comprising:
   the cocoa callus cells of claim 1; and
   a suspension medium,
   the callus cells growing in the suspension medium, the suspension medium comprising a carbon source, a nitrogen source, and one or more supplements selected from the group consisting of a macronutrient, a micronutrient, an auxin, a cytokinin, a vitamin, an amino acid, a hormone, inositol, and a myo-inositol, the callus cells producing greater than 100 mg of procyanidins per liter of cell culture, greater than 200 mg of procyanidins per liter of packed cells, and less than 0.5 ug caffeine and less than 0.75 ug theobromine per mg of procyanidins in the suspension medium.

* * * * *